(12) United States Patent
Nikolovska-Coleska et al.

(10) Patent No.: US 9,394,303 B2
(45) Date of Patent: Jul. 19, 2016

(54) SMALL MOLECULE INHIBITORS OF MCL-1 AND USES THEREOF

(71) Applicant: THE REGENTS OF THE UNIVERSITY OF MICHIGAN, Ann Arbor, MI (US)

(72) Inventors: Zaneta Nikolovska-Coleska, Ann Arbor, MI (US); Fardokht Abulwerdi, Frederick, MD (US); Hollis Showalter, Ann Arbor, MI (US); Lei Miao, Ann Arbor, MI (US); Jeanne Stuckey, Fenton, MI (US); Ahmed Mady, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/678,267

(22) Filed: Apr. 3, 2015

(65) Prior Publication Data
US 2015/0284387 A1    Oct. 8, 2015

Related U.S. Application Data

(60) Provisional application No. 61/975,297, filed on Apr. 4, 2014.

(51) Int. Cl.
| | |
|---|---|
| *C07D 401/14* | (2006.01) |
| *A61K 31/437* | (2006.01) |
| *C07D 471/04* | (2006.01) |
| *A61K 31/5377* | (2006.01) |
| *A61K 45/06* | (2006.01) |
| *A61N 5/10* | (2006.01) |

(52) U.S. Cl.
CPC ............ *C07D 471/04* (2013.01); *A61K 31/437* (2013.01); *A61K 31/5377* (2013.01); *A61K 45/06* (2013.01); *A61N 5/10* (2013.01); *A61N 2005/1098* (2013.01)

(58) Field of Classification Search
CPC ............................ C07D 401/14; A61K 31/437
USPC .......................................... 546/119; 514/303
See application file for complete search history.

(56) References Cited

U.S. PATENT DOCUMENTS

| | | | |
|---|---|---|---|
| 6,200,763 | B1 | 3/2001 | Craig |
| 8,445,679 | B2 | 5/2013 | Wang et al. |
| 2006/0004003 | A1 | 1/2006 | Abe et al. |
| 2009/0054402 | A1 | 2/2009 | Wang et al. |
| 2009/0163545 | A1* | 6/2009 | Goldfarb ............. A61K 31/122 514/312 |
| 2010/0256141 | A1 | 10/2010 | Nemecek et al. |
| 2013/0005743 | A1* | 1/2013 | Eskildsen ............ C07D 471/04 514/256 |

FOREIGN PATENT DOCUMENTS

| | | | |
|---|---|---|---|
| WO | 2004/022580 | | 3/2004 |
| WO | 2009/150614 | | 12/2009 |
| WO | 2010/080478 | | 7/2010 |
| WO | 2011058766 | * | 5/2011 |
| WO | 2013/039988 | | 3/2013 |
| WO | 2013/052943 | | 4/2013 |

OTHER PUBLICATIONS

Volochnyuk et al., Journal of Combinatorial Chemistry (2010), 12(4), 510-517.*
Abad-Zapatero, C. et al., "Ligand efficiency indices as guideposts for drug discovery." Drug Discov Today 2005, 10 (7), 464-9.
Chen S., et al., "Mcl-1 Down-regulation Potentiates ABT-737 Lethality by Cooperatively Inducing Bak Activation and Bax Translocation." Cancer Res. 2007; 67:782-91.
Czabotar Pe et al., "Structural insights into the degradation of Mcl-1 induced by BH3 domains." Proc Natl Acad Sci U S A 2007, 104, 6217-22.
Dai W. et al., "Synthesis of the parent and substituted tetracyclic ABCD ring cores of camptothecins via 1-(3-aryl-2-propynyl)-1,6-dihydro-6-oxo-2-pyridinecarbonitriles." Org Lett 2006, 8, 4665-7.
Dash R. et al., "Apogossypol derivative B1-97C1 (Sabutoclax) targeting Mcl-1 sensitizes prostate cancer cells to mda-7/IL-24-mediated toxicity." Proc Natl Acad Sci U S A. 2011, 108(21):8785-90.
Day Cl et al., "Solution structure of prosurvival Mcl-1 and characterization of its binding by proapoptotic BH3-only ligands." J Biol Chem. 2005; 280:4738-44.
Day Cl et al., "Structure of the BH3 domains from the p53-inducible BH3-only proteins Noxa and Puma in complex with Mcl." J Mol Biol. 2008;380:958-71.
Du Y., et al., "A dual-readout F2 assay that combines fluorescence resonance energy transfer and fluorescence polarization for monitoring bimolecular interactions." Assay Drug Dev Technol 2011, 9, 382-93.
Ganesan A. et al., "Synthesis of unsymmetrical pyrazines by reaction of an oxadiazinone with enamines." Journal of Organic Chemistry 1993, 58, 6155-6157.
Schrödinger Suite 2011 Induced Fit Docking protocol; Glide version 5.7, Schrodinger, LLC, New York, NY, 2009; Prime version 3.0, Schrödinger, LLC, New York, NY. 2011, 2 pages.
Greig I. R., et al., "Development and characterization of biphenylsulfonamides as novel inhibitors of bone resorption." J Med Chem 2006, 49, 7487-92.
Guoan X, et al., "Adenovirus-mediated siRNA targeting Mcl-1 gene increases radiosensitivity of pancreatic carcinoma cells in vitro and in vivo." Surgery. 2010;147:553-61.
Hajduk P. J., "Fragment-based drug design: how big is too big?" J. Med Chem 2006, 49, 6972-6.
Huang S, et al., "BH3 mimetic ABT-737 potentiates TRAIL-mediated apoptotic signaling by unsequestering Bim and Bak in human pancreatic cancer cells." Cancer Res. 2008;68:2944-51.
Li X., et al. "Structure-based design, synthesis, and antimicrobial activity of indazole-derived SAH/MTA nucleosidase inhibitors." J Med Chem 2003, 46, 5663-73.
Lipinski C. A. et al., "Experimental and computational approaches to estimate solubility and permeability in drug discovery and development settings." Adv Drug Deily Rev 2001, 46, 3-26.
MacArron R., et al., "Impact of high-throughput screening in biomedical research." Nat Rev Drug Discov 2011, 10, 188-95.
Martins A., et al., "Synthesis of substituted benzoxacycles via a domino ortho-alkylation/Heck coupling sequence." J Org Chem 2006, 71, 4937-42.

(Continued)

*Primary Examiner* — Niloofar Rahmani
(74) *Attorney, Agent, or Firm* — Casimir Jones, SC

(57) ABSTRACT

This invention is in the field of medicinal chemistry. In particular, the invention relates to a new class of small-molecules having pyrazolopyridine structure which function as inhibitors of Mcl-1 protein, and their use as therapeutics for the treatment of cancer and other diseases.

4 Claims, 9 Drawing Sheets

(56) References Cited

OTHER PUBLICATIONS

Misra R. N. et al., "1H-Pyrazolo[3,4-b]pyridine inhibitors of cyclin-dependent kinases." Bioorg Med Chem Lett 2003, 13, 1133-6.
Miyamoto Y, et al., "Immunohistochemical Analysis of Bcl-2, Bax, Bcl-X, and Mcl-1 Expression in Pancreatic Cancers." Oncology. 1999;56:73-82.
Muilenburg et al., "Targeting Bcl-2-mediated cell death as a novel therapy in pancreatic cancer." J Surg Res., 2010, 163(2):276-81.
Neres J., et al., "Non-nucleoside inhibitors of BasE, an adenylating enzyme in the siderophore biosynthetic pathway of the opportunistic pathogen Acinetobacter baumannii." J Med Chem 2013, 56, 2385-405.
Nikolovska-Coleska, Z. et al., "Development and optimization of a binding assay for the XIAP BIR3 domain using fluorescence polarization." Anal Biochem 2004, 332, 261-73.
Nikolovska-Coleska, Z., 102nd AACR Annual Meeting 2011, poster and presentation, Abstract Only.
Oltersdorf T. et al., "An inhibitor of Bcl-2 family proteins induces regression of solid tumours." Nature. 2005 435 (7042):677-81.
Petros A. et al., "Discovery of a potent and selective Bcl-2 inhibitor using SAR by NMR." Bioorg Med Chem Lett. 2010, 20(22):6587-91.
PubChem's BioAssay Database under AID 1417.
Ren Ln, et al., "Endocrine glands-derived vascular endothelial growth factor protects pancreatic cancer cells from apoptosis via upregulation of the myeloid cell leukemia-1 protein." Biochem Biophys Res Commun. 2009;386:35-9.
Schniewind B, et al., "Resistance of pancreatic cancer to gemcitabine treatment is dependent on mitochondria-mediated apoptosis." Int J Cancer. 2004;109:182-8.
Sercel A. D., et al., "Synthetic Communications: an International Journal for Rapid Communication of Synthetic Organic Chemistry." Synthetic Communications 2007, 37, 4199-4208.
Tse C, et al., "ABT-263: a potent and orally bioavailable Bcl-2 family inhibitor." Cancer Res. 2008;68:3421-8.
Van Delft Mf, et al., "The BH3 mimetic ABT-737 targets selective Bcl-2 proteins and efficiently induces apoptosis via Bak/Bax if Mcl-1 is neutralized." Cancer Cell. 2006;10:389-99.
Volochnyuk D. M., et al., "Approach to the library of fused pyridine-4-carboxylic acids by Combes-type reaction of acyl pyruvates and electron-rich amino heterocycles." J Comb Chem 2010, 12, 510-7.
Wei Sh, et al., "Inducing apoptosis and enhancing chemosensitivity to gemcitabine via RNA interference targeting Mcl-1 gene in pancreatic carcinoma cell." Cancer Chemother Pharmacol. 2008;62:1055-64.
Wertz Ie et al., "Sensitivity to antitubulin chemotherapeutics is regulated by MCL1 and FBW7." Nature. 2011, 471 (7336):110-4.
Zhou P, et al., "Mcl-1, a Bcl-2 family member, delays the death of hematopoietic cells under a variety of apoptosis-inducing conditions." Blood. 1997;89:630-43.
International Search Report and Written Opinion, International Application No. PCT/US2015/024231, mailed Oct. 1, 2015, 10 pages.
PUBCHEM-CID 3316323 Create Date—Jul. 9, 2005.

* cited by examiner

SMALL MOLECULE INHIBITORS OF MCL-1 AND USES THEREOF

STATEMENT REGARDING FEDERALLY SPONSORED RESEARCH OR DEVELOPMENT

This invention was made with government support under CA149442, CA158976 and NS056915 awarded by the National Institutes of Health. The government has certain rights in the invention.

FIELD OF THE INVENTION

This invention is in the field of medicinal chemistry. In particular, the invention relates to a new class of small-molecules having a pyrazolopyridine structure which function as inhibitors of Mcl-1 protein, and their use as therapeutics for the treatment of cancer and other diseases.

INTRODUCTION

A hallmark of cancer cells is defects in the apoptotic cell death program (see, e.g., Hanahan D, et al., Cell. 2000; 100: 57-70). The broad resistance of many types of cancers to existing chemotherapeutic agents and radiation therapy is due, in large part, to defects in apoptotic signaling pathways.

Improved methods for preventing and/or repairing defects in apoptotic signaling pathways are needed.

SUMMARY OF THE INVENTION

Mcl-1 is a potent anti-apoptotic protein and an important survival factor for many human cancers, including breast, pancreatic, colon, lung, ovarian, prostate, melanoma, multiple myeloma, and acute myeloid leukemia. Mcl-1 is highly amplified in human cancer and its overexpression has been associated with tumor initiation, progression and resistance to current anticancer therapies. Recent independent studies using a genetic approach to down-regulation of Mcl-1 provided a significant proof-of-concept that selective, small-molecule Mcl-1 inhibitors may have potential as a new treatment for human cancers by overcoming the apoptosis resistance of cancer cells to current therapeutic agents. Mcl-1 is a homologous protein related to other anti-apoptotic proteins such as Bcl-2 and Bcl-$x_L$, but it has a distinctly different structure and exhibits selective binding to the pro-apoptotic BH3-only proteins. This suggests that specific targeting of the Mcl-1 protein is possible and that drugs specific to Mcl-1 can be developed.

Applying a high throughput screening (HTS) approach, experiments conducted during the course of developing embodiments for the present invention identified and validated a new class of small-molecules having pyrazolopyridine structure which function as inhibitors of Mcl-1 protein. Indeed, a class of small-molecule Mcl-1 inhibitors based on a HTS lead 1

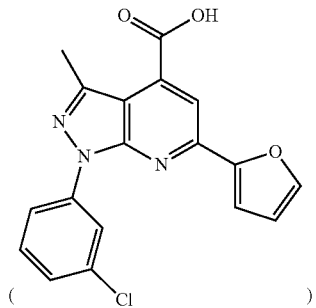 [SMILES: Cc1nn(-c2cccc(Cl)c2)c2nc(-c3ccco3)cc(C(=O)O)c12]

was developed. Systematic removal of side chains of 1 and detailed NMR analysis of the obtained fragments mapped the binding site of this class of inhibitors in the BH3-binding groove of Mcl-1. The structure-based lead optimization was guided by computational modeling supported by NMR and X-ray studies. Utilizing an efficient synthetic route, a series of analogs were synthesized and their binding affinity was determined by FP-based assay. A potent analog 57 with an $K_i$ of 127 nM and 21-fold improvement in binding potency compared to lead compound 1 was developed. Selectivity profile of analog 57 further illustrated that it inhibited Mcl-1 most potently, with 15 fold decrease binding affinity to Bcl-2, and no binding to Bcl-xL up to 20 µM. Table 1 shows various pyrazolopyridine compounds with their $IC_{50}$ and $K_i$ values for binding to Mcl-1.

As such, the present invention provides a new class of small-molecules having a pyrazolopyridine structure which function as inhibitors of Mcl-1 protein, and as therapeutics for the treatment of cancer and other diseases.

Accordingly, the present invention contemplates that exposure of animals (e.g., humans) suffering from cancer (e.g., and/or cancer related disorders) to therapeutically effective amounts of drug(s) having a pyrazolopyridine structure (e.g., small molecules having a pyrazolopyridine structure) that inhibit the activity of Mcl-1 will inhibit the growth of cancer cells or supporting cells outright and/or render such cells as a population more susceptible to the cell death-inducing activity of cancer therapeutic drugs or radiation therapies. In some embodiments, the inhibition of Mcl-1 activity occurs through, for example, inhibiting the interaction between Mcl-1 and Bak and/or Bax. In some embodiments, the inhibition of Mcl-1 activity occurs through, for example, binding the BH3 binding groove of Mcl-1. The present invention contemplates that inhibitors of Mcl-1 activity satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain pyrazolopyridine compounds function as inhibitors of Mcl-1 protein, and serve as therapeutics for the treatment of cancer and other diseases. Thus, the present invention relates to pyrazolopyridine compounds useful for inhibiting Mcl-1 activity (e.g., thereby facilitating cell apoptosis), and increasing the sensitivity of cells to inducers of apoptosis and/or cell cycle arrest. Certain pyrazolopyridine compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, pyrazolopyridine compounds encompassed within any Formulas I, II, III or IV are provided:

Formula I

Formula II

Formula III

Formula IV including pharmaceutically acceptable salts, solvates, and/or prodrugs thereof.

Formulas I, II, III or IV is not limited to a particular chemical moiety for R1, R2, R3, R4, R5 and R6. In some embodiments, the particular chemical moiety for R1, R2, R3, R4, R5 and R6 independently include any chemical moiety that permits the resulting compound to bind with an Mcl-1 protein.

In some embodiments, R1 is a substituted or non-substituted aryl moiety. In some embodiments, R1 is a substituted or non-substituted alkaryl moiety. In some embodiments, R1 is selected from

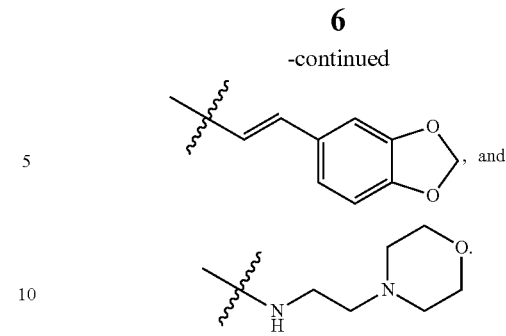

In some embodiments, R2 is hydrogen.

In some embodiments, R3 is an acid moiety. In some embodiments, R3 is an ester moiety. In some embodiments, R3 is hydrogen. In some embodiments, R3 is $CH_3$. In some embodiments, R3 is OH. In some embodiments, R3 is a carboxylic acid bioisostere moiety. In some embodiments, R3 is selected from H, OH, $OCH_3$, $OCH_2CH_3$, COOH, $COOCH_3$, $COOCH_2CH_3$,

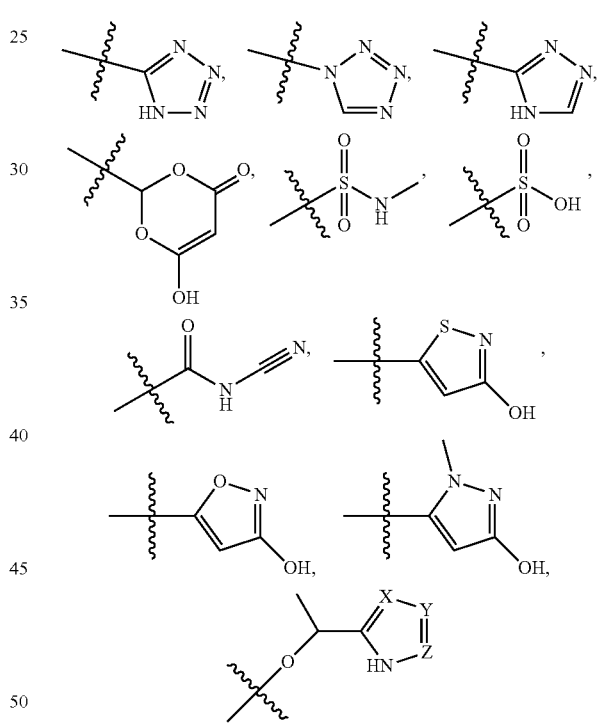

(wherein X, Y, Z are independently N, C or CO),

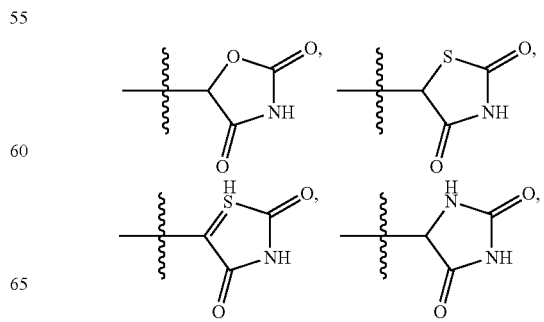

In some embodiments, R1 is hydrogen.

In some embodiments, R2 is an alkyl moiety, an alkylenyl moiety, an alkynyl moiety, an aminoakyl moiety, a phenethyl moiety, a styryl moiety, a phenylethynyl moiety, a halogen moiety, or a (furan-2-ylmethyl)amino moiety. In some embodiments, R2 is selected from halogen (e.g., Chlorine),

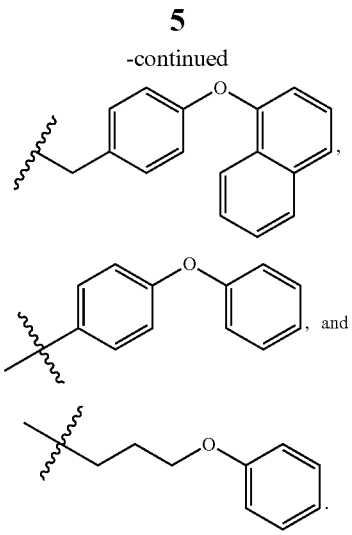

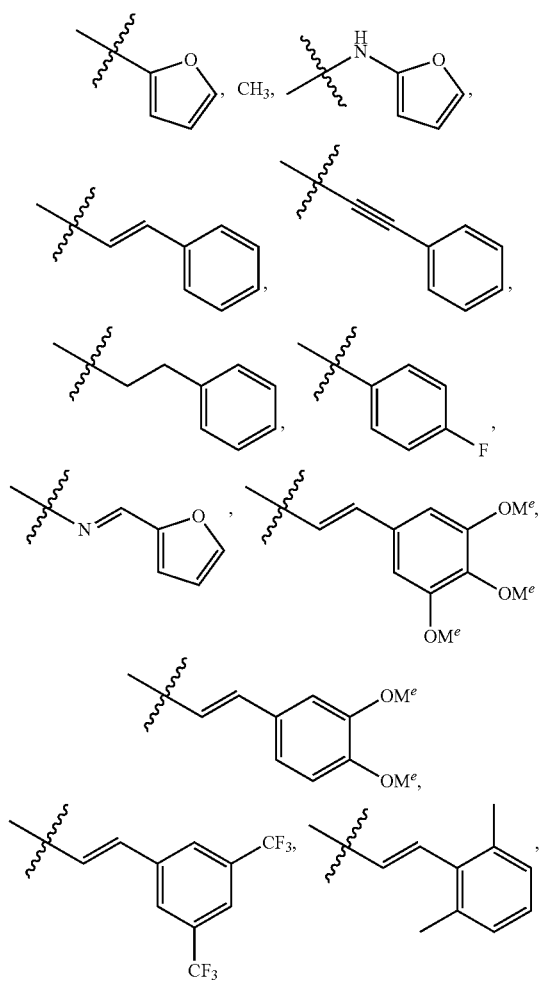

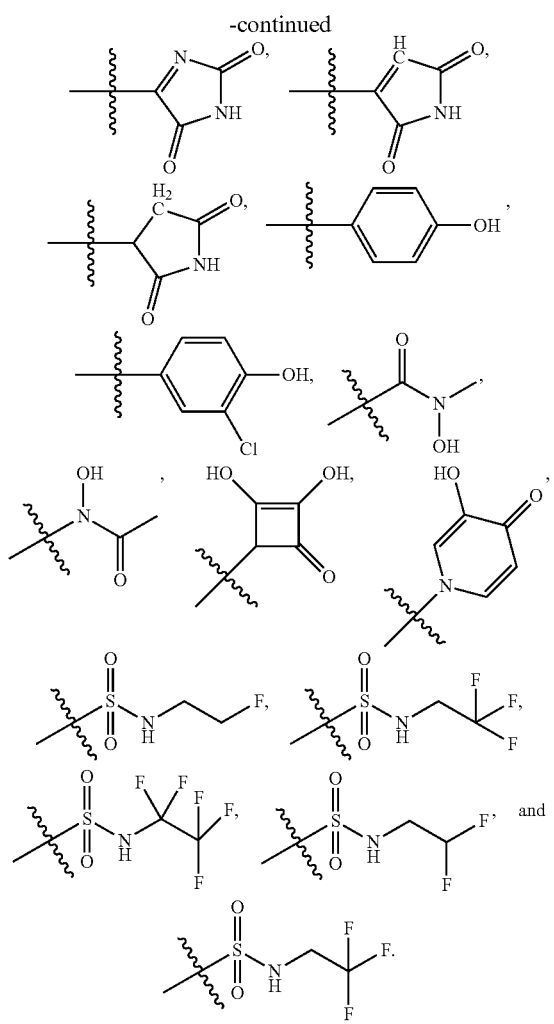
In some embodiments, R4 is an optionally substituted alkyl moiety, a cycloalkyl moiety, an aryl moiety, or a heterocyclic moiety. In some embodiments, R4 is selected from OH, hydrogen,
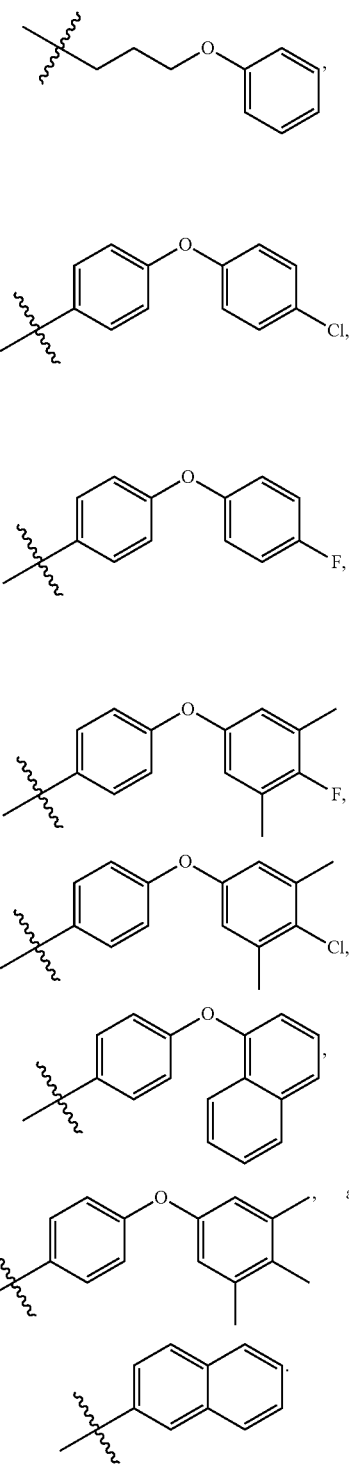
In some embodiments, R5 is selected from
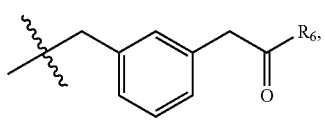

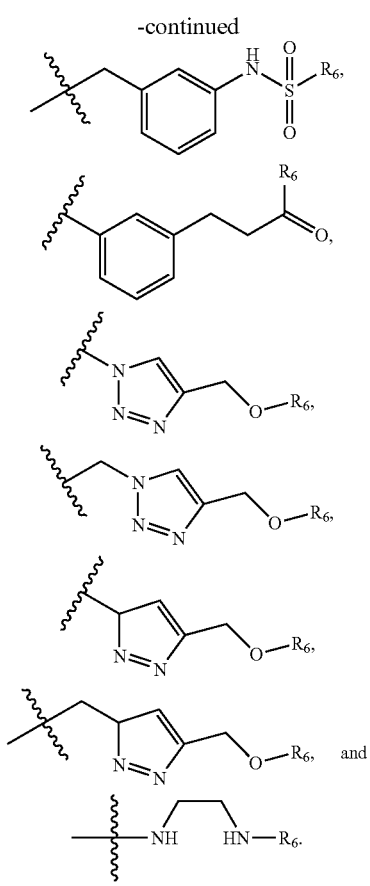

In some embodiments, R6 is absent. In some embodiments, R6 is selected from the group consisting of

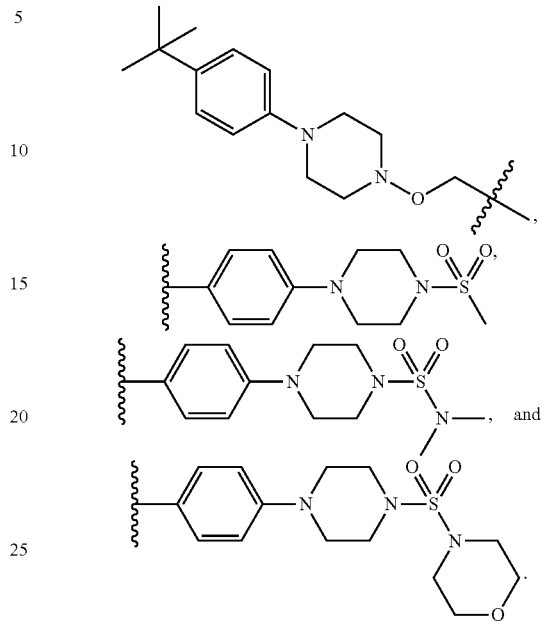

Table 1 show binding affinities (IC$_{50}$ values were determined with fluorescence polarizing binding assay) for various compounds encompassed and inhibition against Mcl-1 within Formulas I, II, III and IV.

In some embodiments, the following compounds are contemplated for Formulas I, II, III and IV:

-continued
(compound 5)
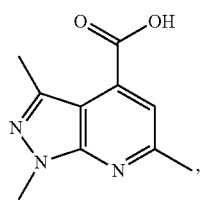
(compound 6)
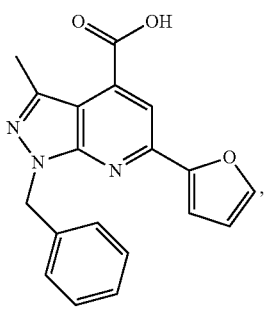
(compound 7)
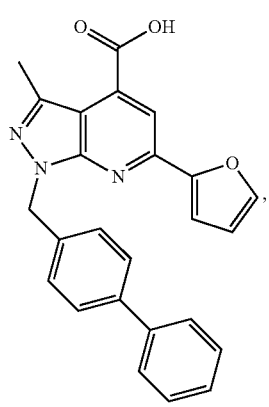
(compound 8)
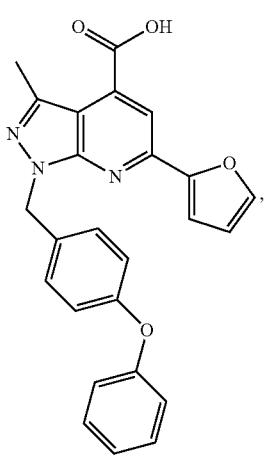
(compound 9)
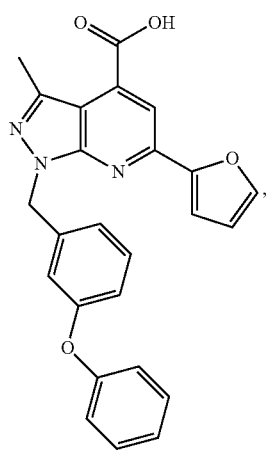
(compound 10)
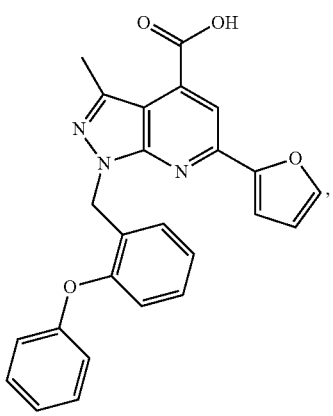
(compound 11)
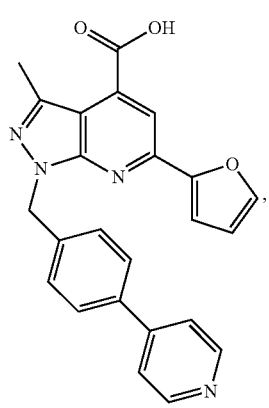
(compound 12)
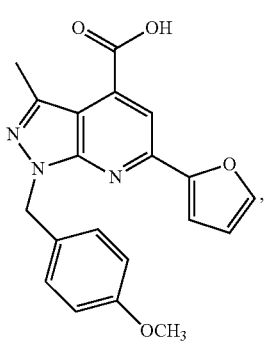

(compound 13)
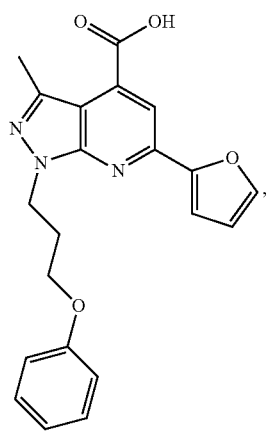
(compound 14)
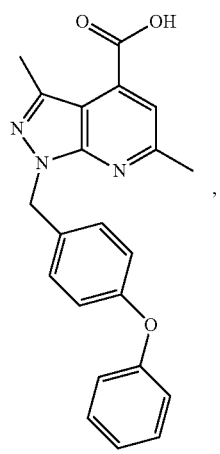
(compound 15)
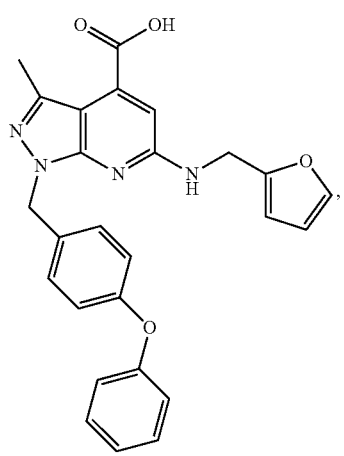
(compound 16)
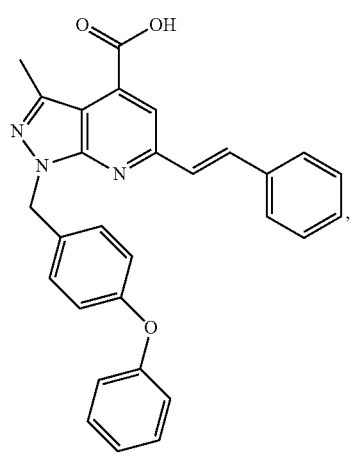
(compound 17)
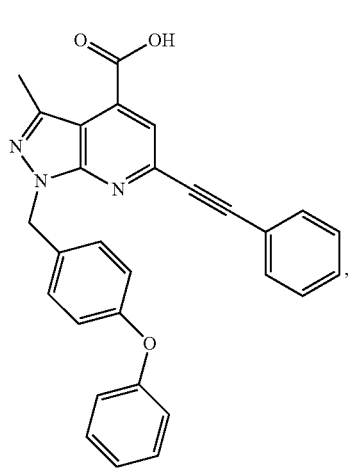
(compound 18)
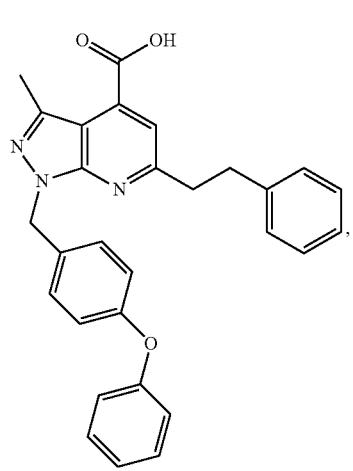

-continued
(compound 19)
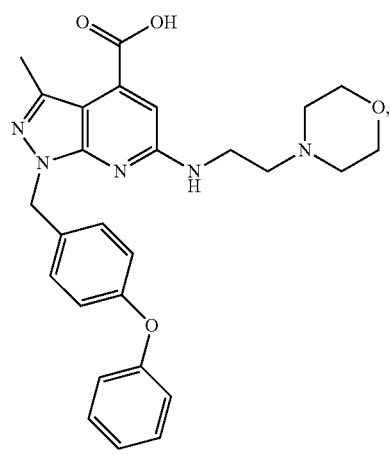
(compound 35)
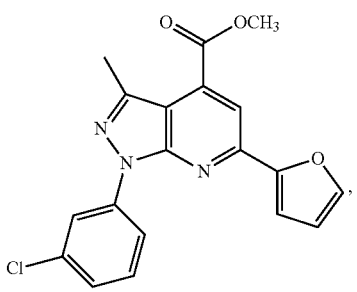
(compound 36)
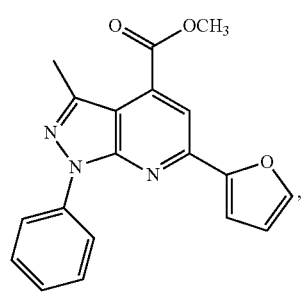
(compound 37)
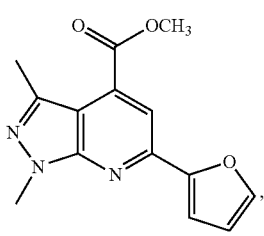
(compound 38)
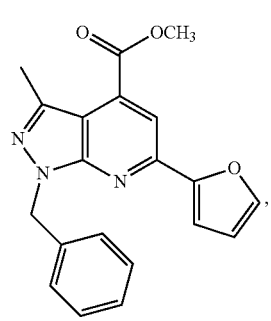
(compound 39)
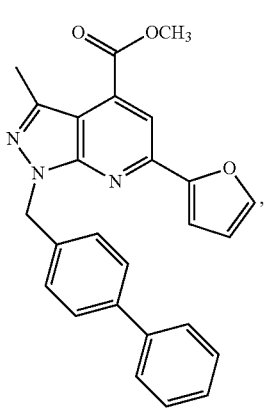
(compound 40)
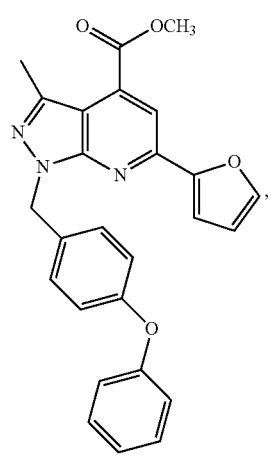
(compound 41)
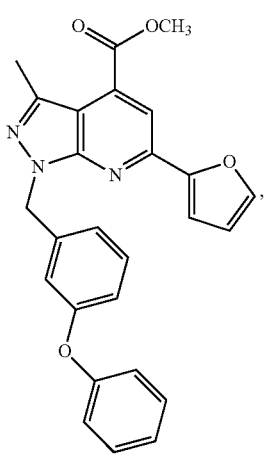

-continued
(compound 42)
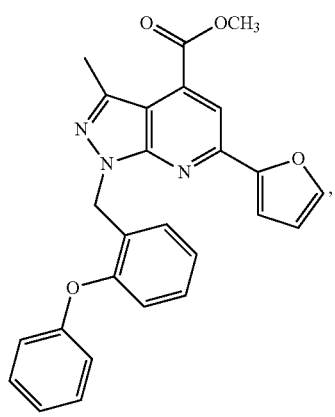
(compound 43)
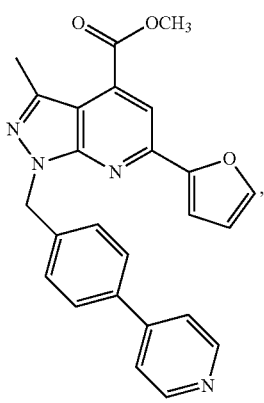
(compound 44)
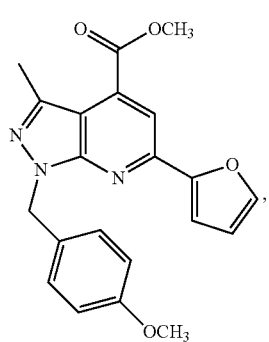
(compound 45)
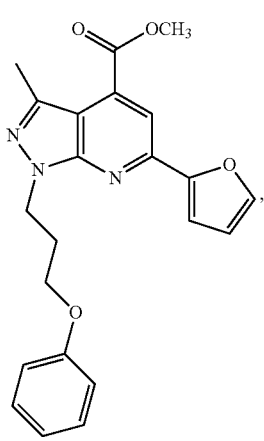
(compound 46)
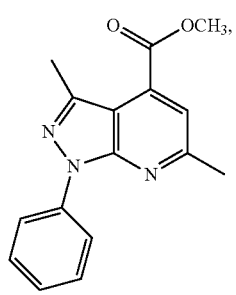
(compound 47)
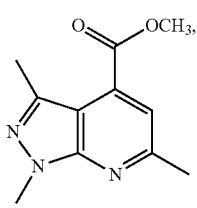
(compound 48)
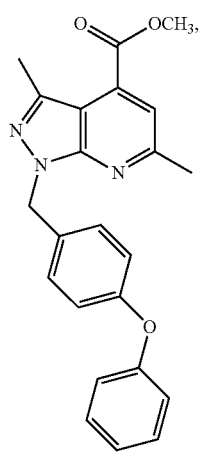
(compound 49)
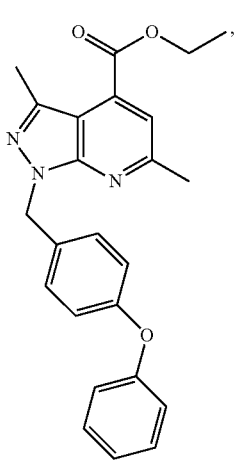

(compound 50)
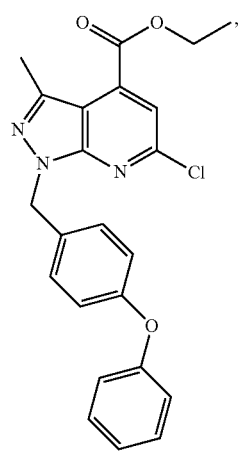
(compound 51)
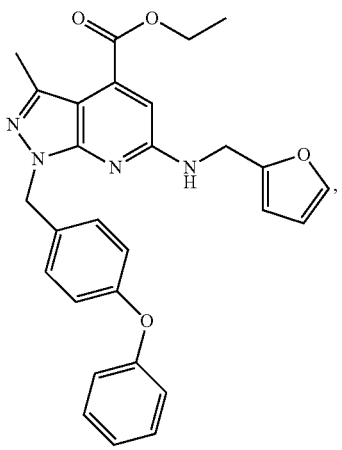
(compound 52)
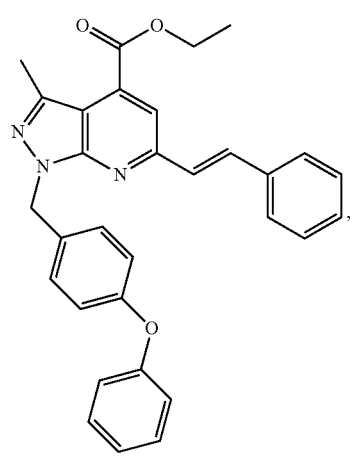
(compound 53)
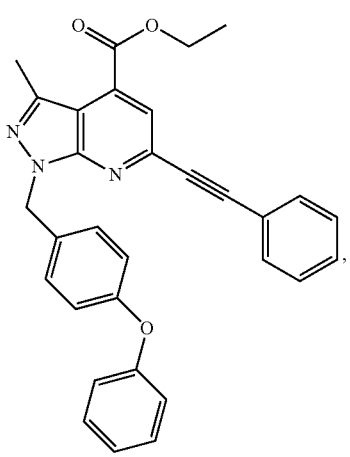
(compound 54)
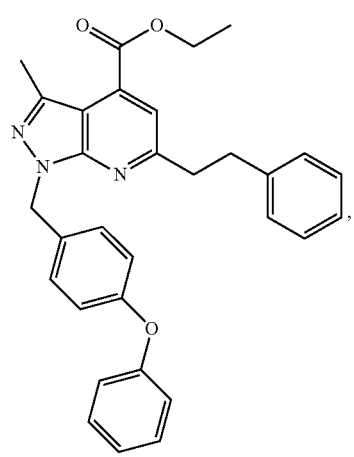
(compound 55)
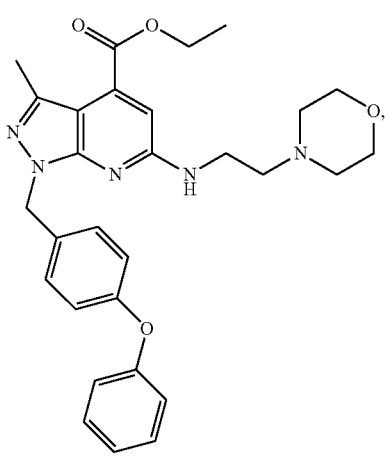

-continued
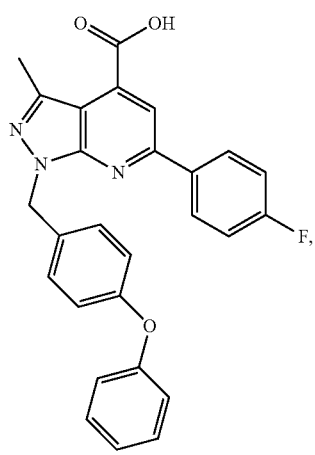
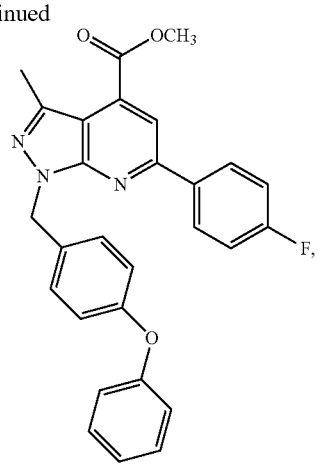
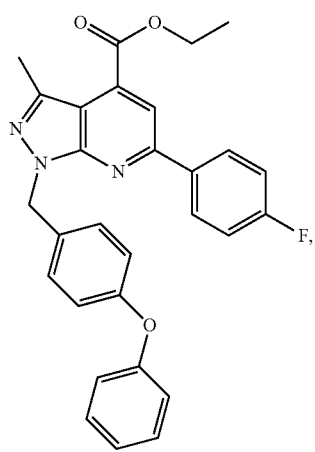
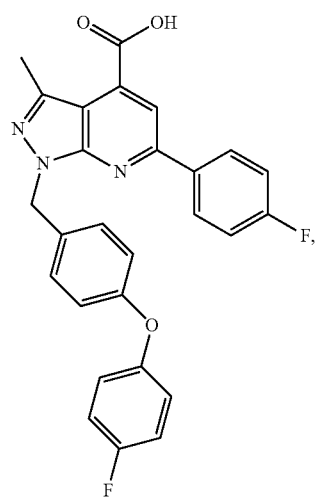
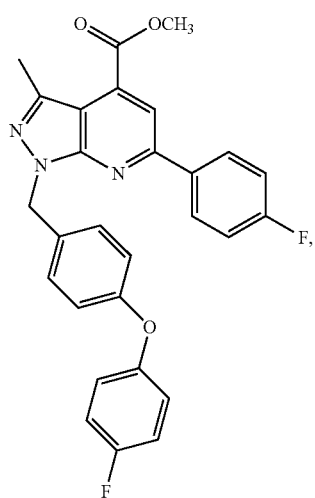
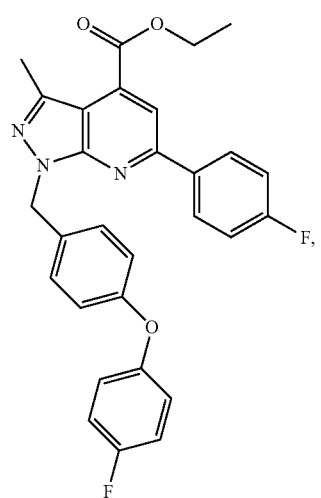

-continued
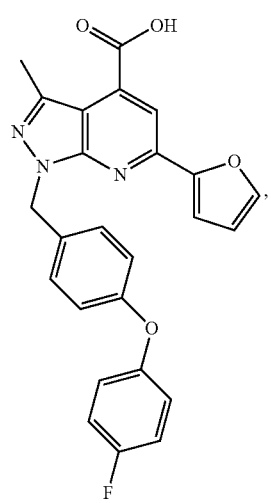
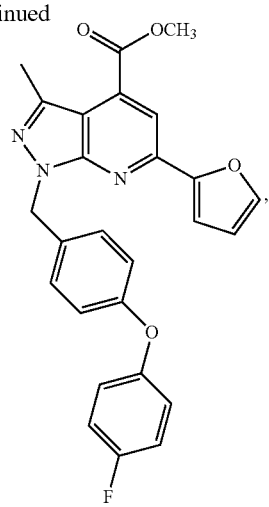
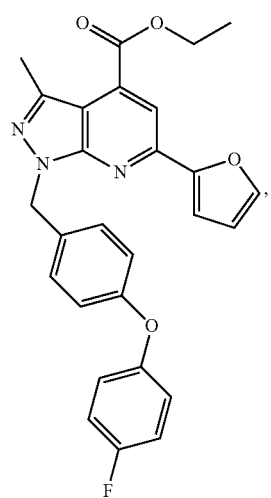
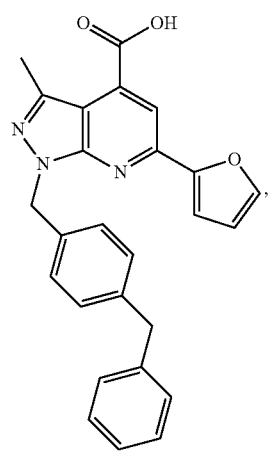
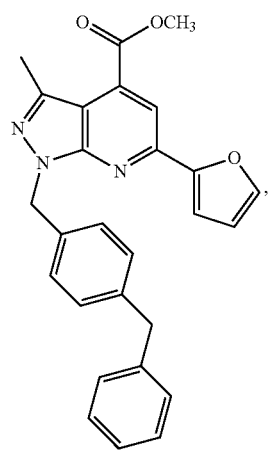
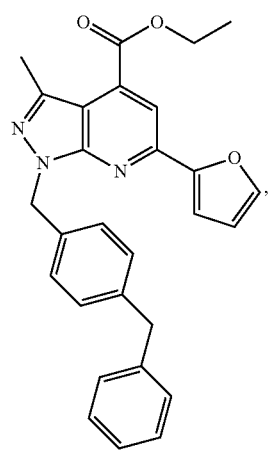

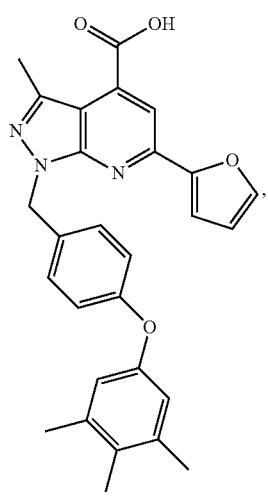
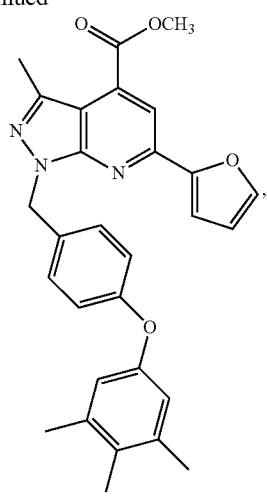
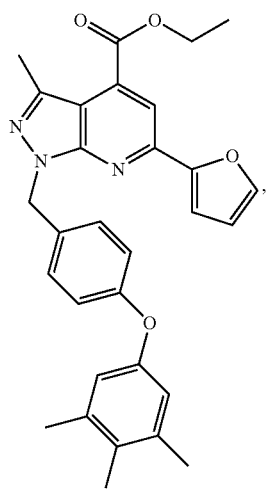
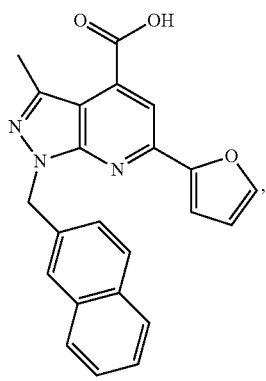
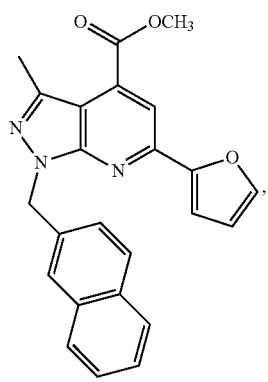
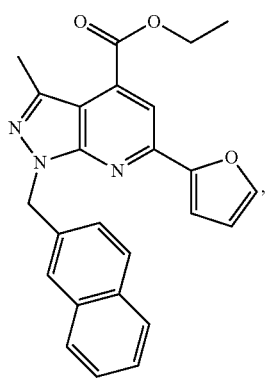

-continued
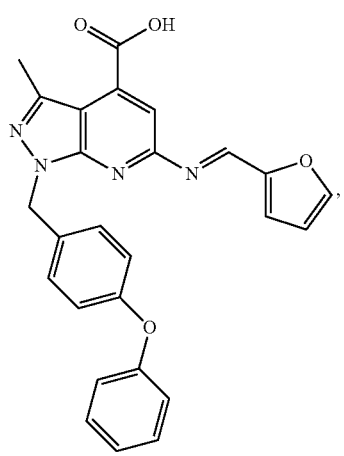
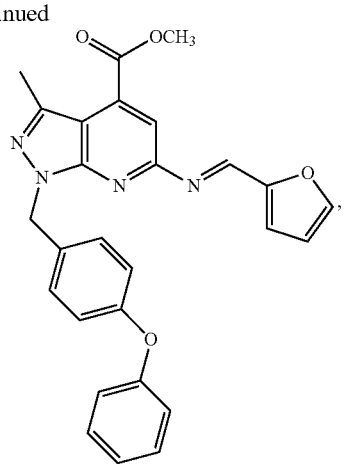
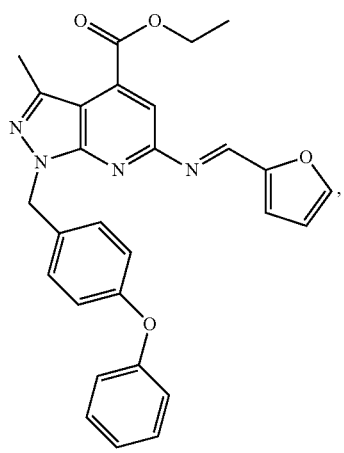
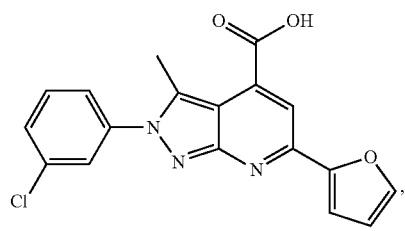
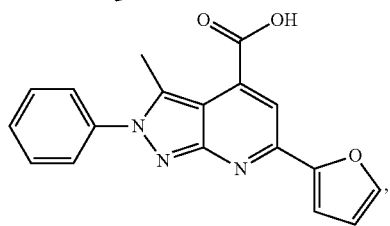
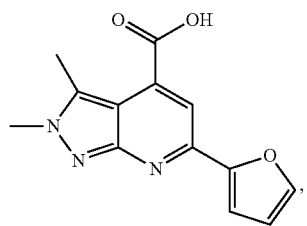
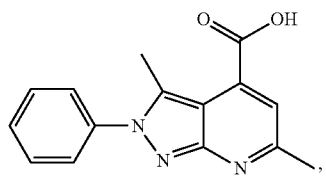
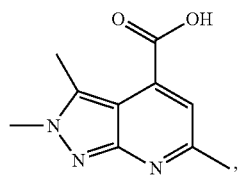
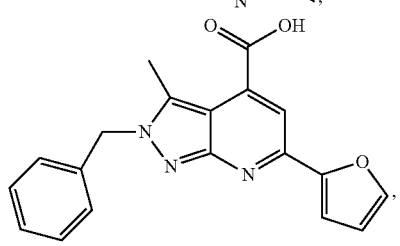
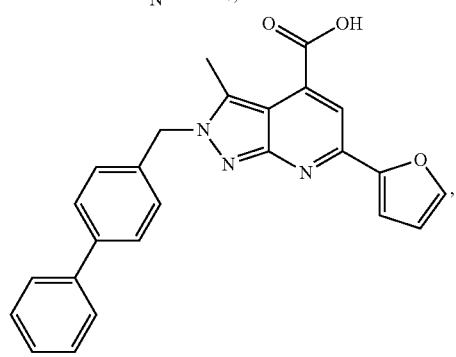

-continued
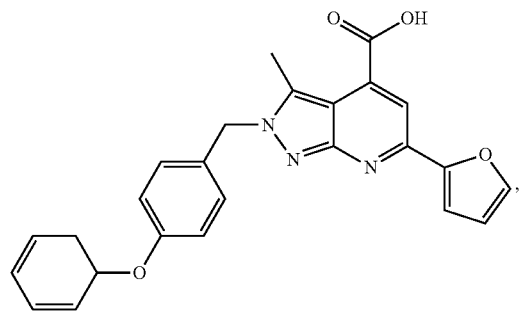
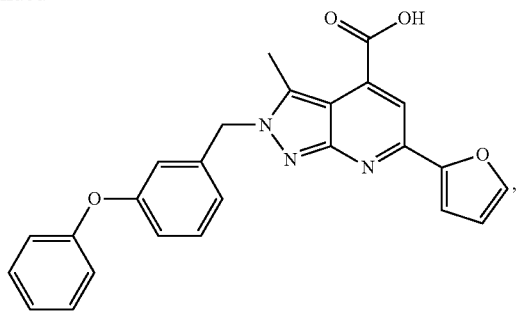
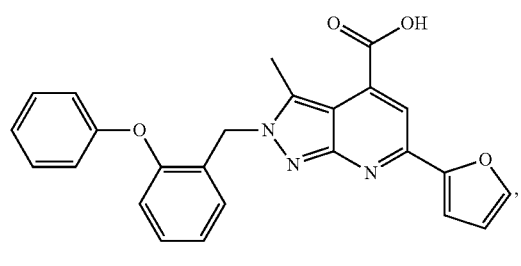
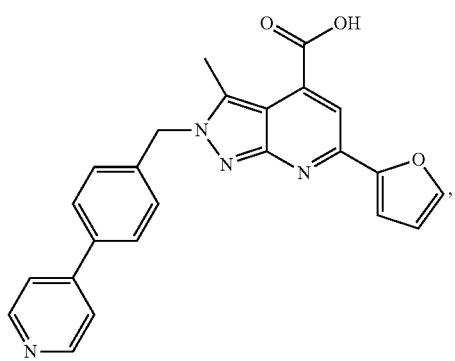
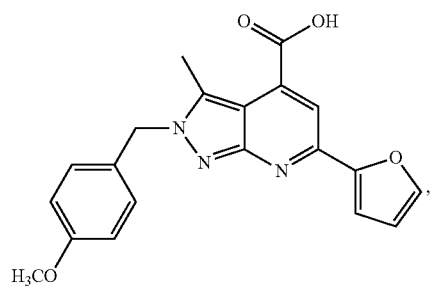
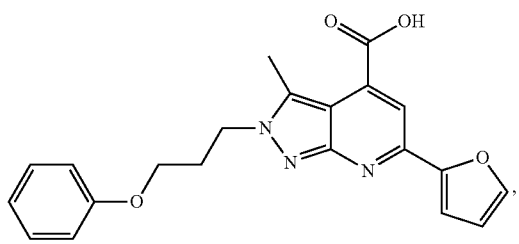
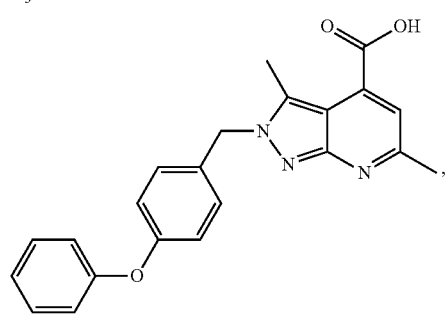
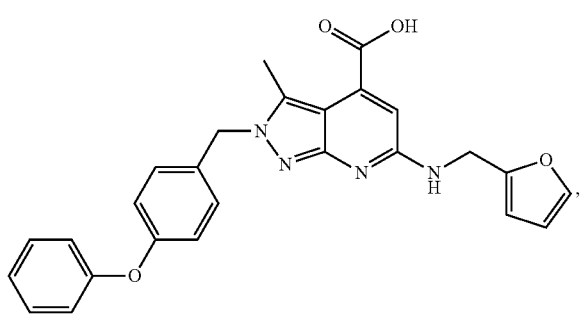
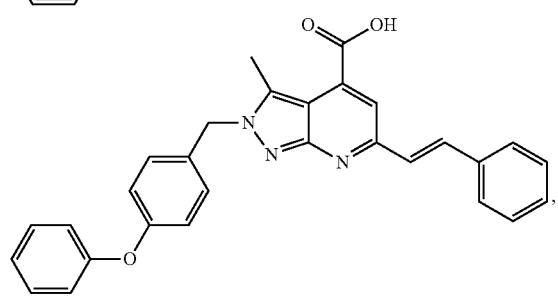
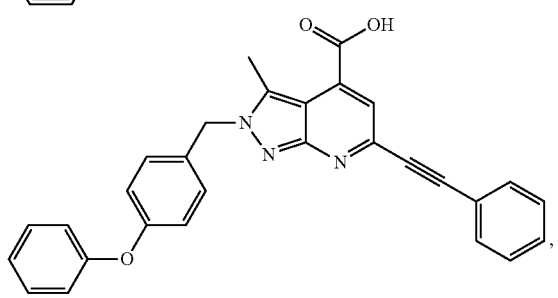

-continued
31
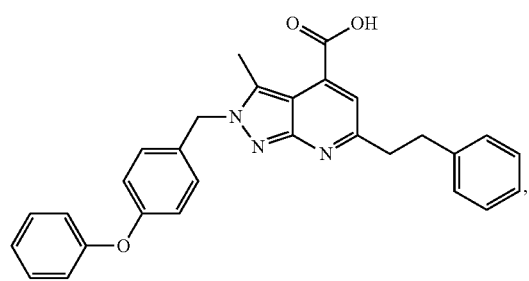
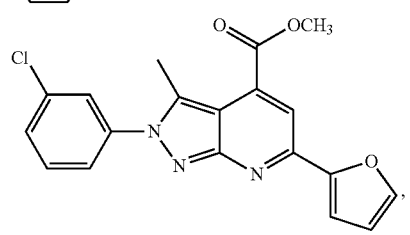
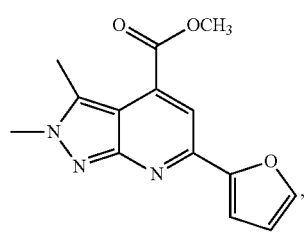
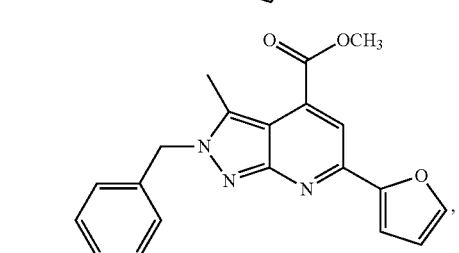
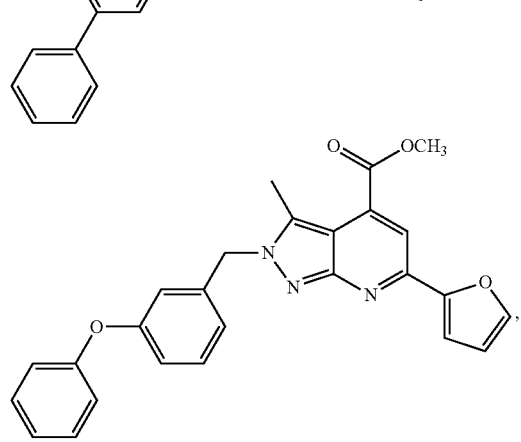
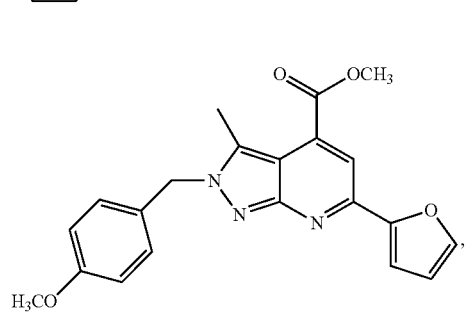
32
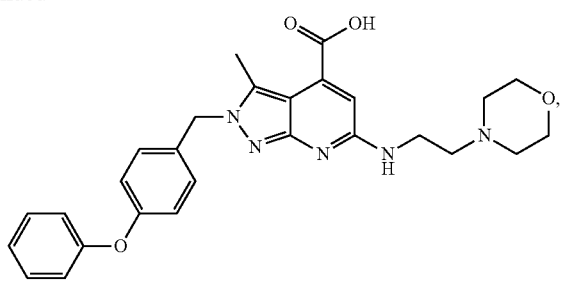
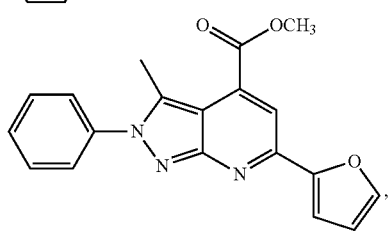
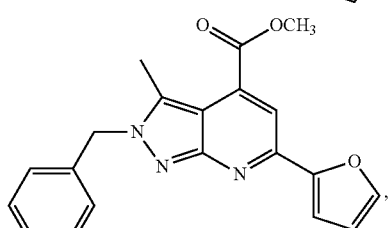
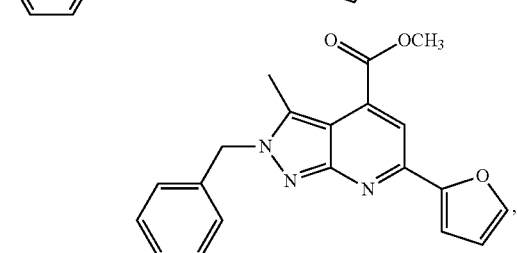
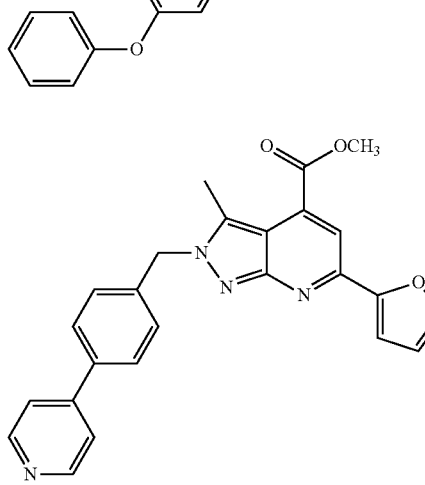
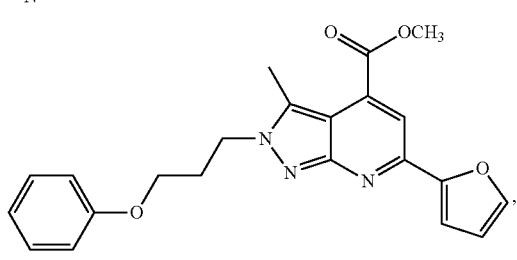

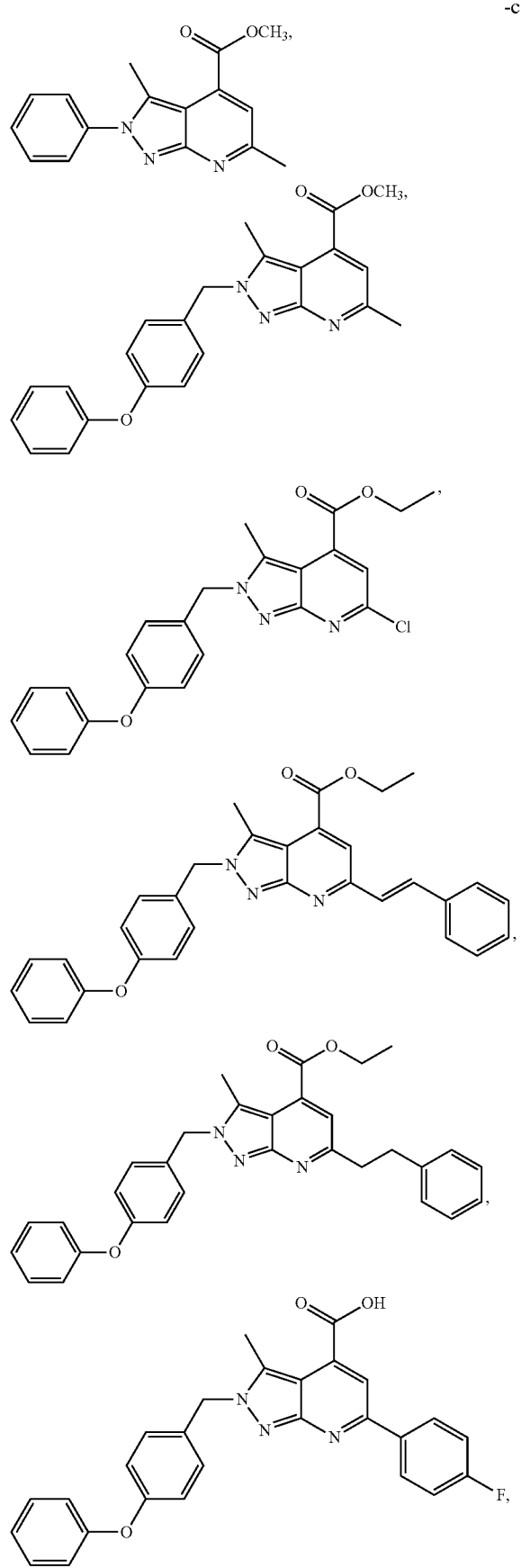
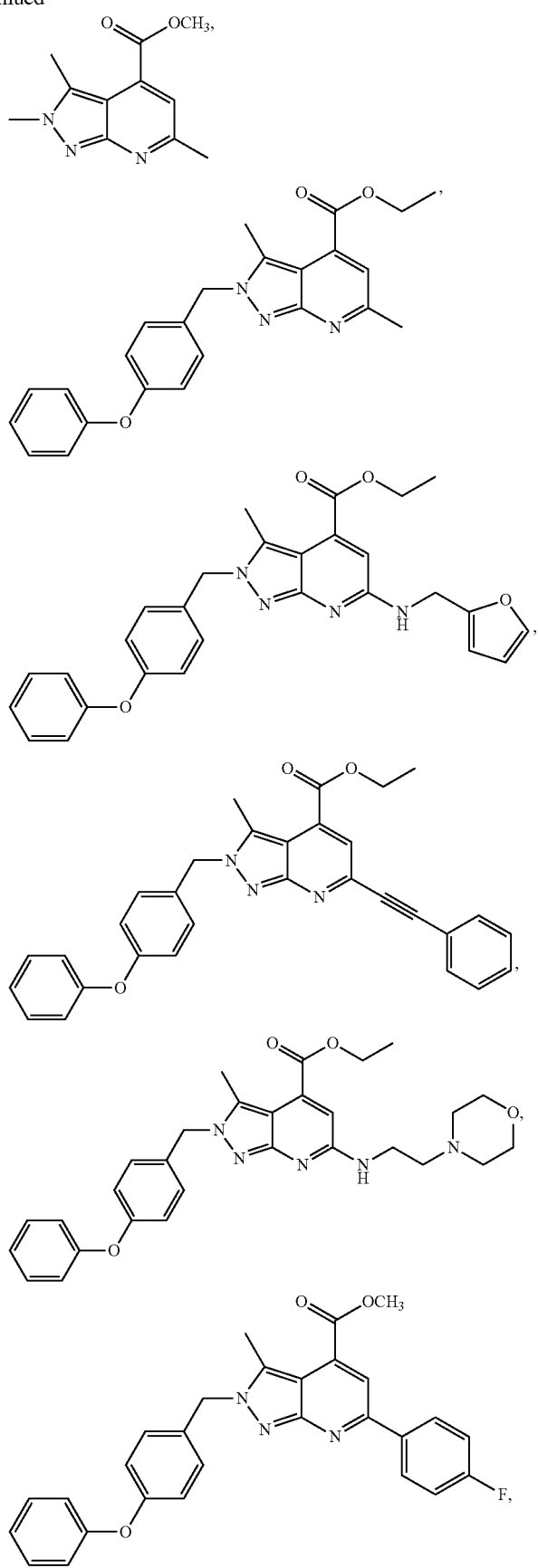

-continued
35
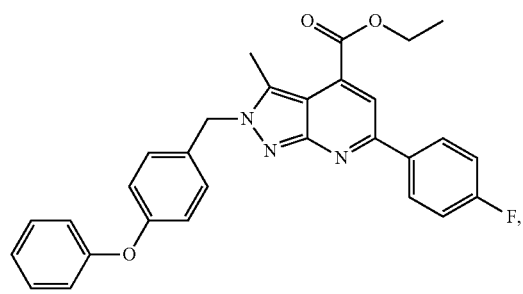
36
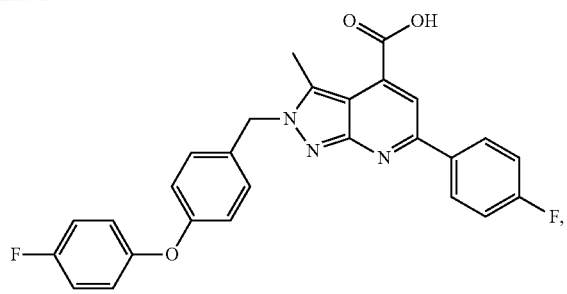
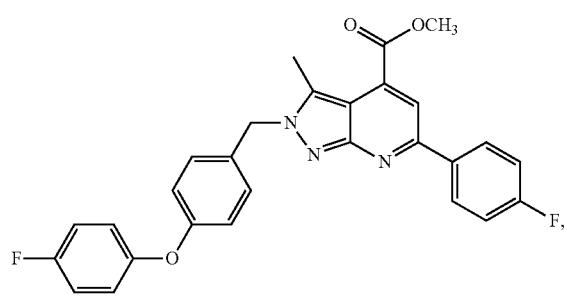
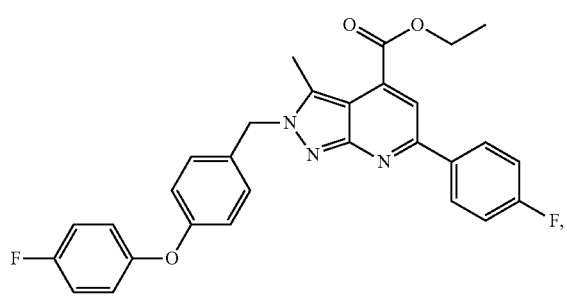
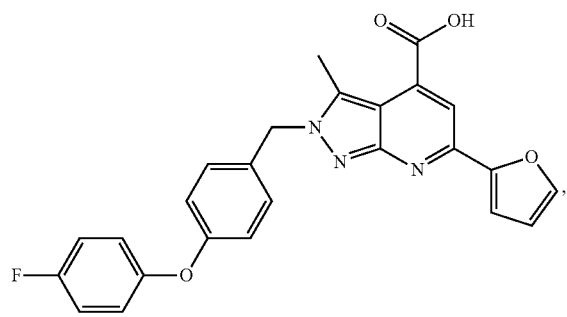
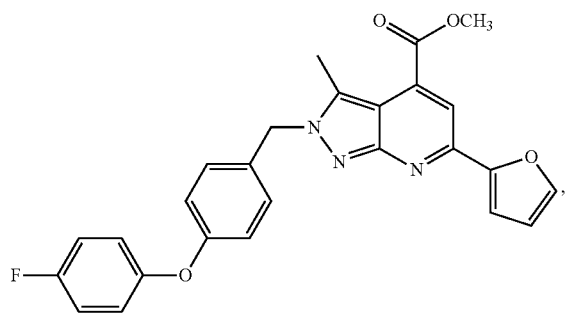
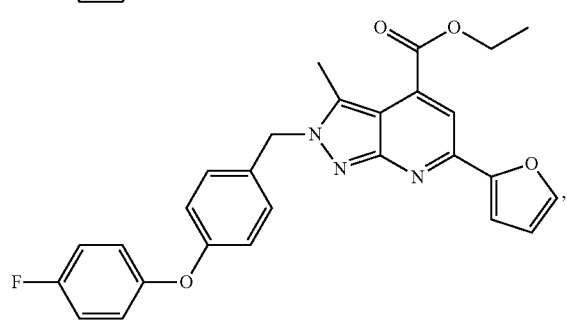
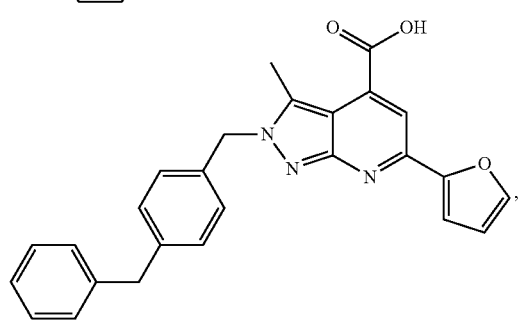
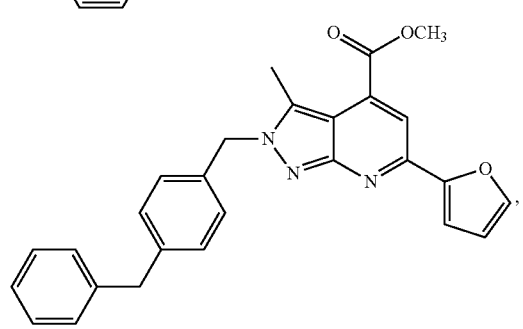
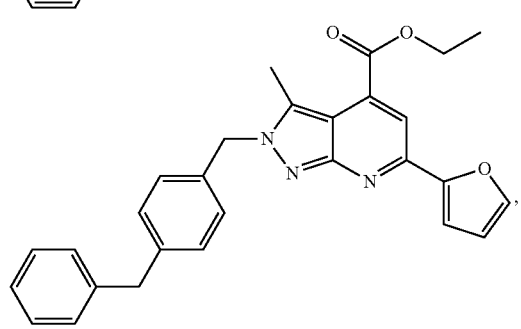

-continued
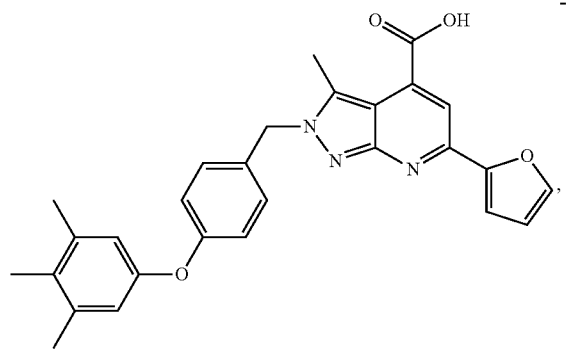
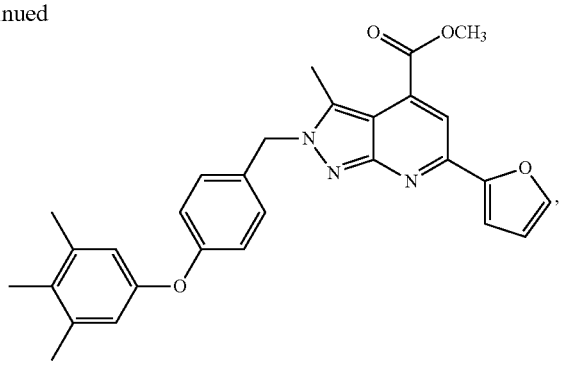
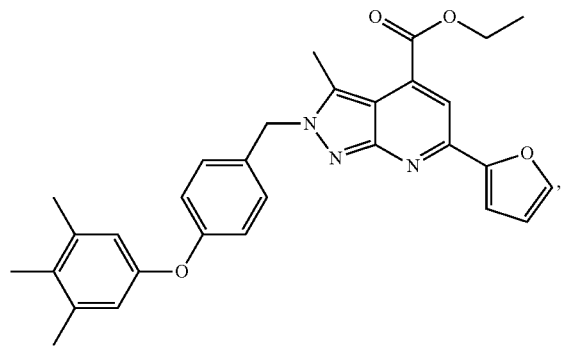
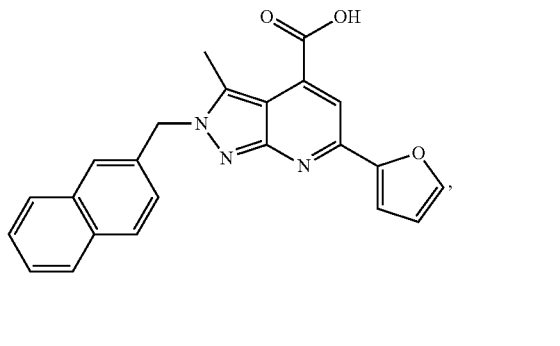
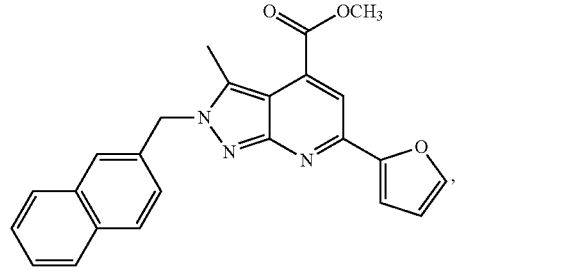
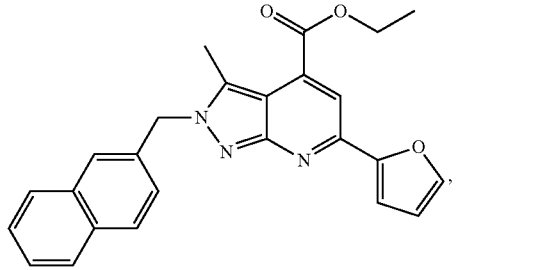
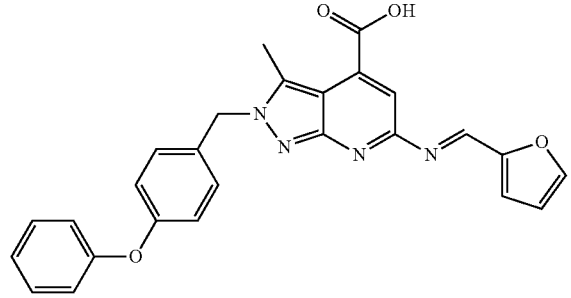
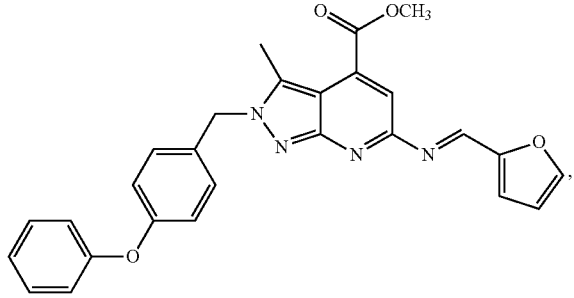
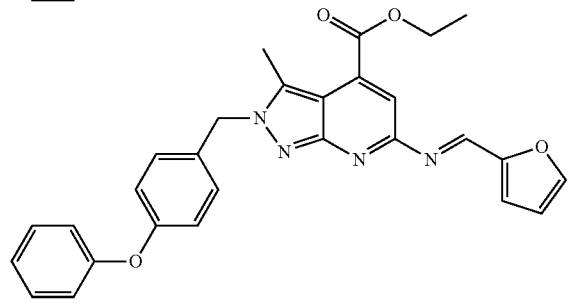
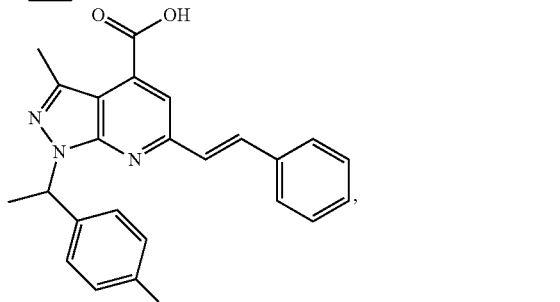

39
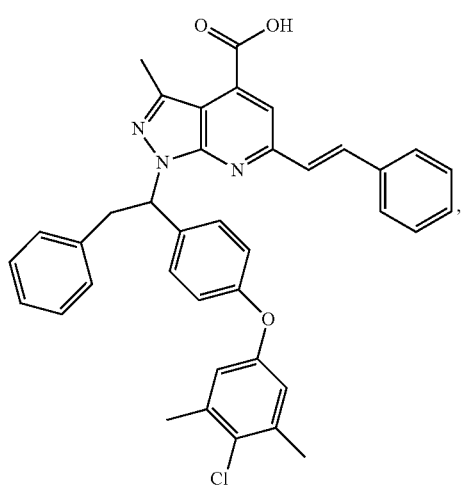
40
-continued
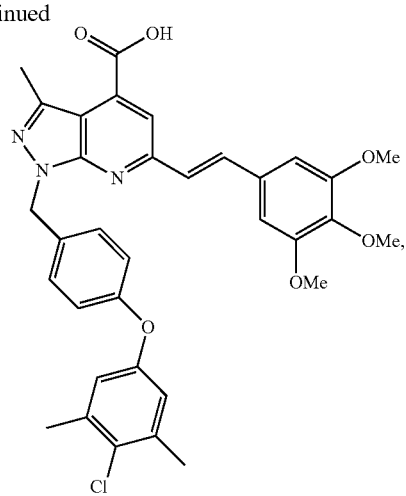
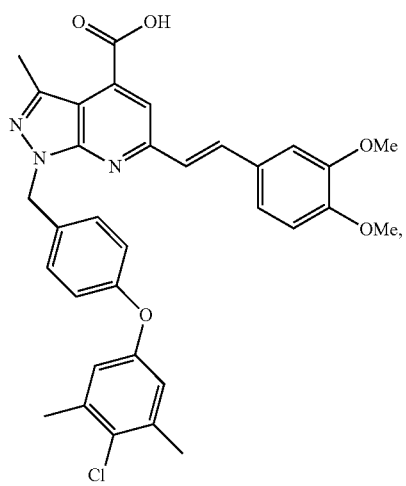
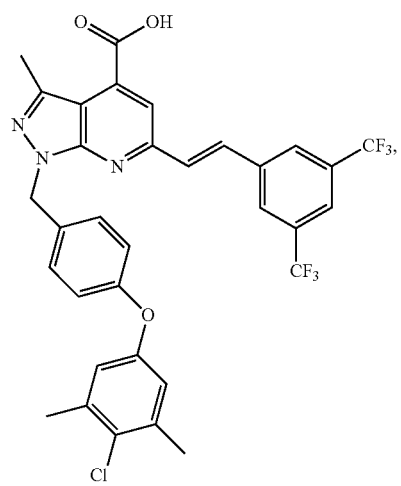
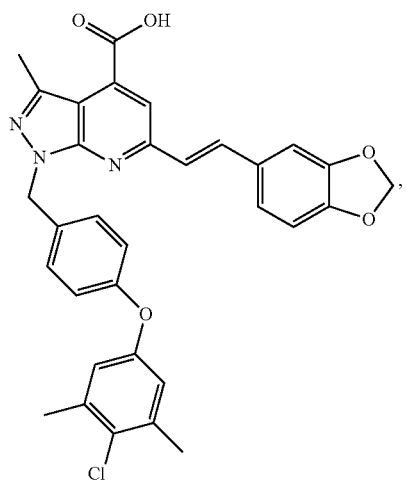

-continued

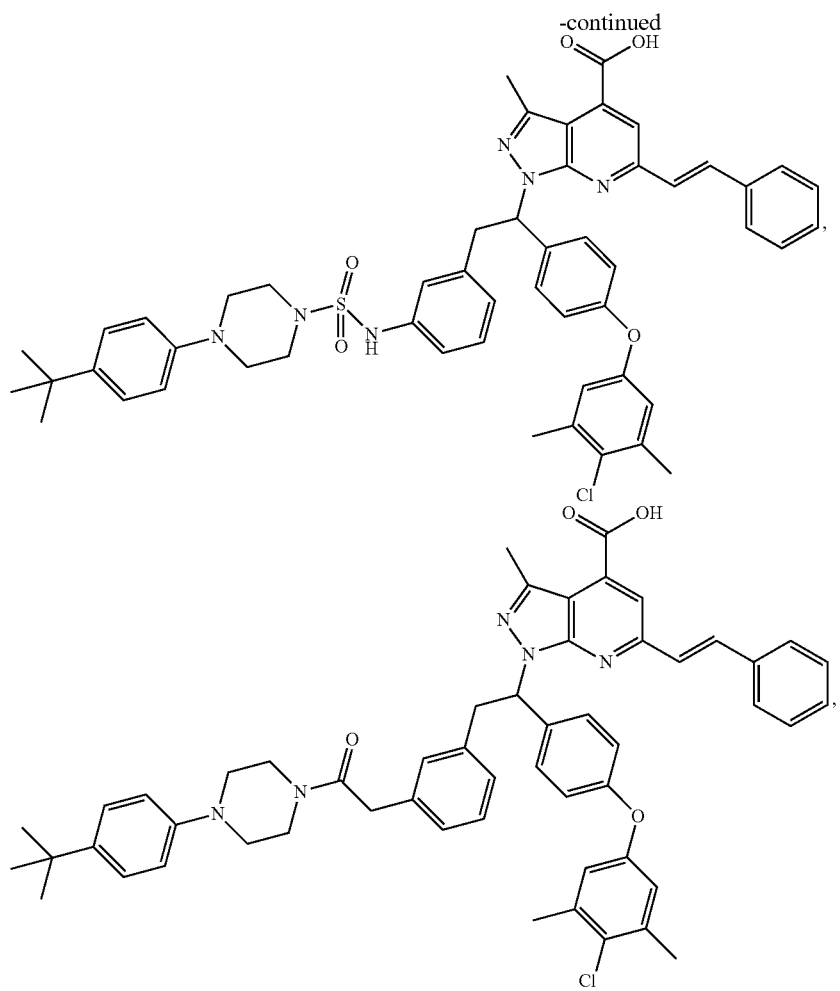

or a pharmaceutically acceptable salt, solvate, or prodrug thereof.

The invention further provides processes for preparing any of the compounds of the present invention through following at least a portion of the techniques recited in Example 5.

The invention also provides the use of compounds to induce cell cycle arrest and/or apoptosis in cells containing functional Mcl-1 proteins. The invention also relates to the use of compounds for sensitizing cells to additional agent(s), such as inducers of apoptosis and/or cell cycle arrest, and chemoprotection of normal cells through the induction of cell cycle arrest prior to treatment with chemotherapeutic agents.

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In certain embodiments, the cancer is multiple myeloma, acute myeloid leukemia, melanoma, breast cancer, and/or pancreatic cancer. In other embodiments, the compounds can be used to treat hyperproliferative diseases characterized by expression of functional Mcl-1 and/or Mcl-1 related proteins.

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., anticancer agents or apoptosis-modulating agents.

Applying an integrated screening approach through combining high throughput and virtual screenings, experiments conducted during the course of developing embodiments for the present invention identified several novel chemical classes of small-molecules having a pyrazolopyridine structure as Mcl-1 inhibitors. Compound 1

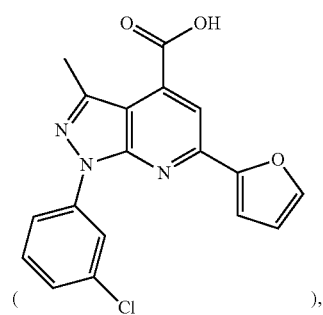 [SMILES: Cc1nn(-c2cccc(Cl)c2)c2nc(-c3ccco3)cc(C(=O)O)c12]

(                                                        ), for example, with pyrazolopyridine scaffold was selected as a promising high throughput lead for medicinal chemistry efforts. An efficient synthetic route was developed and a focused library was generated. Using chemical shift mapping the binding of the lead compound 1 was characterized and confirmed to be the BH3 binding pocket of Mcl-1. This chemical shift mapping was further applied for the rational design of new analogs and the structure-based lead optimization was guided by computational modeling and crystallographic studies. Structure-activity relationship was established utilizing two different competitive platforms of fluorescent polarization and surface plasmon resonance, and confirmed by heteronuclear single quantum coherence NMR spectroscopy (HSQC NMR spectroscopy). The binding of this class of compounds was improved more than twenty fold in comparison with the lead compound 1. In vitro binding, functional and cell-based assays were performed in order to determine respective selectivity profiles against five members of the Bcl-2 family.

Further chemical modifications to compound 1 led to development of several compounds with improved binding affinity for Mcl-1 (see, Table 1):

(compound 8)

(compound 16)

(compound 18)
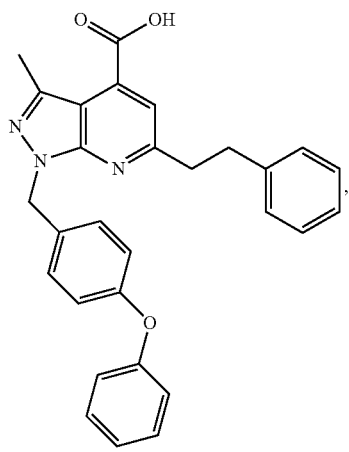

(compound 56)
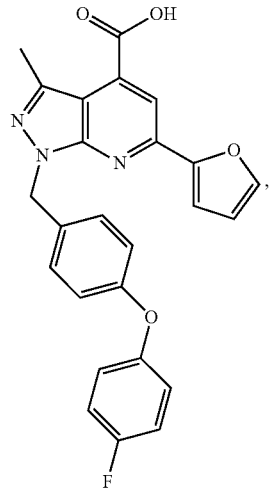

(compound 57)
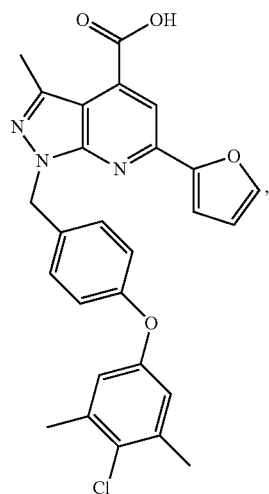

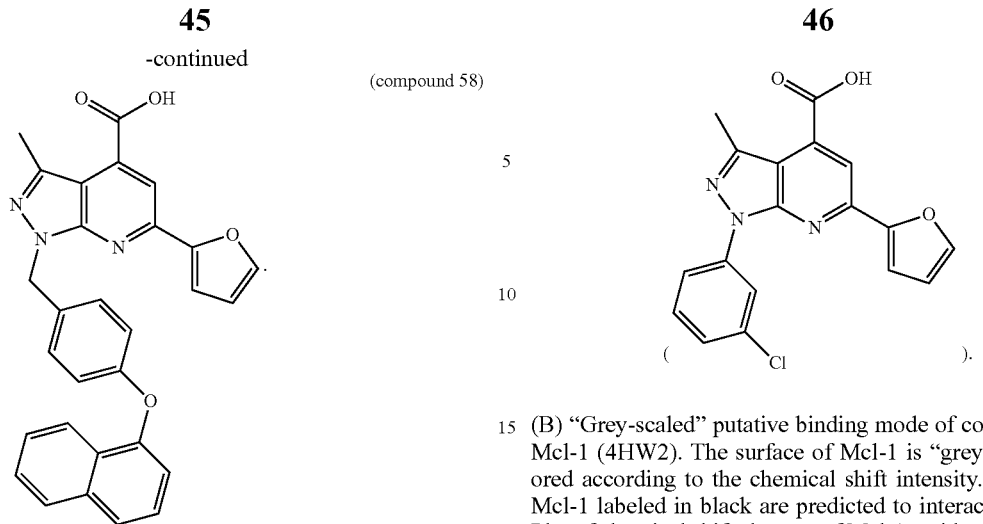

(compound 58).

Accordingly, the present invention further provides methods for treating cancer through administration of therapeutic amounts of compound 8, 16, 18, 56, 57 and/or 58 to a subject suffering from cancer. The methods are not limited to a particular type of cancer. In some embodiments, the cancer is any cancer having Mcl-1 protein activity. In some embodiments, administration of compound 8, 16, 18, 56, 57 and/or 58 results in inhibition of Mcl-1 protein activity. In some embodiments, the administered compound 8, 16, 18, 56, 57 and/or 58 binds Mcl-1 protein within its BH3 groove. In some embodiments, the administered compound 8, 16, 18, 56, 57 and/or 58 inhibits cell growth and increases cellular apoptosis for cells having Mcl-1 activity. In some embodiments, the compound 8, 16, 18, 56, 57 and/or 58 are co-administered with one or more anticancer agents.

Moreover, the present invention provides methods for inhibiting Mcl-1 protein activity in cells through exposing such cells to one or more of the pyrazolopyridine compounds of the present invention. In some embodiments, the pyrazolopyridine compound is compound 8, 16, 18, 56, 57 and/or 58. In some embodiments, the pyrazolopyridine compounds bind Mcl-1 protein thereby inhibiting the Mcl-1 protein activity. In some embodiments, the pyrazolopyridine compounds bind the BH3 groove within the Mcl-1 protein.

DEFINITIONS

Figure 1:
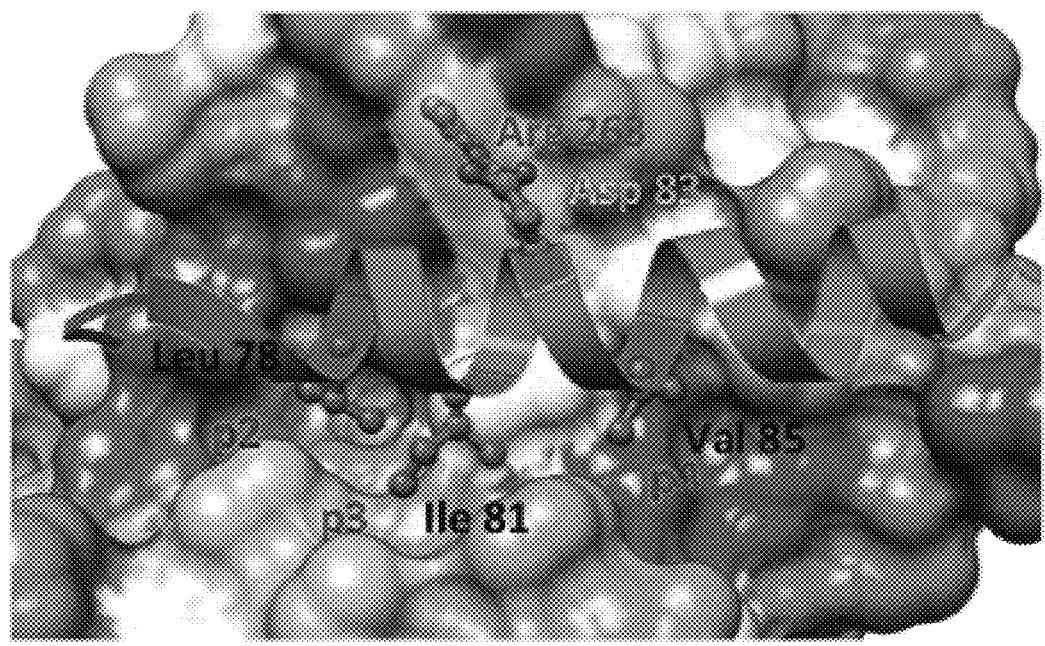
FIG. 1 shows a "grey-scaled" pharmacophore model based on the interaction of mNoxa and Mcl-1. Crystal structure of mNoxa bound to Mcl-1 (PDB 2NLA) was used. Mcl-1 is shown in surface representation while mNoxa is shown as a ribbon. Three hydrophobic residues of mNoxa are shown and labeled in black. The charged residue Asp 83 is shown and labeled in the middle spot of the ribbon.

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a pyrazolopyridine compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis.

The term "functional Mcl-1," as used herein, refers to wild-type Mcl-1 expressed at normal, high, or low levels and mutant Mcl-1 that retains at least about 5% of the activity of wild-type Mcl-1, e.g., at least about 10%, about 20%, about 30%, about 40%, about 50%, or more of wild-type activity.

The term "Mcl-1-related protein," as used herein, refers to proteins that have partial sequence homology (e.g., at least 5%, 10%, 25%, 50%, 75%, 85%, 95%, 99%, 99.999%) with Mcl-1, have tumor suppressor activity, and are inhibited by interaction with a compound of the present invention (e.g., a pyrazolopyrine compound of the present invention).

The term "bioisostere" as used herein means a chemical moiety, group or molecule whose chemical and physical similarities to another group or molecule produce similar biological properties. The term bioisostere is generally understood to refer to a portion of a molecule, rather than to the entire molecule. A bioisostere of a compound may produce a similarity in a biologically important parameter. A bioisostere of a compound may be useful to attenuate toxicity, modify activity, and/or alter the metabolism of the compound. The following parameters may be considered in developing a bioisosteric replacement: size, shape, electronic distribution, permeability, lipid solubility, water solubility, $pK_a$, chemical reactivity, and hydrogen bonding capacity. In some embodiments, the bioisostere is a carboxylic acid bioisostere.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

DETAILED DESCRIPTION OF THE INVENTION

Myeloid cell leukemia-1 (Mcl-1) is a potent anti-apoptotic protein, belonging to the prosurvival Bcl-2 subfamily and its role is emerging as a critical survival factor in a broad range of human cancers, including PC (see, e.g., Day C L, et al., J Biol Chem. 2005; 280:4738-44; Day C L, et al., J Mol Biol. 2008; 380:958-71). Functional studies have confirmed that Mcl-1 is capable of blocking apoptosis induced by various apoptotic stimuli, including chemotherapy and radiation (see, e.g., Zhou P, et al., Blood. 1997; 89:630-43). Mcl-1 is highly up-regulated in a variety of human cancers and is associated with resistance to chemotherapeutic agents (see, e.g., Miyamoto Y, et al., Oncology. 1999; 56:73-82; Schniewind B, et al., Int J Cancer. 2004; 109:182-8; Ren L N, et al., Biochem Biophys Res Commun. 2009; 386:35-9; Wei S H, et al., Cancer Chemother Pharmacol. 2008; 62:1055-64; Guoan X, et al., Surgery. 2010; 147:553-61; Huang S, et al., Cancer Res. 2008; 68:2944-51). Mcl-1 is an important survival factor and down-regulation of Mcl-1 enhances the induction of apoptosis and chemosensitivity to Gemcitabine, radiation and ABT-737 (see, e.g., Wei S H, et al., Cancer Chemother Pharmacol. 2008; 62:1055-64; Guoan X, et al., Surgery. 2010; 147:553-61; Huang S, et al., Cancer Res. 2008; 68:2944-51). Thus, Mcl-1 represents a very attractive molecular target for developing a new class of cancer therapy for treatment of human cancers by overcoming resistance to chemotherapeutic agents.

Potent small molecule inhibitors of Bcl-2 subfamily include the Bad-like BH3 mimetics (see, e.g., Oltersdorf T, et al., Nature. 2005; 435:677-81; Tse C, et al., Cancer Res. 2008; 68:3421-8). ABT-737, one of these mimetics, binds with high affinity ($K_i \leq 1$ nM) to Bcl-2, Bcl-$x_L$ and Bcl-w but fails to bind to Mcl-1 (see, e.g., Oltersdorf T, et al., Nature. 2005; 435:677-81). Several studies have shown that resistance to ABT-737 is linked to high expression levels of Mcl-1 and in many instances this resistance can be overcome by treatment with agents that down-regulate, destabilize, or inactivate Mcl-1 (see, e.g., van Delft M F, et al., Cancer Cell. 2006; 10:389-99; Chen S, et al., Cancer Res. 2007; 67:782-91). It was recently shown that knockdown of Mcl-1 sensitizes human PC cancer cells to ABT-737-induced apoptosis, indicating that Mcl-1 is a relevant therapeutic target in these cancer cells (see, e.g., Huang S, et al., Cancer Res. 2008; 68:2944-51).

High throughput screen (HTS) approach is a known strategy for identification of potential lead compounds for further development (see, e.g., Macarron, R., et al., Nat Rev Drug Discov 2011, 10, 188-95). In experiments conducted during the course of developing embodiments for the present invention, to identify small-small molecule Mcl-1 inhibitors, a dual-readout HTS assay that combines two assay technologies, fluorescence polarization (FP) and Forster resonance energy transfer (FRET), was developed, optimized and miniaturized to a 1,536-well ultra-HTS format (see, e.g., Du, Y., et al., Assay Drug Dev Technol 2011, 9, 382-93). The assay was used to screen a library of 102,255 compounds at Emory University Molecular Libraries Screening Center using recombinant Mcl-1 and either a labeled Noxa or Bid BH3 derived peptides. The identified hits from the both primary screens were subjected to secondary dose-response tests and a total of 1214 (875 from Mcl-1/Noxa and 509 from Mcl-1/Bid) including 170 overlapping compounds were identified. All the dose-response curves were further deposited in the PubChem's BioAssay Database under AID 1417 (see, e.g., http:// (followed by) pubchem.ncbi.nlm. (followed by) nih.gov/assay/assay.cgi?aid=1417) and 1418 (see, e.g., http:// (followed by) pubchem.ncbi.nlm. (followed by) nih.gov/assay/assay.cgi?aid=1418).

A high hit rate in HTS campaigns can make the identification of the most promising hits a challenging task and thus novel strategies to simplify this process are desired. Therefore, an integrated screening approach was employed by combining in silico target-based screening for selection of the most promising hits. For this purpose, molecular docking using the crystal structure of Mcl-1 bound to mNoxa (PDB 2NLA) (see, e.g., Czabotar, P. E. et al., Proc Natl Acad Sci USA 2007, 104, 6217-22) was utilized and all identified hits were subjected to Schrödinger's Induced Fit Docking (IFD) protocol (see, e.g., Schrödinger Suite 2011 Induced Fit Docking protocol; Glide version 5.7, Schrödinger, LLC, New York, N.Y., 2009; Prime version 3.0, Schrödinger, LLC, New York, N.Y. 2011) at the BH3 binding site of Mcl-1. A pharmacophore model (FIG. 1) was developed based on the interactions of mNoxa and Mcl-1 which included 3 hydrophobic and one hydrogen bond/electrostatic interactions. Compounds able to mimic at least two of the 4 conserved interactions of mNoxa with Mcl-1 were selected. This totaled 67 compounds from which 48 were purchased from commercial vendors. All 48 compounds were subjected to rigorous biochemical and biophysical assays which included dose-response competitive FP and SPR assays against Mcl-1 and HSQC NMR studies. Compounds which gave consistent results in all the binding assays were considered as validated hits and those with promising chemical scaffolds were selected for further optimization.

Accordingly, the present invention relates to compounds which function as inhibitors of Mcl-1 proteins. By inhibiting the activity of Mcl-1, these compounds sensitize cells to inducers of apoptosis and/or cell cycle arrest and, in some instances, themselves induce apoptosis and/or cell cycle arrest. Therefore, the invention relates to methods of sensitizing cells to inducers of apoptosis and/or cell cycle arrest and to methods of inducing apoptosis and/or cell cycle arrest in cells, comprising contacting the cells with a compound of the invention alone or in combination with additional agent(s), e.g., an inducer of apoptosis or a cell cycle disrupter.

The invention further relates to methods of treating, ameliorating, or preventing disorders in a patient, such as those that are responsive to induction of apoptosis, comprising administering to the patient a compound of the invention and additional agent(s), e.g., an inducer of apoptosis. Such disorders include those characterized by a dysregulation of apoptosis and those characterized by the proliferation of cells expressing functional Mcl-1 proteins (e.g., pancreatic cancer).

In a particular embodiment, pyrazolopyridine compounds encompassed within any Formulas I, II, III or IV are provided:

Formula I:

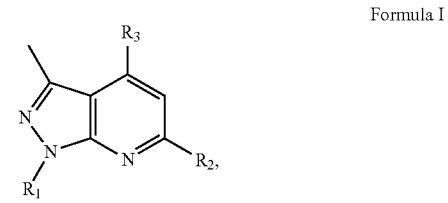

Formula II

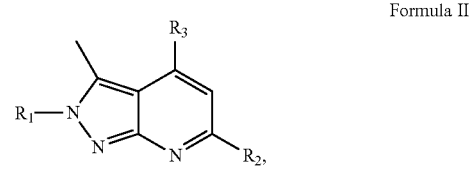

Formula III

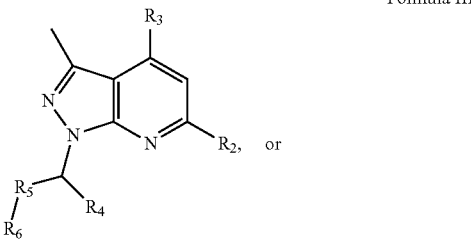

or

Formula IV

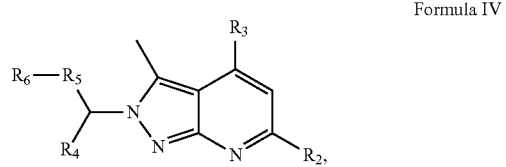

including pharmaceutically acceptable salts, solvates, and/or prodrugs thereof.

Formulas I, II, III or IV is not limited to a particular chemical moiety for R1, R2, R3, R4, R5 and R6. In some embodiments, the particular chemical moiety for R1, R2, R3, R4, R5 and R6 independently include any chemical moiety that permits the resulting compound to bind with an Mcl-1 protein. In some embodiments, the particular chemical moiety for R1, R2, R3, R4, R5 and R6 independently include any chemical moiety that permits the resulting compound to bind the BH3 binding pocket of Mcl-1

In some embodiments, R1 is a substituted or non-substituted aryl moiety. In some embodiments, R1 is a substituted or non-substituted alkaryl moiety. In some embodiments, R1 is selected from

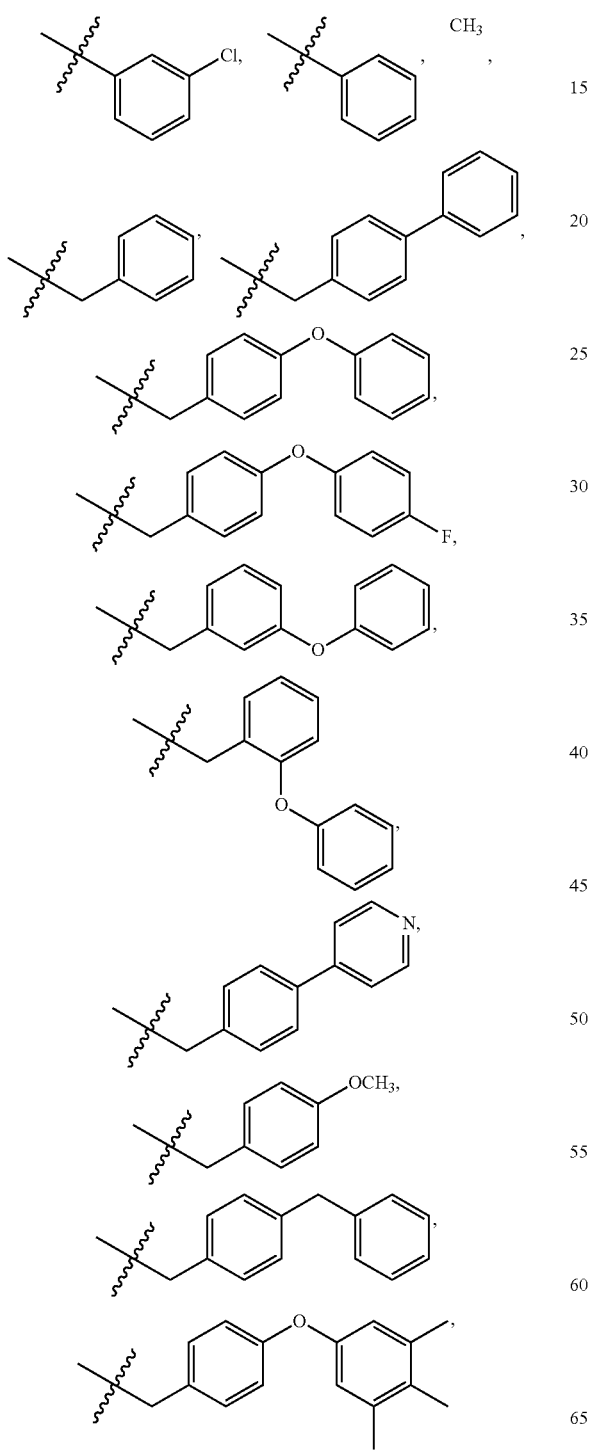

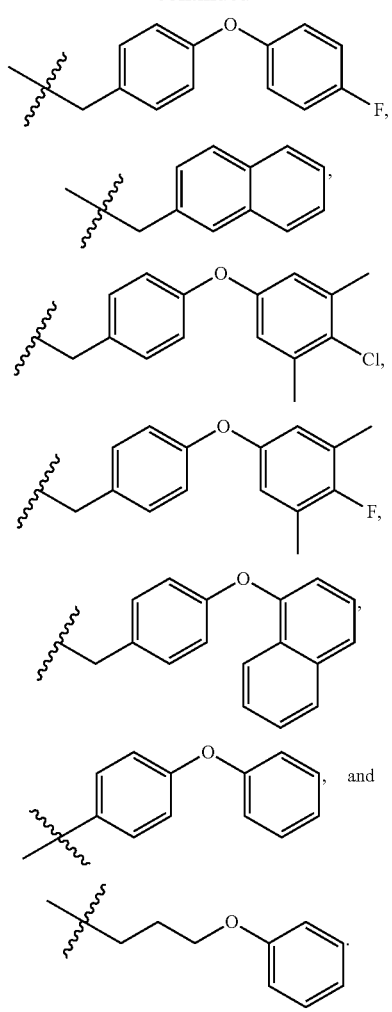

In some embodiments, R1 is hydrogen.

In some embodiments, R2 is an alkyl moiety, an alkylenyl moiety, an alkynyl moiety, an aminoakyl moiety, a phenethyl moiety, a styryl moiety, a phenylethynyl moiety, a halogen moiety, or a (furan-2-ylmethyl)amino moiety. In some embodiments, R2 is selected from halogen (e.g., Chlorine),

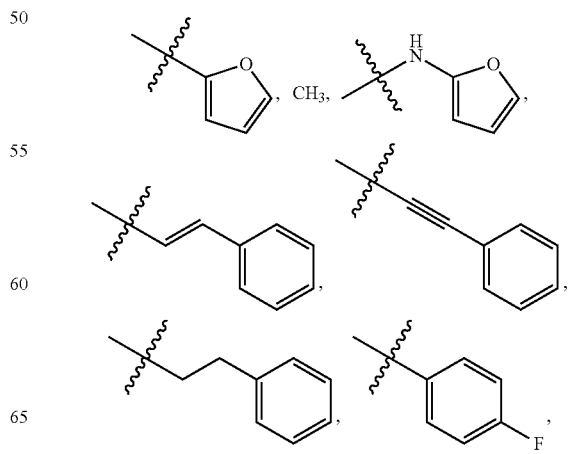

-continued

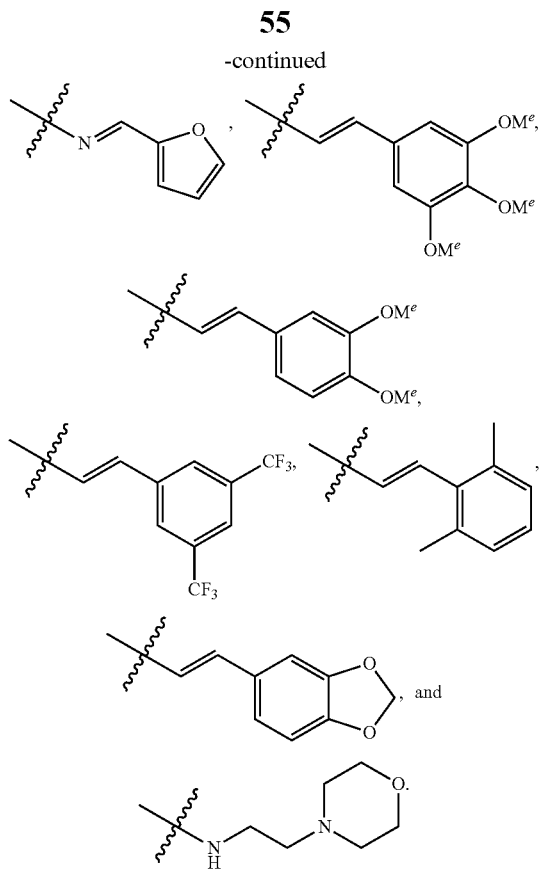

In some embodiments, R2 is hydrogen.

In some embodiments, R3 is an acid moiety. In some embodiments, R3 is an ester moiety. In some embodiments, R3 is hydrogen. In some embodiments, R3 is $CH_3$. In some embodiments, R3 is OH. In some embodiments, R3 is a carboxylic acid bioisostere moiety. In some embodiments, R3 is selected from H, OH, $OCH_3$, $OCH_2CH_3$, COOH, $COOCH_3$, $COOCH_2CH_3$,

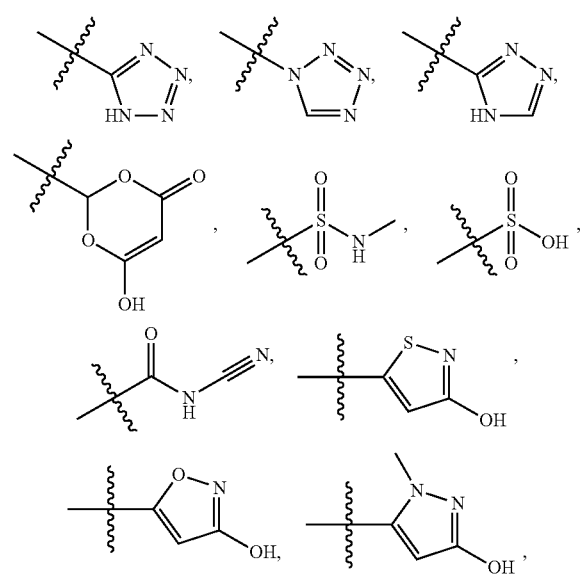

-continued

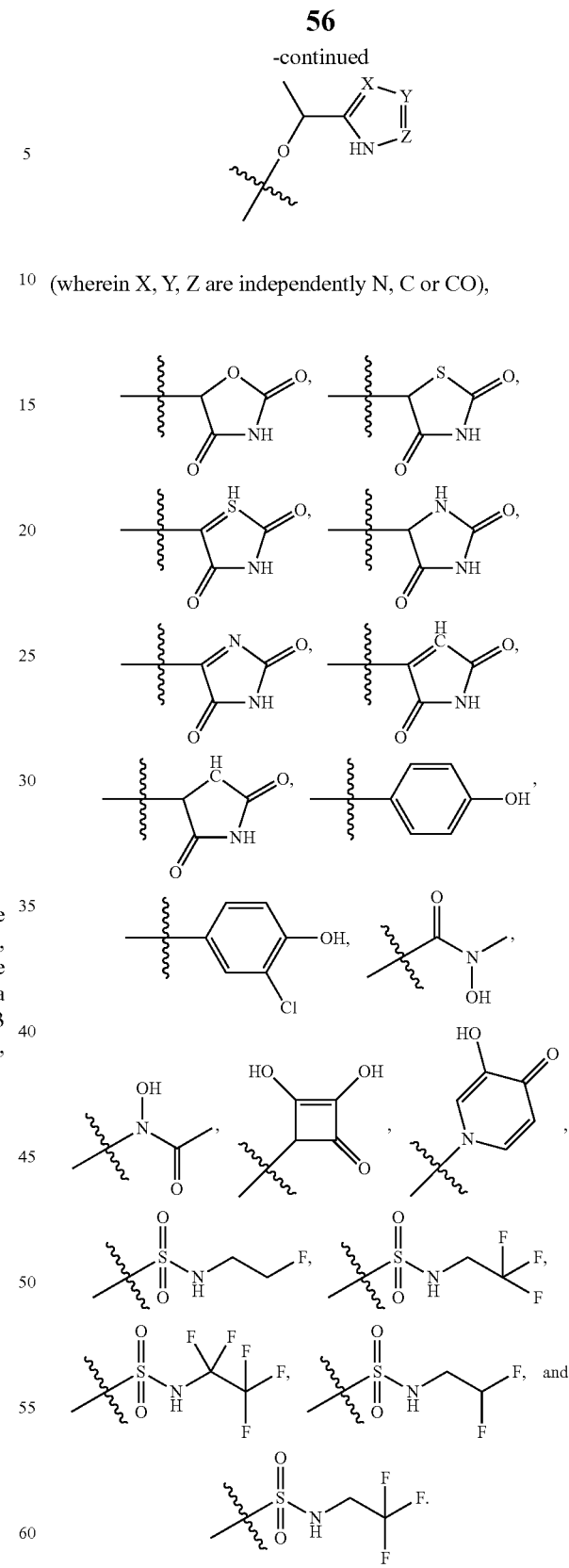

(wherein X, Y, Z are independently N, C or CO),

In some embodiments, R4 is an optionally substituted alkyl moiety, a cycloalkyl moiety, an aryl moiety, or a heterocyclic moiety. In some embodiments, R4 is selected from OH, hydrogen,

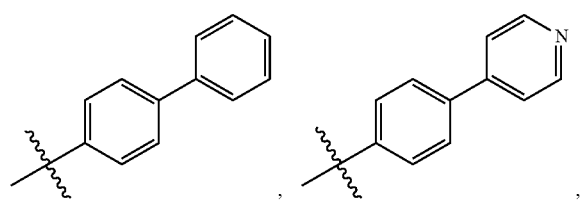
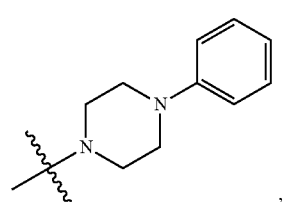
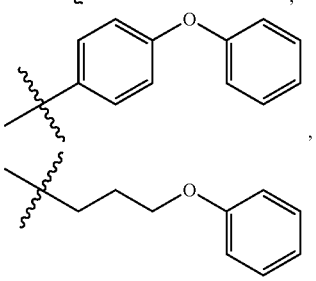
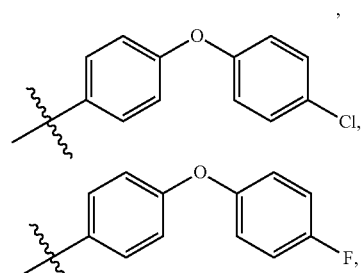
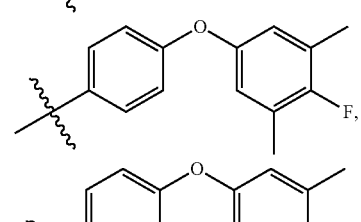
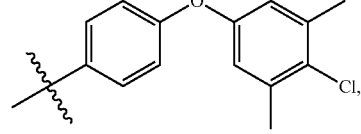
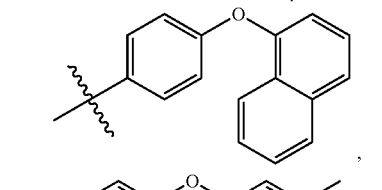
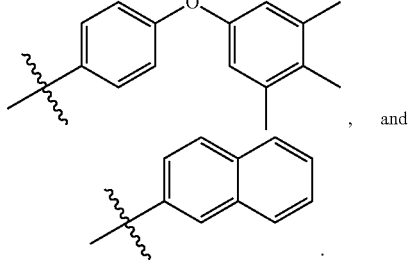
, and
In some embodiments, R5 is selected from
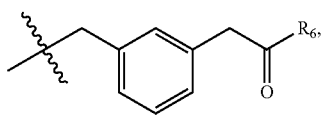
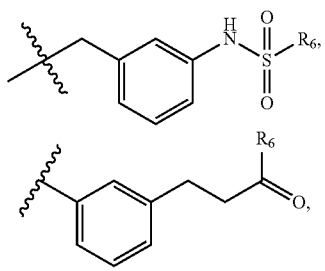
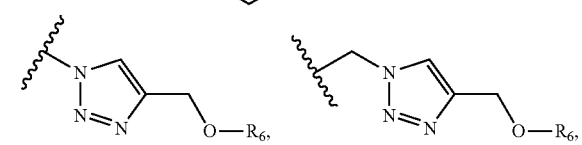
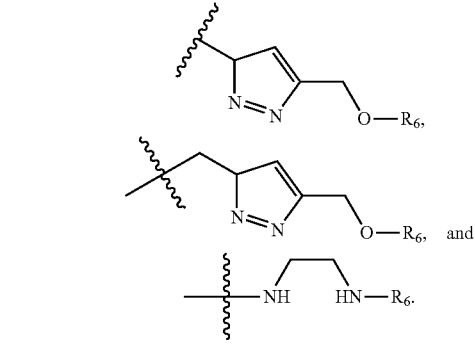
, and
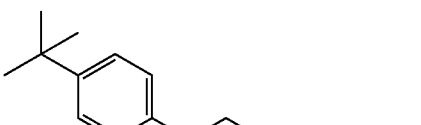
In some embodiments, R6 is absent. In some embodiments, R6 is selected from the group consisting of
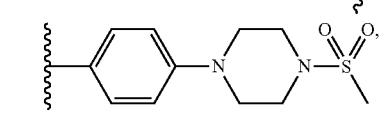
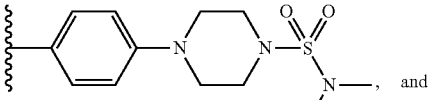
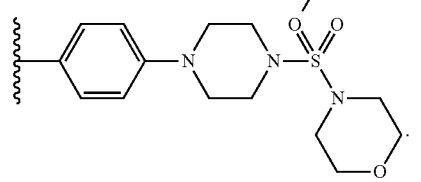
, and
Table 1 shows binding affinities ($IC_{50}$ values were determined with fluorescence polarizing binding assay) for various compounds encompassed and inhibition against Mcl-1 within Formulas I, II, III or IV.

In some embodiments, the following compounds are contemplated for Formulas I, II, III or IV:
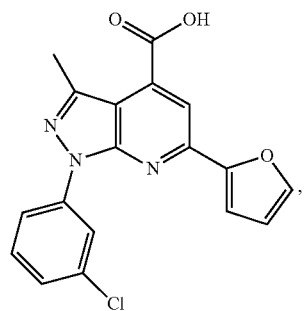 (compound 1)
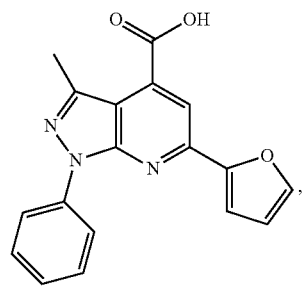 (compound 2)
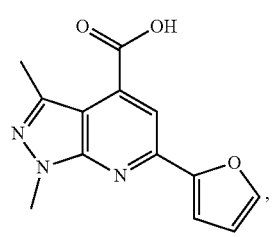 (compound 3)
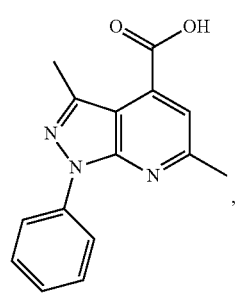 (compound 4)
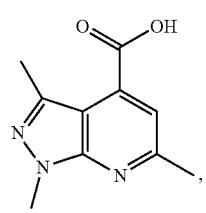 (compound 5)
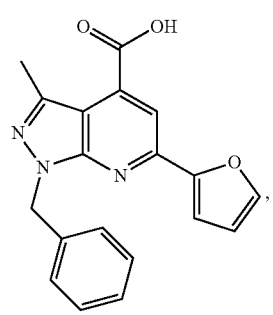 (compound 6)
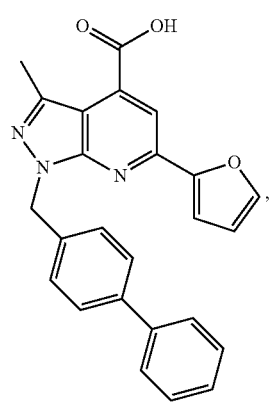 (compound 7)
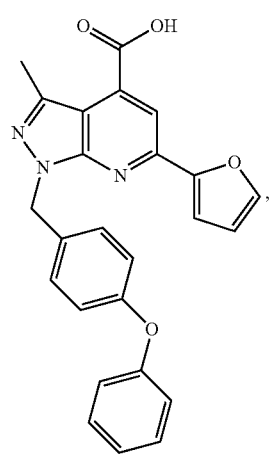 (compound 8)

-continued
(compound 9)
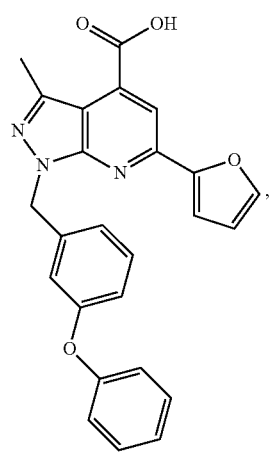
(compound 10)
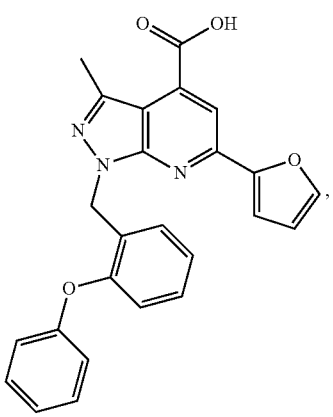
(compound 11)
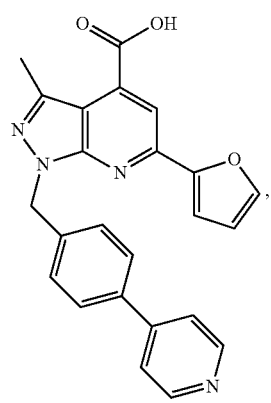
(compound 12)
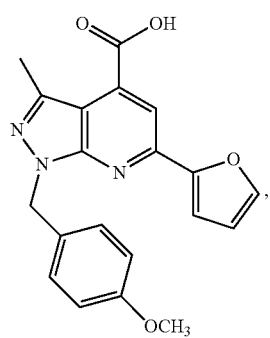
(compound 13)
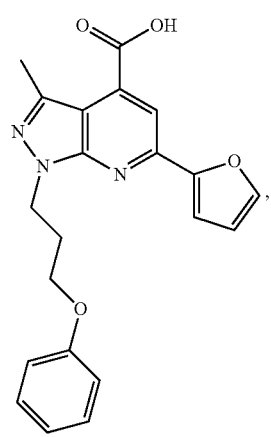
(compound 14)
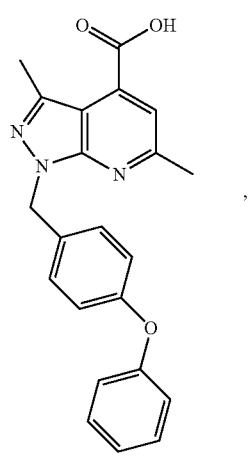

(compound 15)
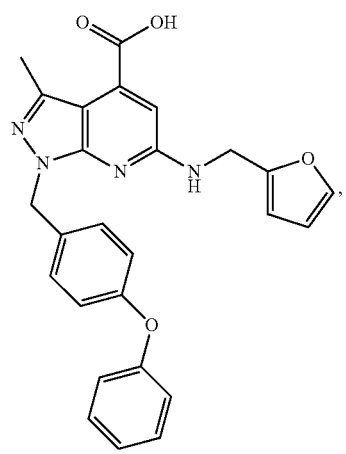
(compound 16)
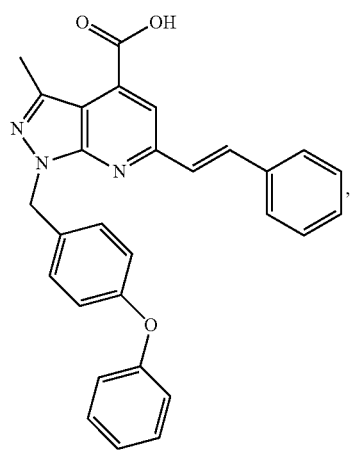
(compound 17)
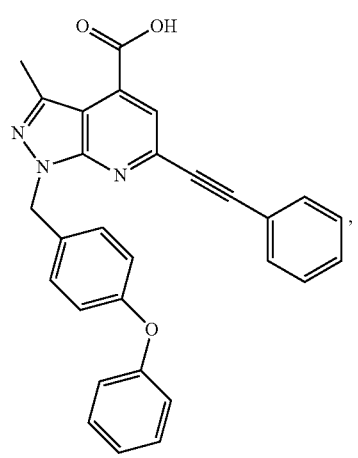
(compound 18)
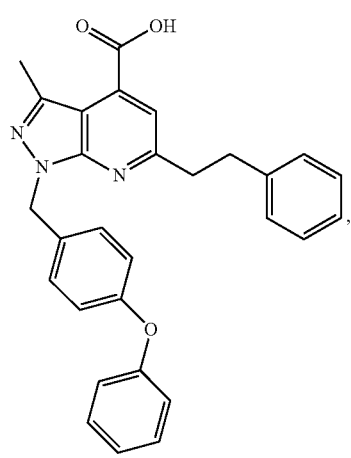
(compound 19)
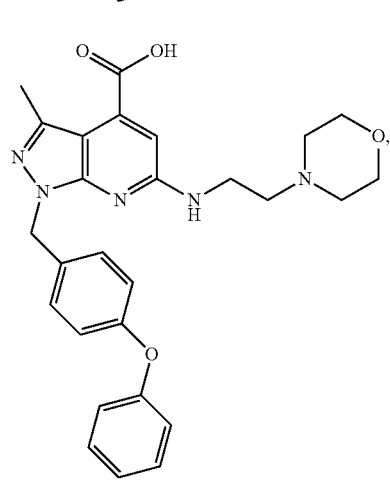
(compound 35)
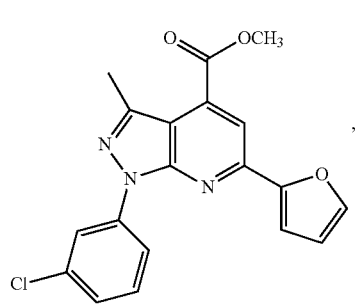
(compound 36)
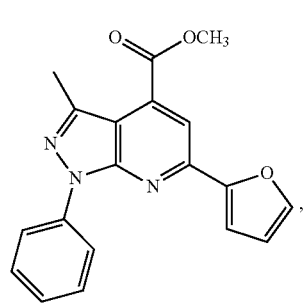
(compound 37)
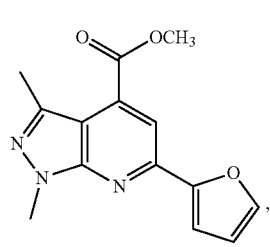

-continued
(compound 38)
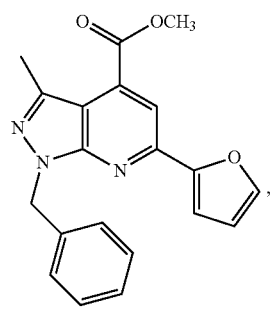
(compound 39)
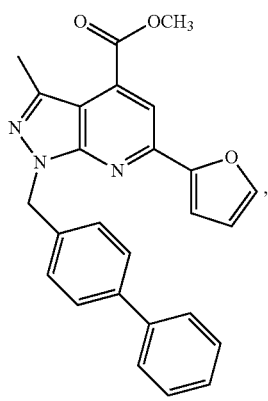
(compound 40)
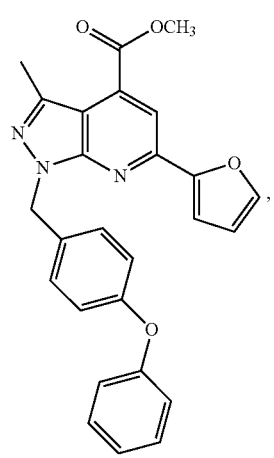
(compound 41)
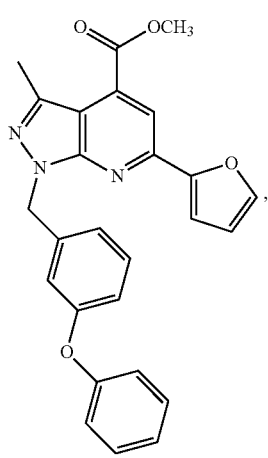
(compound 42)
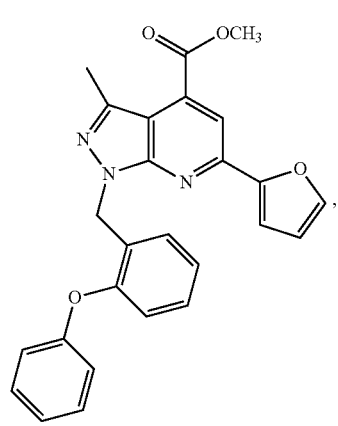
(compound 43)
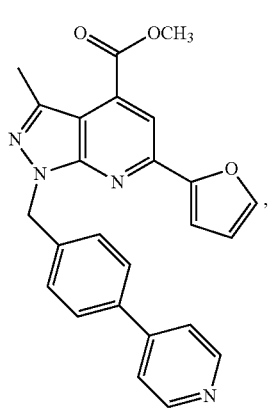

-continued
(compound 44)
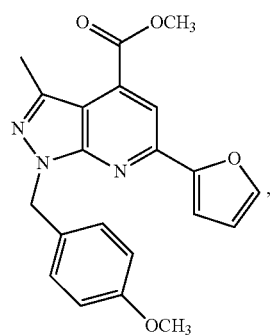
(compound 45)
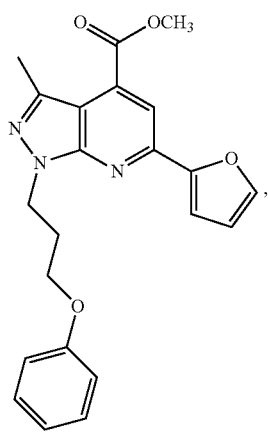
(compound 46)
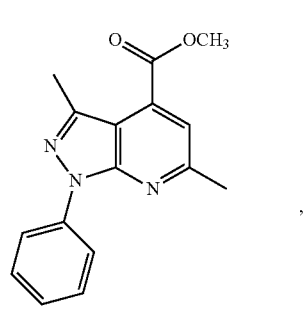
(compound 47)
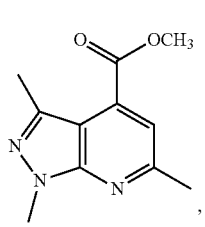
(compound 48)
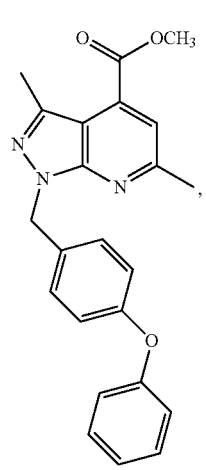
(compound 49)
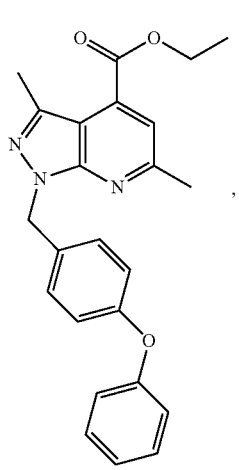
(compound 50)
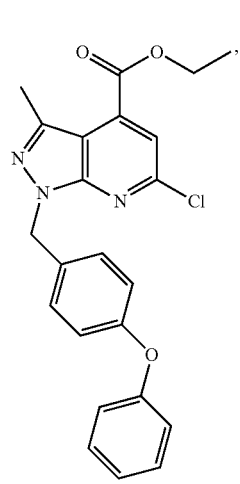
(compound 51)
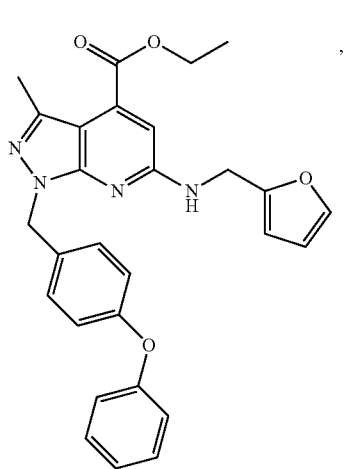

-continued
(compound 52)
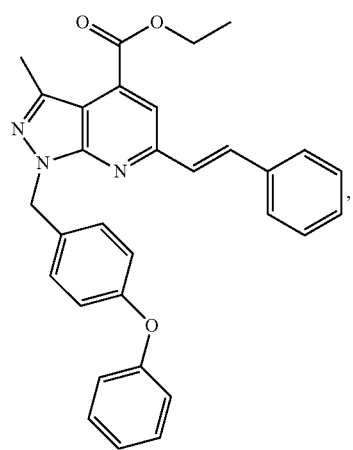
(compound 53)
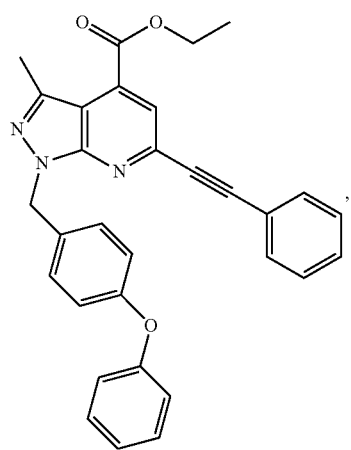
(compound 54)
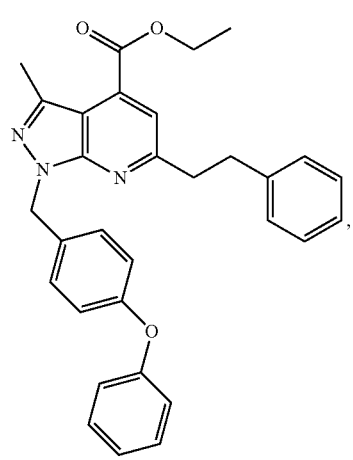
(compound 55)
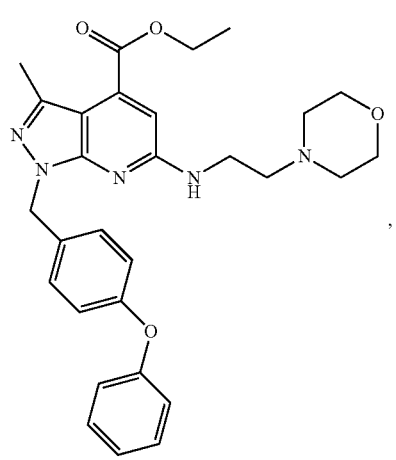
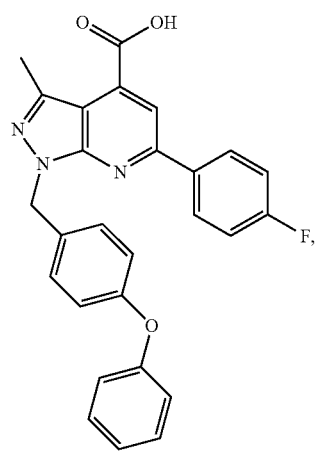
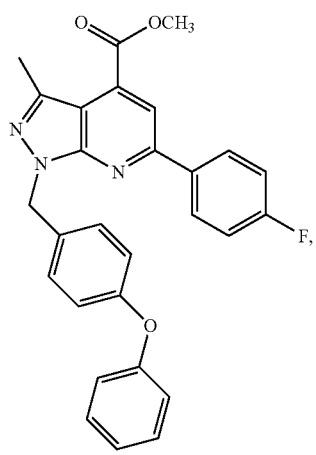
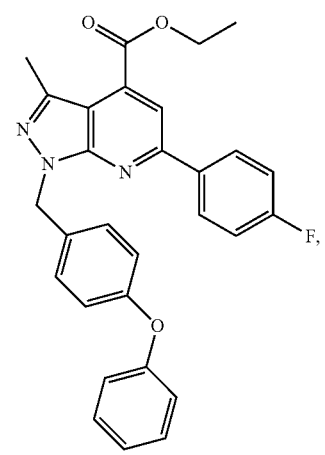

-continued
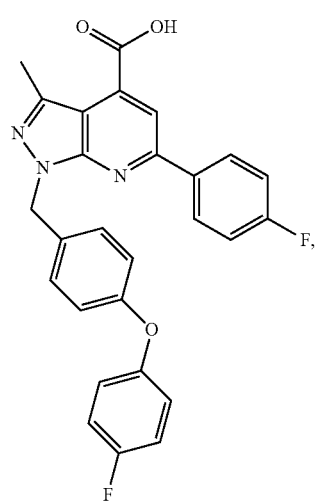
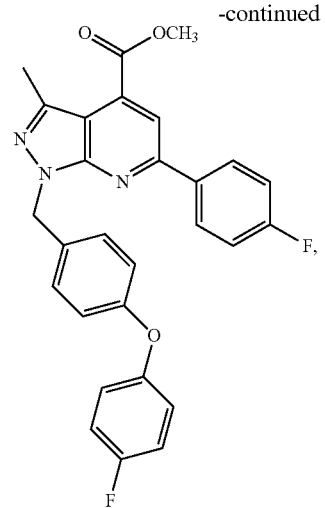
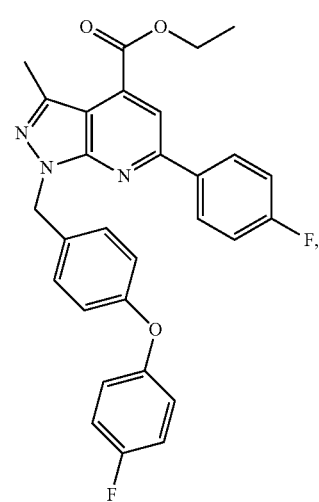
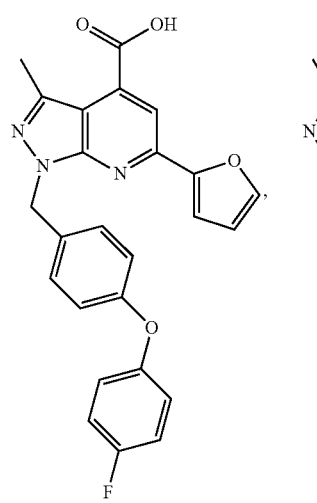
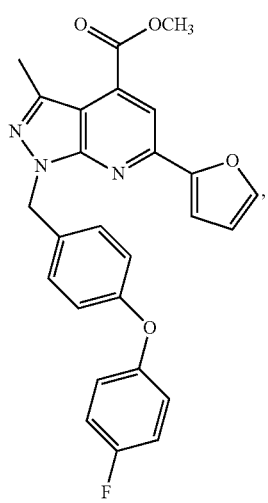
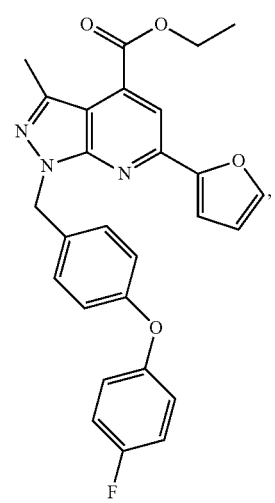
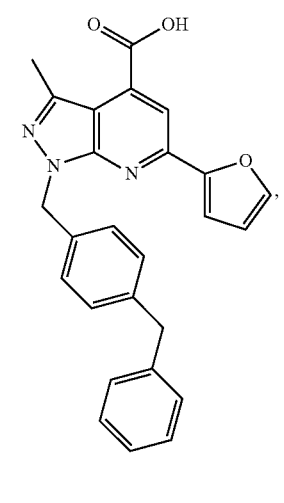
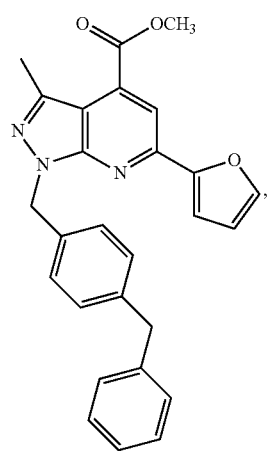
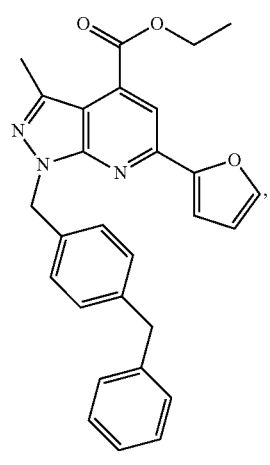
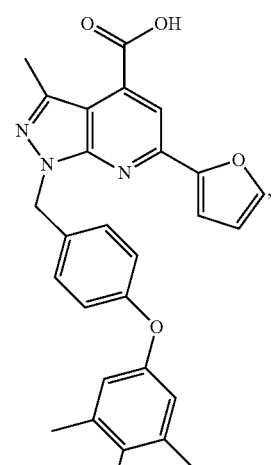
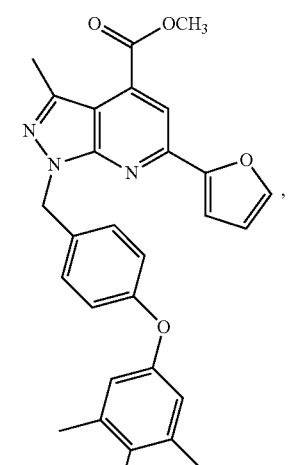

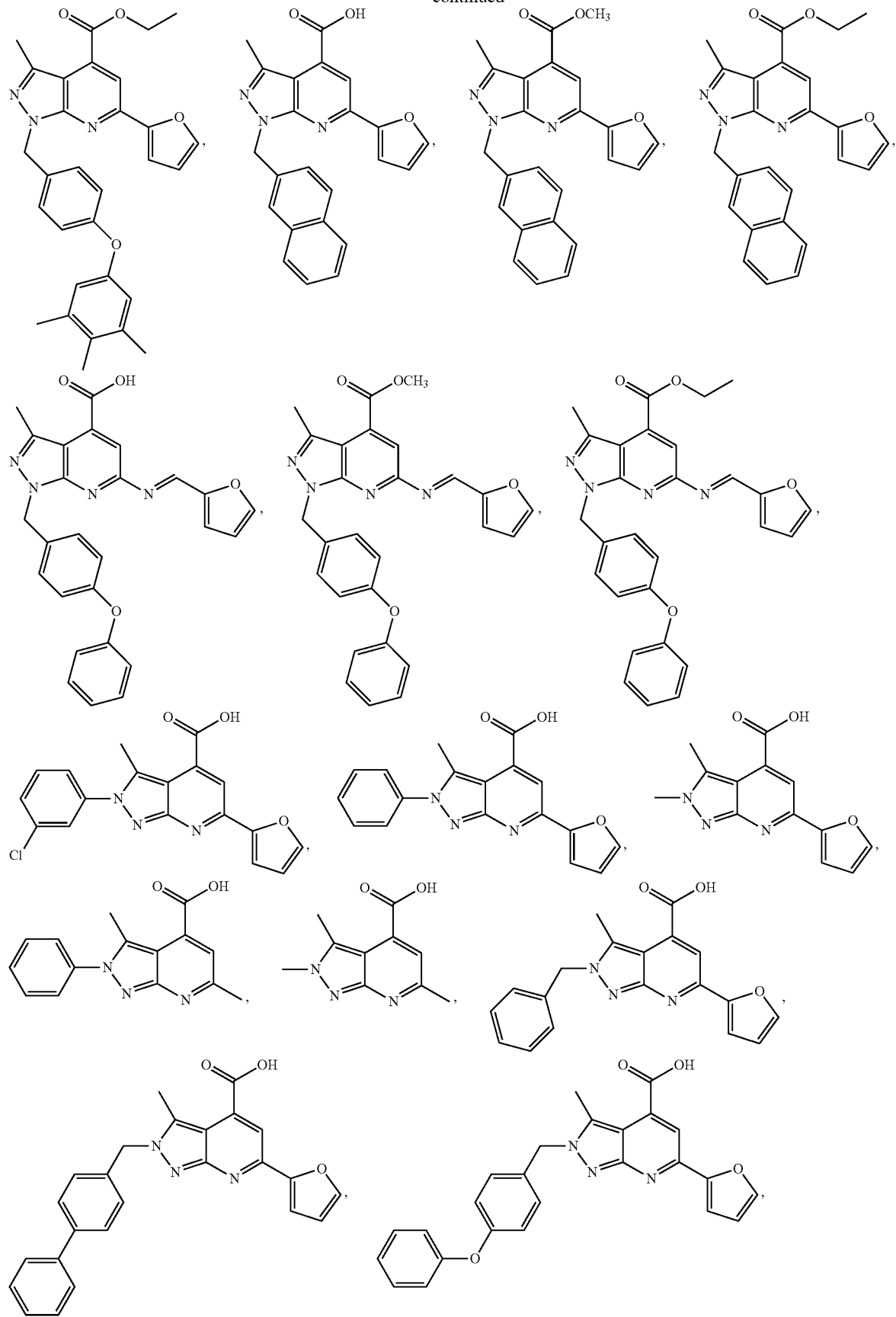

75
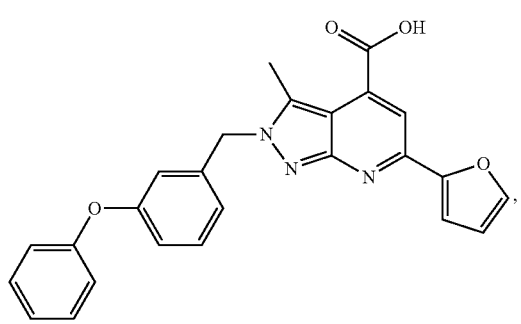
76
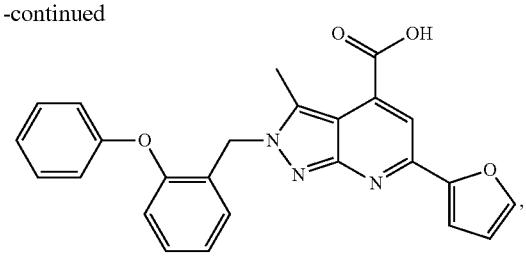
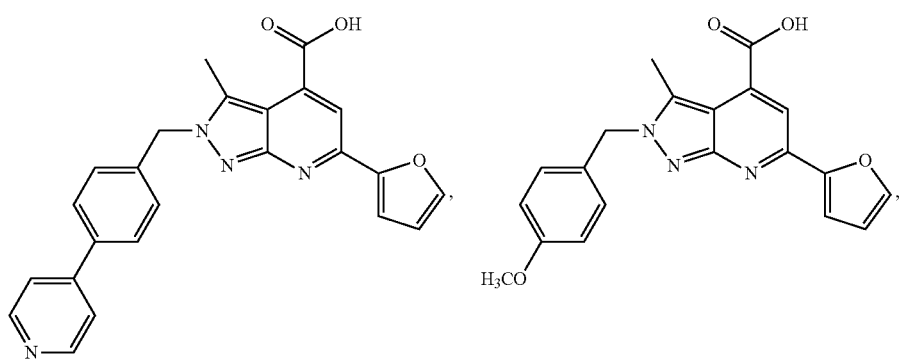
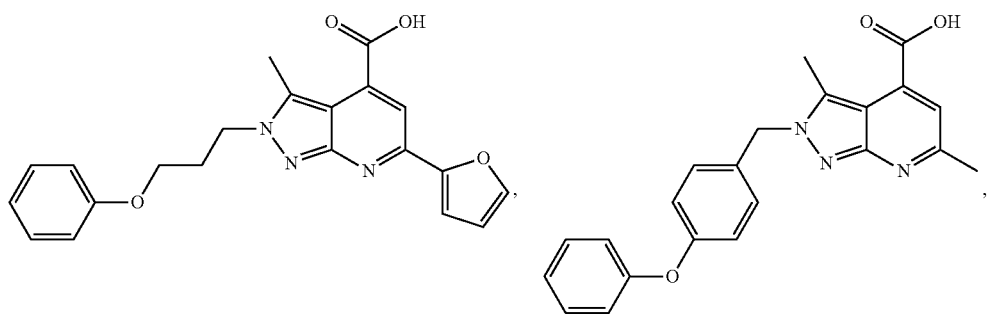
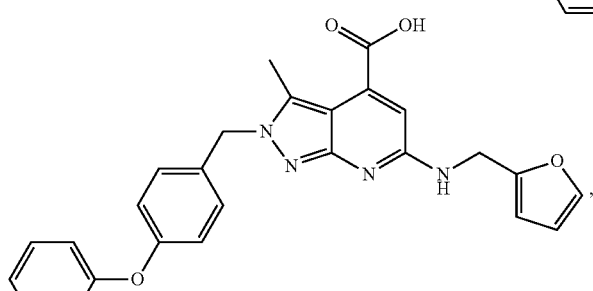
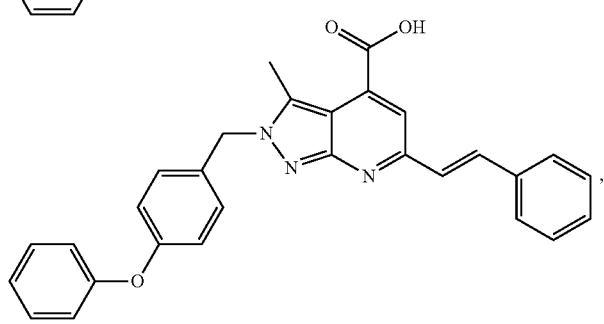

-continued
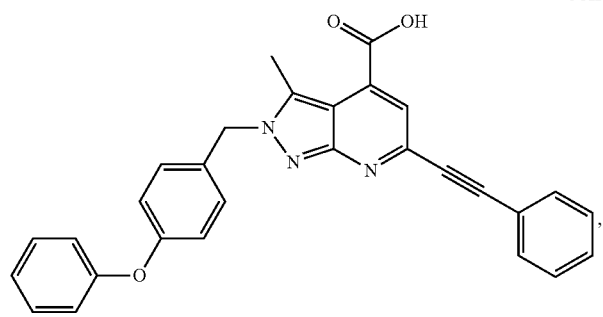
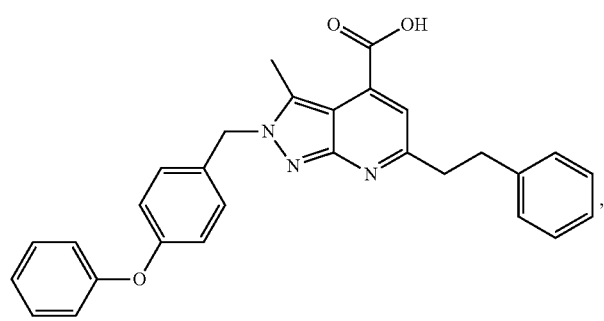
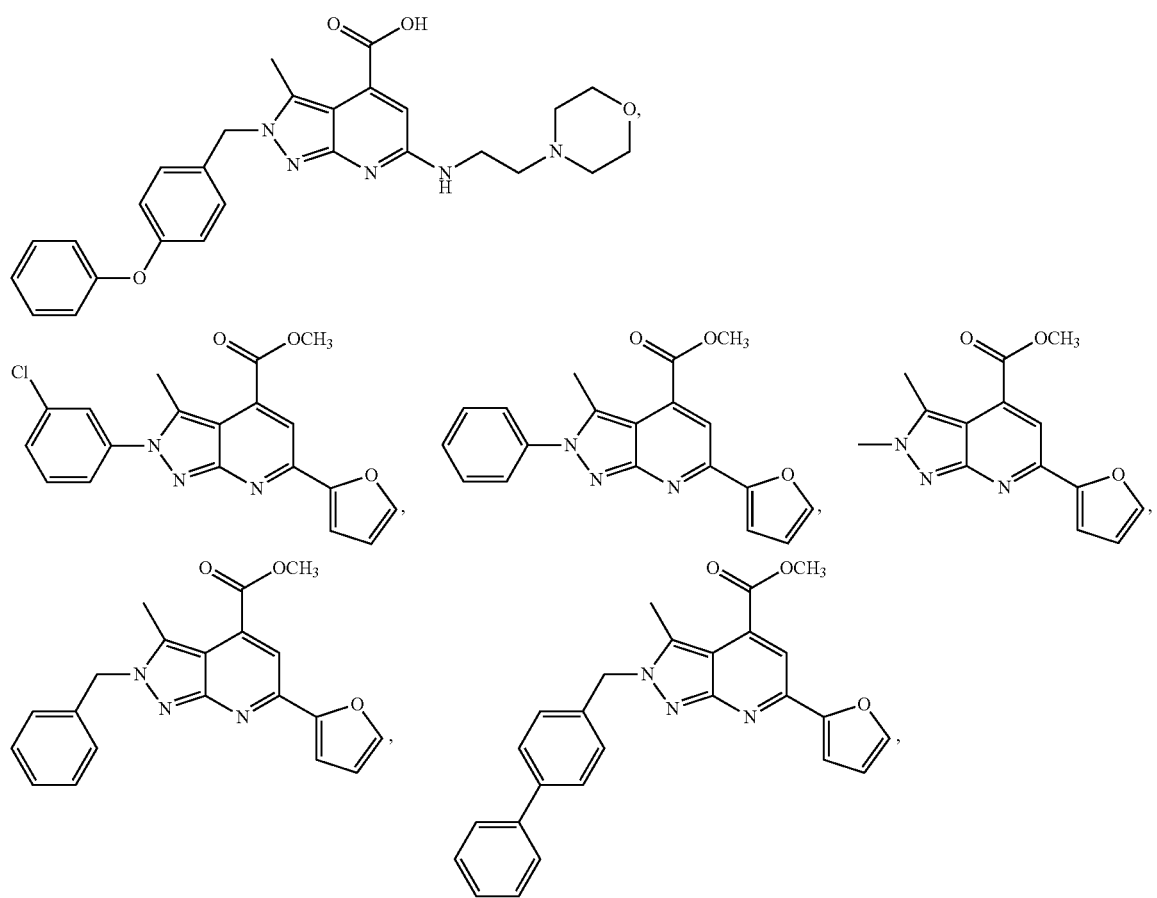

-continued
79
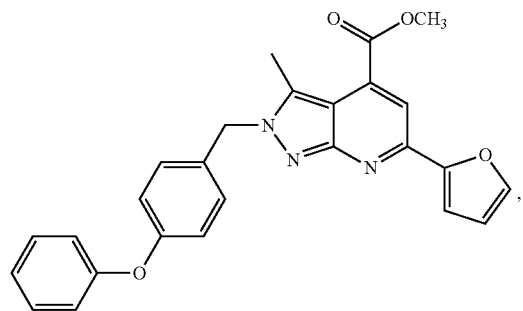
80
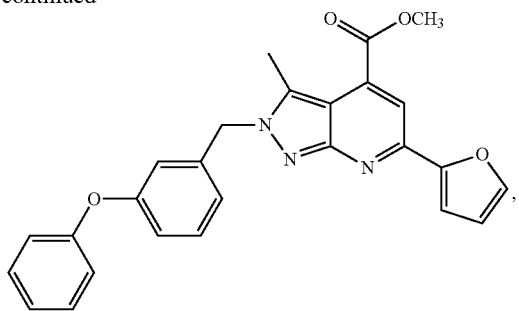
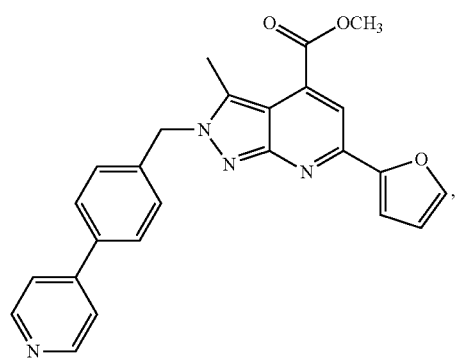
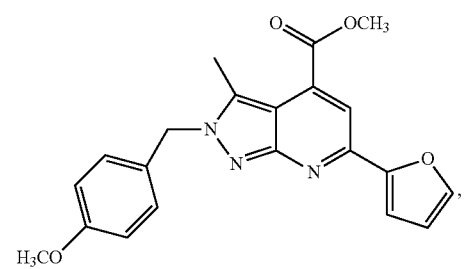
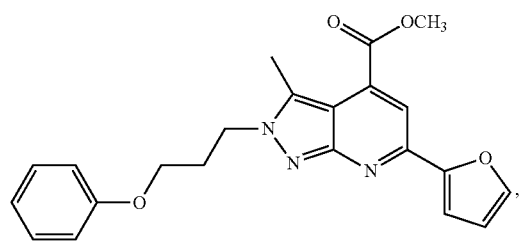
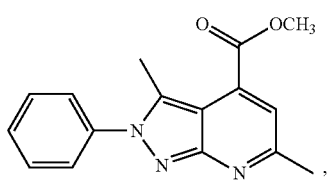
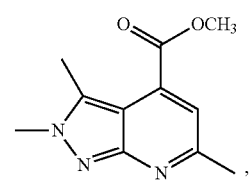
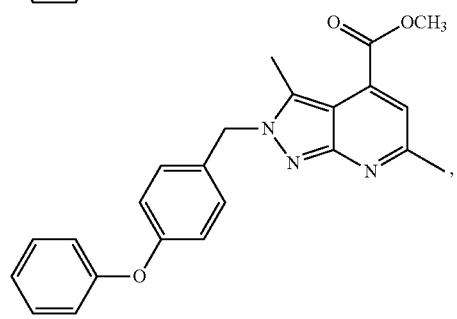
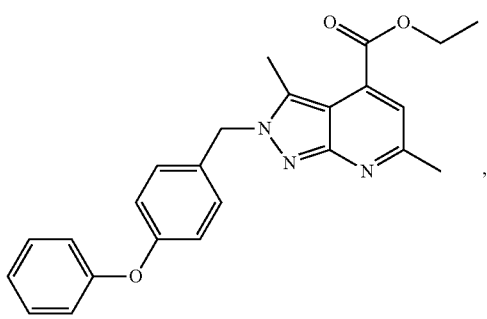
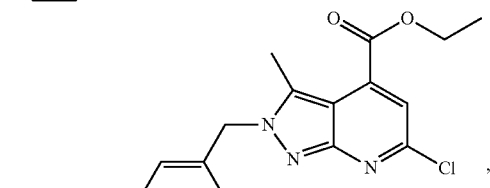
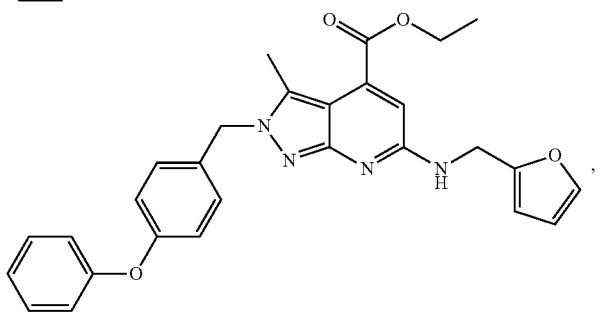

-continued
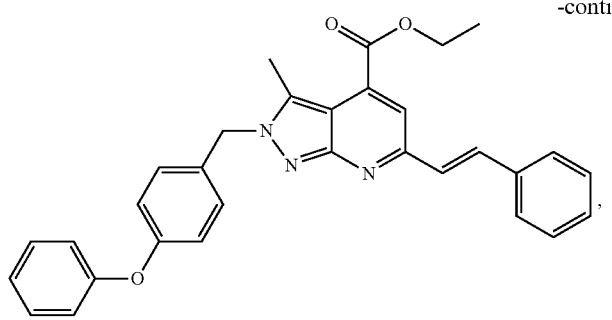
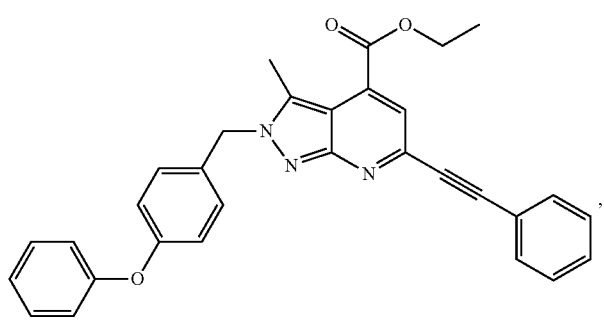
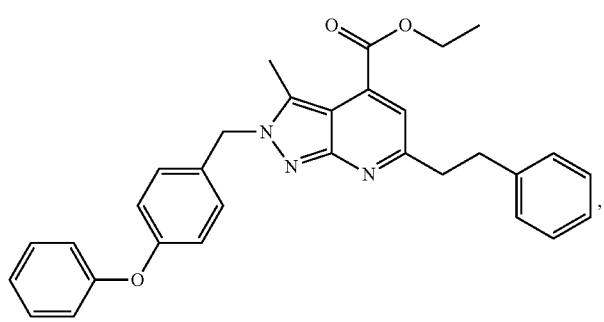
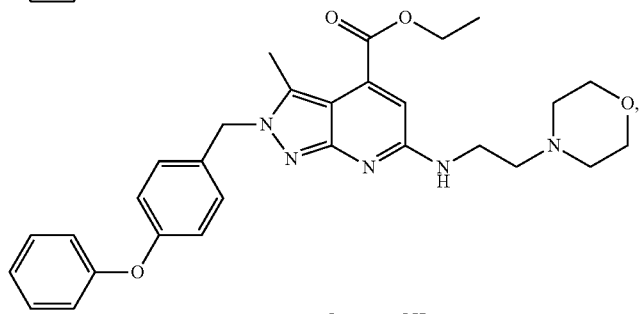
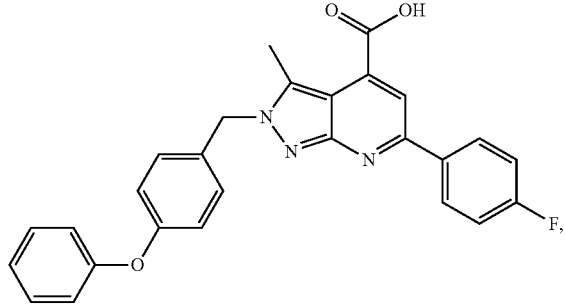
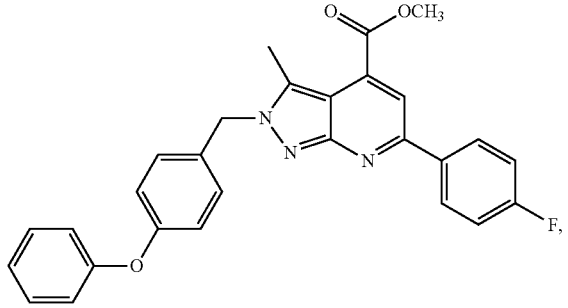

-continued
83 84
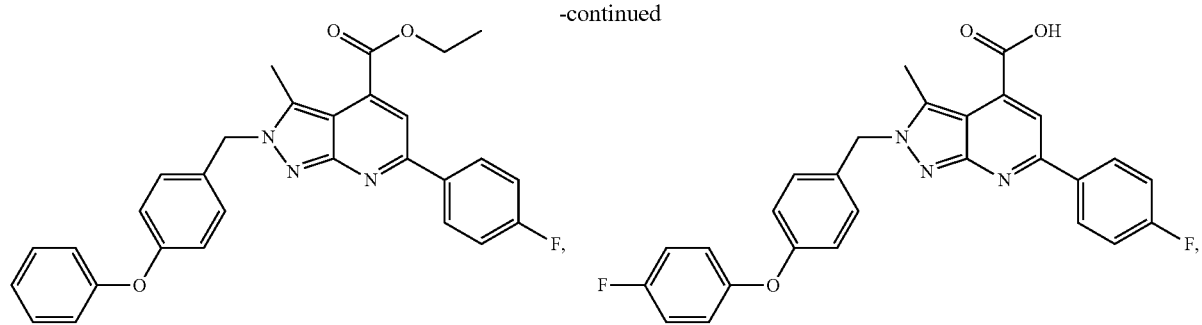
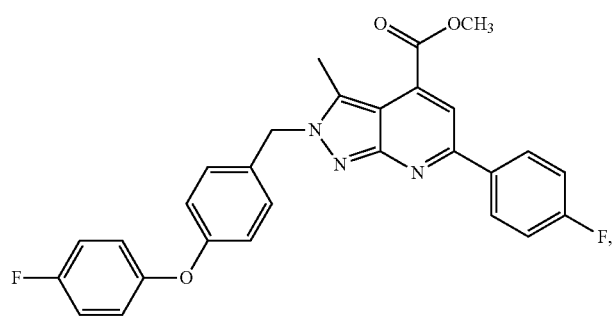
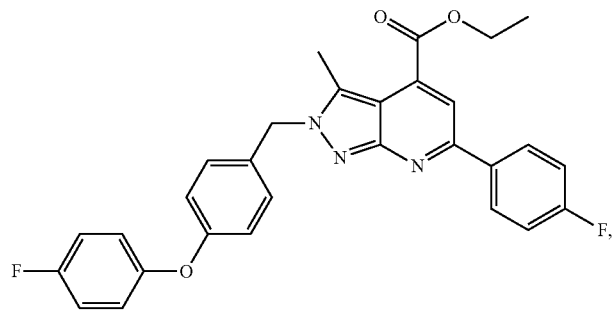
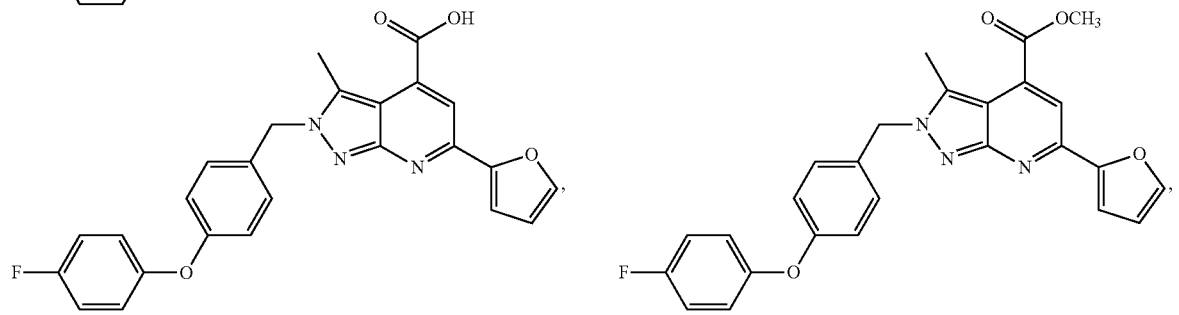
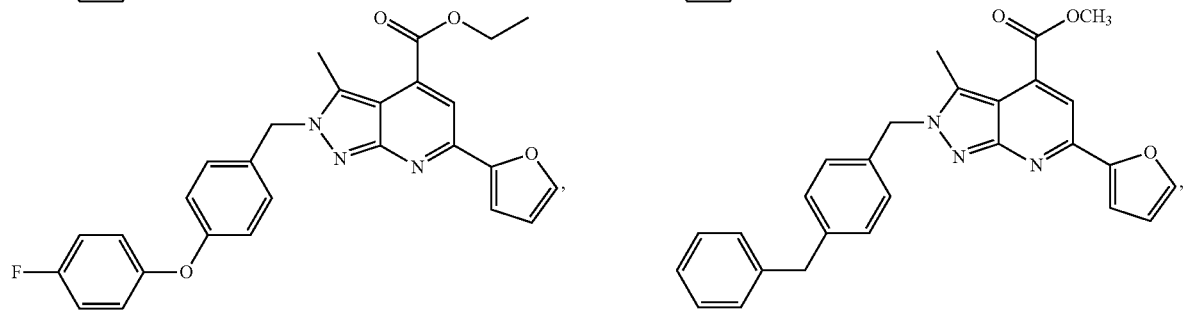

85
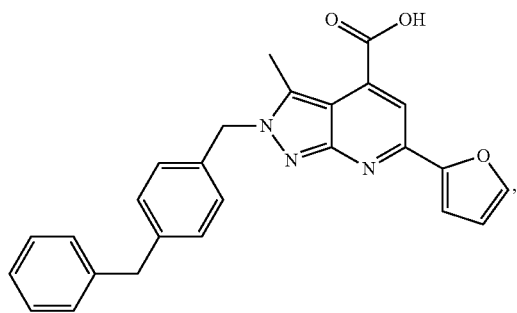
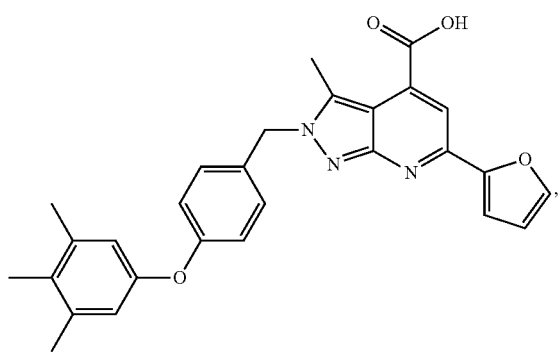
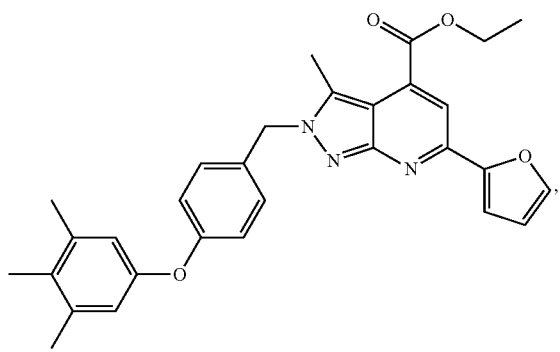
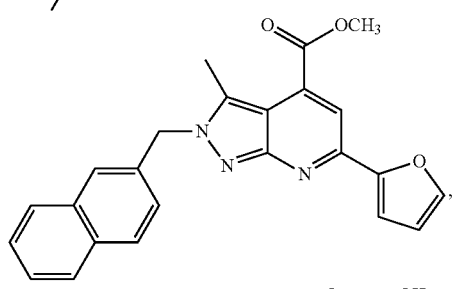
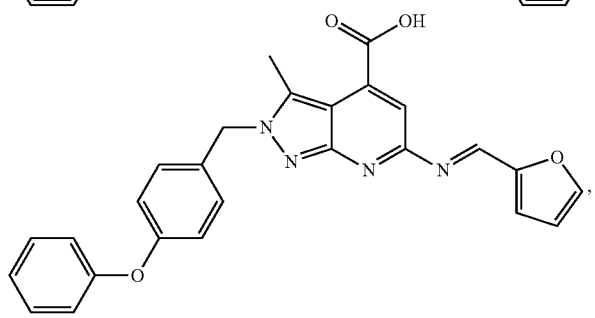
86
-continued
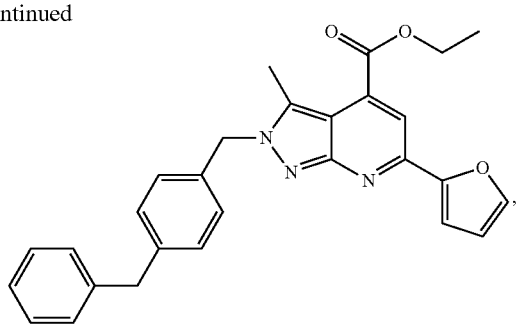
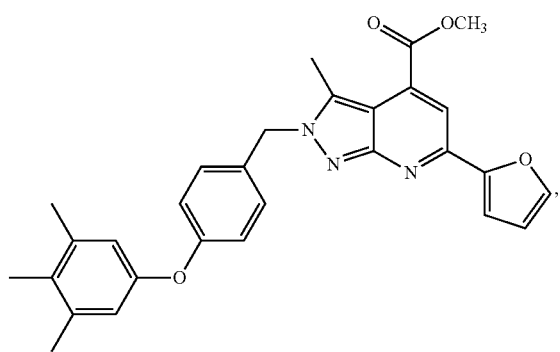
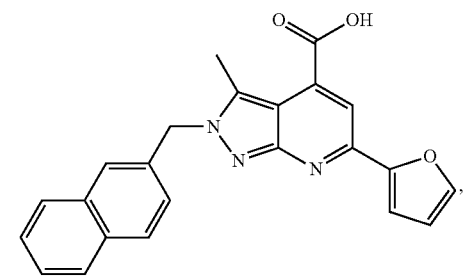
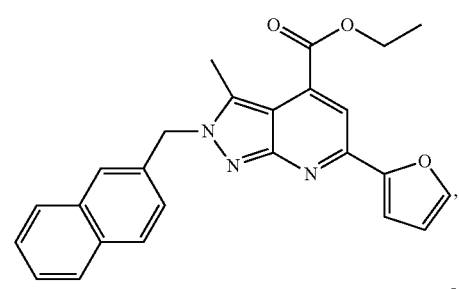
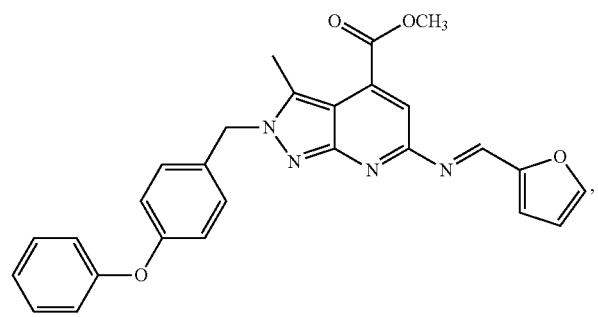

-continued
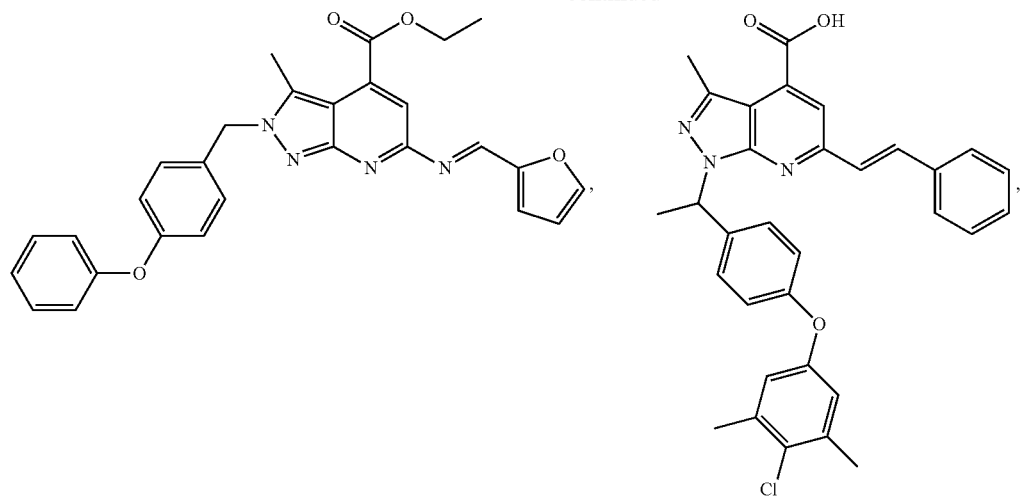
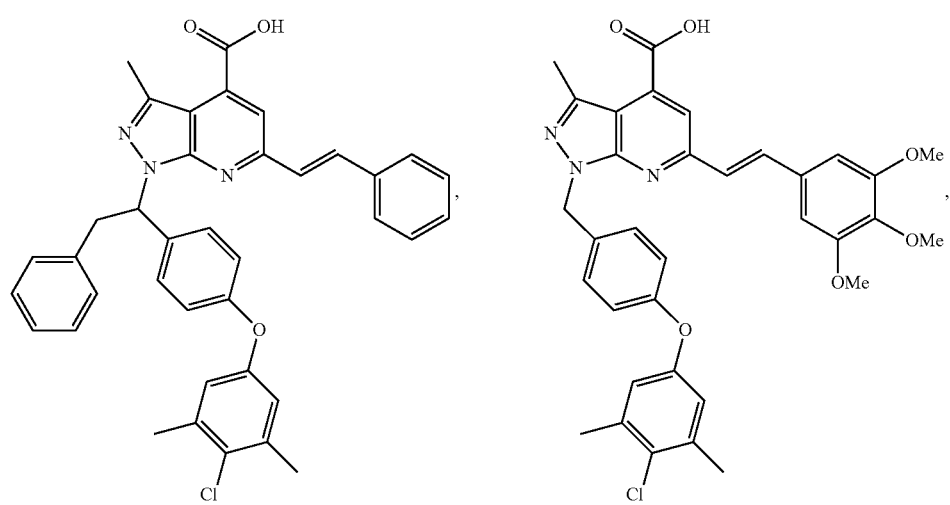
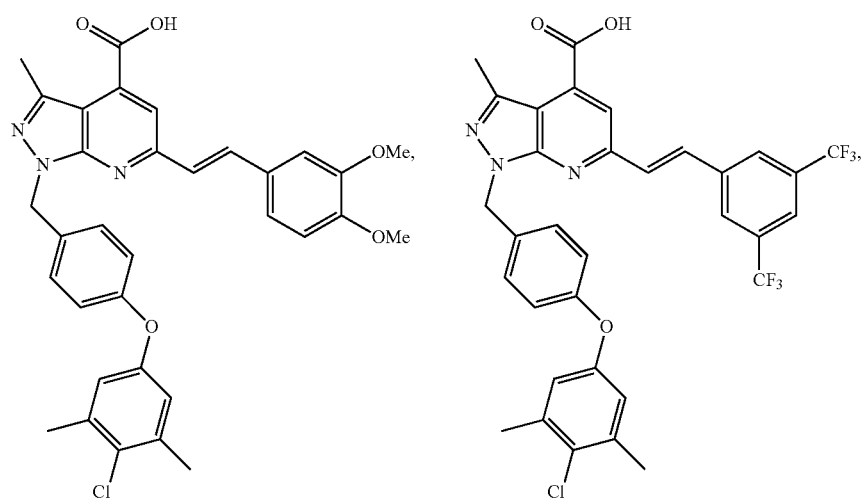

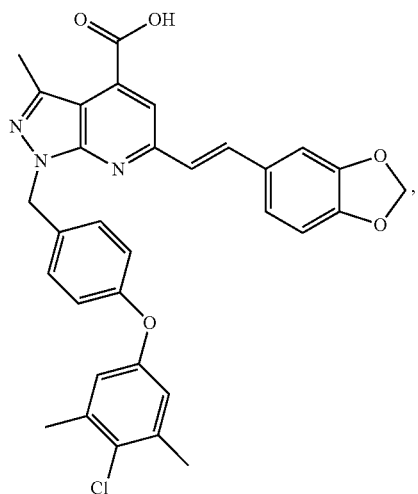

-continued

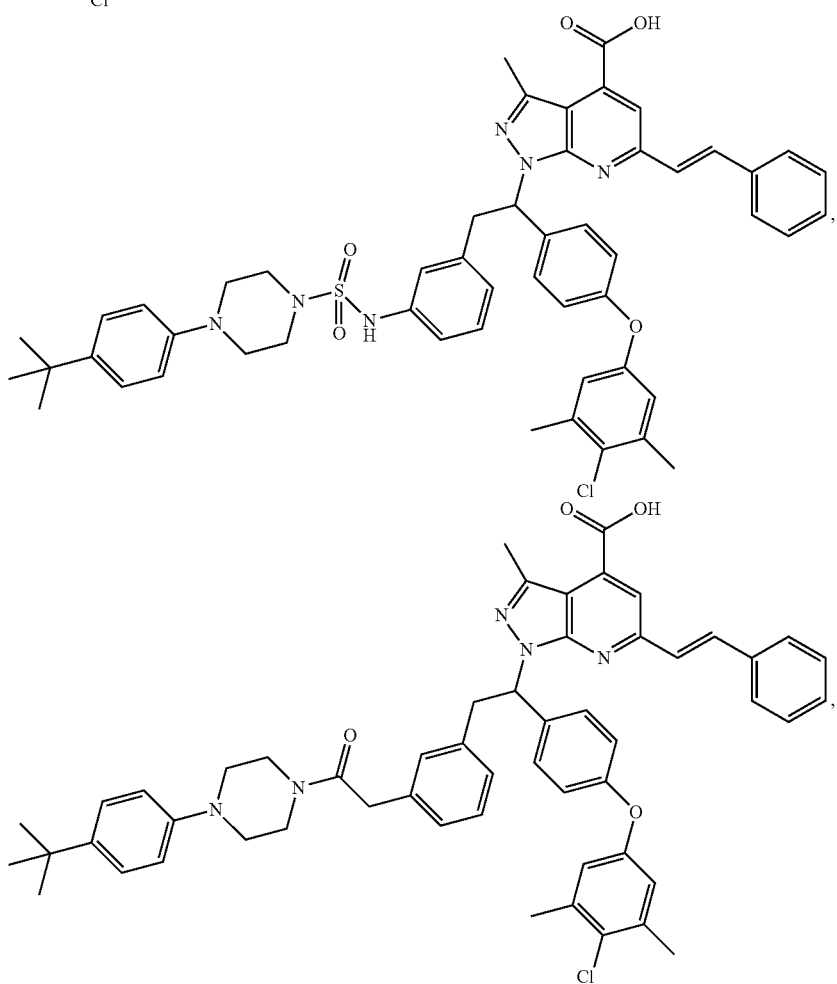

or a pharmaceutically acceptable salt, solvate, or prodrug thereof.

An important aspect of the present invention is that compounds of the invention induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The Mcl-1 inhibitors of the present invention (e.g., pyrazolopyridine compounds) can be used to induce apoptosis in any disorder that can be treated, ameliorated, or prevented by the induction of apoptosis. In one embodiment, the inhibitors can be used to induce apoptosis in cells comprising functional Mcl-1 and/or Mcl-1-related proteins.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents. In other embodiments, the disorder is any disorder having cells having Mcl-1 protein and/or Mcl-1-related protein expression.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is a anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 2 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 2

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d] pyrimidin-4-one monosodium salt) | Zyloprim | GlaxoSmithKline, Research Triangle Park, NC |
| Altretamine (N,N,N',N',N'',N'',-hexamethyl-1,3,5-triazine-2, 4, 6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0, 0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |

TABLE 2-continued

| | | |
|---|---|---|
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S, 3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R, 3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S, 10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |

TABLE 2-continued

| | | |
|---|---|---|
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3, 17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2', 2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5, 12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis )) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3', 4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4 -Triazol-1-ylmethylene) dibenzonitrile) | Femara | Novartis |
| Leucovorin (L-Glutamic acid, N[4[[(2amino-5-formyl1,4,5,6,7,8 hexahydro4oxo6-pteridinyl)methyl]amino]benzoyl], calcium salt (1:1)) | Wellcovorin, Leucovorin | Immunex, Corp., Seattle, WA |

TABLE 2-continued

| | | |
|---|---|---|
| Levamisole HCl<br>((-)-(S)-2,3,5, 6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine<br>(1-(2-chloro-ethyl)-3-cyclohexyl-1-nitrosourea) | CeeNU | Bristol-Myers Squibb |
| Meclorethamine, nitrogen mustard<br>(2-chloro-N-(2-chloroethyl)-N-methylethanamine hydrochloride) | Mustargen | Merck |
| Megestrol acetate<br>17α(acetyloxy)-6-methylpregna-4,6-diene-3,20-dione | Megace | Bristol-Myers Squibb |
| Melphalan, L-PAM<br>(4-[bis(2-chloroethyl) amino]-L-phenylalanine) | Alkeran | GlaxoSmithKline |
| Mercaptopurine, 6-MP<br>(1,7-dihydro-6H -purine-6-thione monohydrate) | Purinethol | GlaxoSmithKline |
| Mesna<br>(sodium 2-mercaptoethane sulfonate) | Mesnex | Asta Medica |
| Methotrexate<br>(N-[4-[[(2,4-diamino-6-pteridinyl)methyl]methylamino]benzoyl]-L-glutamic acid) | Methotrexate | Lederle Laboratories |
| Methoxsalen<br>(9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane<br>(1,1-dichloro-2-(o-chlorophenyl)-2-(p-chlorophenyl) ethane) | Lysodren | Bristol-Myers Squibb |
| Mitoxantrone<br>(1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin<br>(IL-11) | Neumega | Genetics Institute, Inc., Alexandria, VA |
| Oxaliplatin<br>(cis-[(1R,2R)-1,2-cyclohexanediamine-N,N'] [oxalato(2-)-O,O'] platinum) | Eloxatin | Sanofi Synthelabo, Inc., NY, NY |
| Paclitaxel<br>(5β, 20-Epoxy-1,2a, 4,7β, 10β, 13a-hexahydroxytax-11-en-9-one 4,10-diacetate 2-benzoate 13-ester with (2R, 3 S)-N-benzoyl-3-phenylisoserine) | TAXOL | Bristol-Myers Squibb |
| Pamidronate<br>(phosphonic acid (3-amino-1-hydroxypropylidene) bis-, disodium salt, pentahydrate, (APD)) | Aredia | Novartis |
| Pegademase<br>((monomethoxypolyethylene glycol succinimidyl) 11-17-adenosine deaminase) | Adagen<br>(Pegademase Bovine) | Enzon Pharmaceuticals, Inc., Bridgewater, NJ |
| Pegaspargase<br>(monomethoxypolyethylene glycol succinimidyl L-asparaginase) | Oncaspar | Enzon |
| Pegfilgrastim<br>(covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin<br>(antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine<br>(N-isopropyl-μ-(2-methylhydrazino)-p-toluamide monohydrochloride) | Matulane | Sigma Tau Pharmaceuticals, Inc., Gaithersburg, MD |

TABLE 2-continued

| Drug | Brand | Company |
|---|---|---|
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3- propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2- thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3', 4': 6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl- | Zometa | Novartis |

TABLE 2-continued phosphonoethyl) phosphonic acid monohydrate)

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

Preliminary experiments regarding pyrazolopyridine compounds are provided in U.S. Provisional Patent No. 61/975,297, filed Apr. 4, 2014.

Example 2

This example describes the development of 1H-pyrazolo [3,4-b]pyridine analogs as a class of Mcl-1 inhibitors.

High throughput screen (HTS) approach is a known strategy for identification of potential lead compounds for further development (see, e.g., Macarron, R., et al., Nat Rev Drug Discov 2011, 10, 188-95). To identify small-small molecule Mcl-1 inhibitors, a dual-readout HTS assay that combines two assay technologies, fluorescence polarization (FP) and Forster resonance energy transfer (FRET), was developed, optimized and miniaturized to a 1,536-well ultra-HTS format (see, e.g., Du, Y., et al., Assay Drug Dev Technol 2011, 9, 382-93). The assay was used to screen a library of 102,255 compounds at Emory University Molecular Libraries Screening Center using recombinant Mcl-1 and either a labeled Noxa or Bid BH3 derived peptides. The identified hits from the both primary screens were subjected to secondary dose-response tests and a total of 1214 (875 from Mcl-1/Noxa and 509 from Mcl-1/Bid) including 170 overlapping compounds were identified. All the dose-response curves were further deposited in the PubChem's BioAssay Database under AID 1417 (see, e.g., http:// (followed by) pubchem.ncbi.nlm. (followed by) nih.gov/assay/assay.cgi?aid=1417) and 1418 (see, e.g., http://(followed by) pubchem.ncbi.nlm. (followed by) nih.gov/assay/assay.cgi?aid=1418).

A high hit rate in HTS campaigns can make the identification of the most promising hits a challenging task and thus novel strategies to simplify this process are desired. Therefore, an integrated screening approach was employed by combining in silico target-based screening for selection of the most promising hits. For this purpose, molecular docking using the crystal structure of Mcl-1 bound to mNoxa (PDB 2NLA) (see, e.g., Czabotar, P. E. et al., Proc Natl Acad Sci USA 2007, 104, 6217-22) was utilized and all identified hits were subjected to Schrödinger's Induced Fit Docking (IFD) protocol (see, e.g., Schrödinger Suite 2011 Induced Fit Docking protocol; Glide version 5.7, Schrödinger, LLC, New York, N.Y., 2009; Prime version 3.0, Schrödinger, LLC, New York, N.Y. 2011) at the BH3 binding site of Mcl-1. A pharmacophore model (FIG. 1) was developed based on the interactions of mNoxa and Mcl-1 which included 3 hydrophobic and one hydrogen bond/electrostatic interactions. Compounds able to mimic at least two of the 4 conserved interactions of mNoxa with Mcl-1 were selected. This totaled 67 compounds from which 48 were purchased from commercial vendors. All 48 compounds were subjected to rigorous biochemical and biophysical assays which included dose-response competitive FP and SPR assays against Mcl-1 and HSQC NMR studies. Compounds which gave consistent results in all the binding assays were considered as validated hits and those with promising chemical scaffolds were selected for further optimization.

Example 3

This example describes the identification of HTS lead 1 as a Mcl-1 inhibitor. Compound 1

Figure 2:
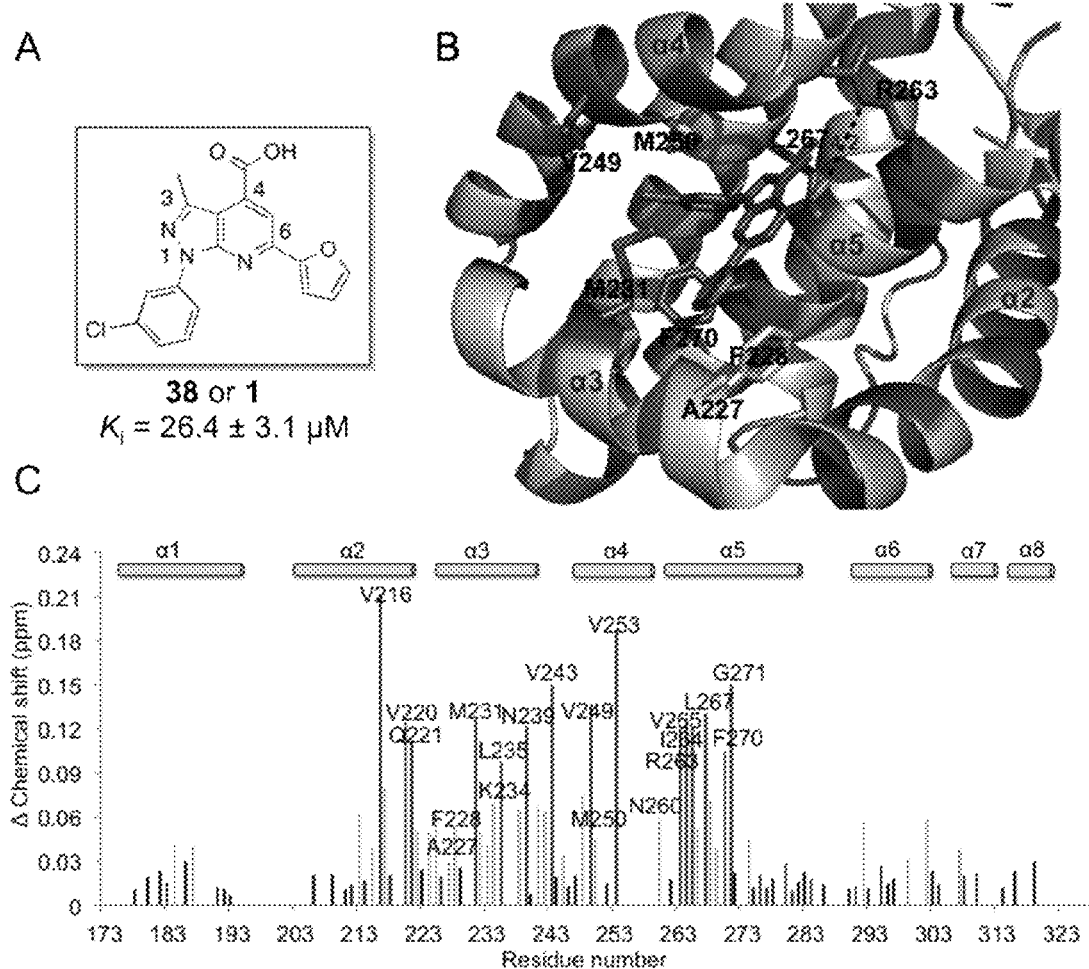
FIG. 2 shows a docking and NMR studies of compound 1. (A) Structure of the HTS lead compound 1 (note that while FIG. 2 recites "38 or 1", the intended compound is compound 1 (B) "Grey-scaled" putative binding mode of compound 1 to Mcl-1 (4HW2). The surface of Mcl-1 is "grey-scaled" colored according to the chemical shift intensity. Residues of Mcl-1 labeled in black are predicted to interact with 1. (C) Plot of chemical shift changes of Mcl-1 amide upon addition of compound 1 (Mcl-1:1 ratio of 1:2) as a function of Mcl-1 residue numbers. Color legend: Significant shift (>0.09 ppm) is represented with V216, V220, C221, M231, L235, N239, V243, V253, R263, I264, V265, L267, F270, G271, moderate shift (≥0.03 ppm and ≤0.09 ppm) represented with F227, F228, K234, M250, N260.

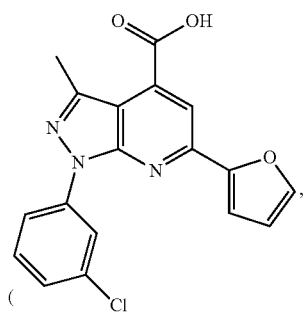 [SMILES: Cc1nn(-c2cccc(Cl)c2)c2nc(-c3ccco3)cc(C(=O)O)c12]

see, also, FIG. 2A (note that while FIG. 2 recites "38 or 1", the intended compound is compound 1

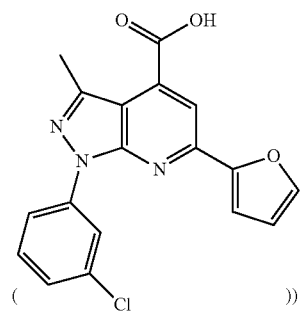 [SMILES: Cc1nn(-c2cccc(Cl)c2)c2nc(-c3ccco3)cc(C(=O)O)c12]

was one of the validated hits which showed dose-dependent chemical shift changes of Mcl-1 residues in HSQC NMR experiments. Compound 1 was resynthesized (analog 1) and its potency was confirmed ($K_i$=2.64 μM). The simplicity of synthetic modification for its analog generation as well as its drug-like features as defined by Lipinski's Rule of Five (see, e.g., Lipinski, C. A. et al., Adv Drug Deliv Rev 2001, 46, 3-26) made it a good choice for further optimization. 1 has a favorable ligand efficiency of 12.9 which is calculated based on the following equation:

$$LE = \frac{pK_i}{MW \text{ (kDa)}}.$$

Ligand efficiency (LE) as calculated is also referred to as binding efficiency index (BEI) (see, e.g., Abad-Zapatero, C., et al., Drug Discov Today 2005, 10, 464-9, Hajduk, P. J., J. Med Chem 2006, 49, 6972-6).

For docking studies of 1, a reported Mcl-1 crystal structure in complex with a synthetic ligand (PDB 4HW2) was utilized (see, e.g., Friberg, A., et al., J Med Chem 2013, 56, 15-30). The Gold-generated docking pose (FIG. 2B) of 1 was further validated and confirmed by HSQC NMR studies of Mcl-1 in presence of 2-fold excess of 1. Chemical shift perturbation (CSP) plot of compound 1 (FIG. 2C) showed moderate to significant perturbations of V249, M250 and M231, which are part of the p2 pocket of Mcl-1, consistent with the predicted binding model where 3-chlorophenyl of 1 binds to p2 hydrophobic pocket. Significant perturbations of L267 and R263 as well as residues in their vicinity (I264, V265) are also observed. L267 is predicted to interact with the 3-methyl while R263 forms an electrostatic interaction with 4-carboxylic acid of 1. Finally, the 6-furyl is predicted to interact with residues in the p2/p3 pockets, mainly A227, F228, F270, G271, and M231 which are moderately to significantly perturbed. In addition to the residues mentioned above which are predicted to interact with 1 by docking studies, significant chemical shift perturbations of V216, V220, Q221 (on C-terminal of α-helix 2), K234, L235 (on C-terminal of α-helix 3), N239 (on the disordered loop connecting α-helix 3 and 4) and V243 and V253 (on α-helix 4) are observed. Overall analysis of the chemical shift changes of 1 in complex with Mcl-1 shows that 1 affects the residues in the BH3-binding groove of Mcl-1 and provides a strong support for the binding of this compound to Mcl-1.

The strong evidence of binding of 1 to Mcl-1 based on computational studies supported by NMR gave confidence to undertake the optimization of this class of compounds utilizing structure-based design strategy. Therefore an SAR plan was devised to make changes to the N-1 and C-6 aryl positions denoted as R and R' respectively (Scheme 1).

Example 4

This example describes the synthesis of 1,6-disubstituted-3-methyl-pyrazolopyridine-4-carboxylic acid analogs.

A short, efficient and convergent synthesis of 1 class analogs was established based on literature methodology with the majority of compounds made utilizing Scheme 1.

Scheme 1. Generation of 1,6-disubstituted-3-methyl-pyrazolopyridine-4-carboxylic acid analogs[a].

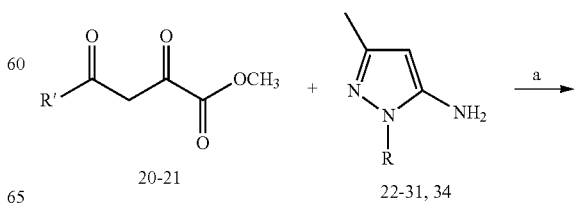

-continued

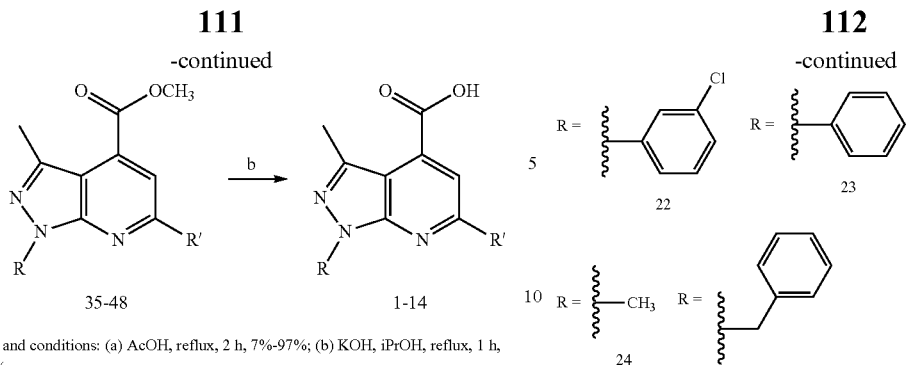

35-48 → 1-14

[a]Reagents and conditions: (a) AcOH, reflux, 2 h, 7%-97%; (b) KOH, iPrOH, reflux, 1 h, 20%-100%.

Acyl pyruvates 20 and 21 were obtained by Claisen condensation of 2-acetyl furan or acetone and diethyl oxalate (see, e.g., Ghosh, A. K., et al., J Med Chem 2005, 48, 6767-71) (Scheme 2). This introduced the first diversity point of the library which is termed R'.

Scheme 2. Synthesis of acylpyruvates 20 and 21[a].

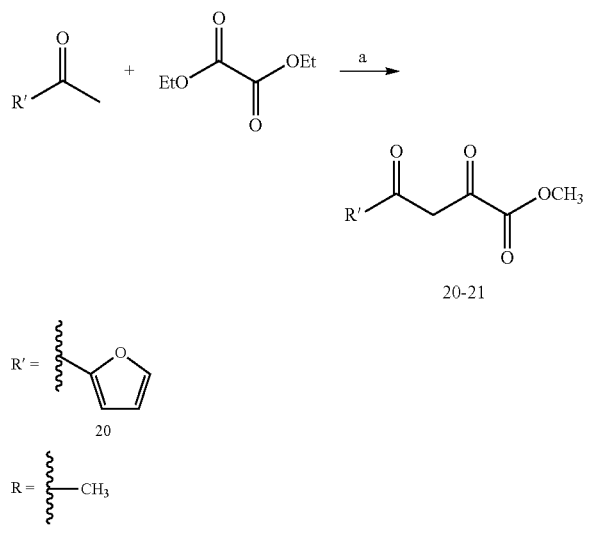

[a]Reagents and conditions: (a) Na, MeOH, rt, 1 h, 26%-35%.

The second diversity point (R) was introduced with varying substitutions at the pyrazole N-1 position. Two sets of aminopyrazoles were prepared by two distinct approaches. The first series of aminopyrazoles (22-25) were obtained from a Michael addition of substituted hydrazines to 3-aminocrotononitrile (see, e.g., Ganesan, A., et al., Journal of Organic Chemistry 1993, 58, 6155-6157) (Scheme 3.3).

Scheme 3. Synthesis of aminopyrazoles 22-25 from substituted hydrazines[a].

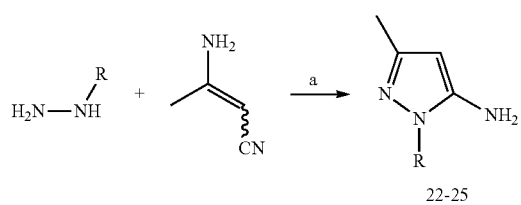

[a]Reagents and conditions: (a) 1N HCl, reflux, 3 h, 20%-98%.

For analog 11 (311), the substituted hydrazine (33) was not available but was easily prepared (Scheme 4) by alkylation of 1-phenol by 1,3-dibromopropane (see, e.g., Martins, A., et al., J Org Chem 2006, 71, 4937-42) followed by displacement of bromide with hydrazine (see, e.g., WO2003027074A1).

Scheme 4. Synthesis of aminopyrazole 34[a].

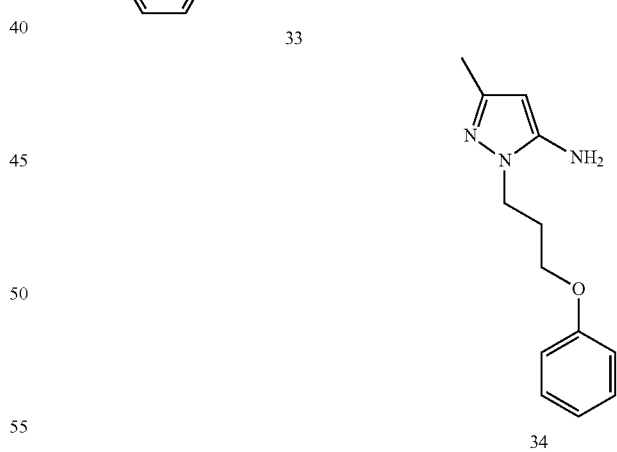

[a]Reagents and conditions: (a) Br(CH$_2$)$_3$Br, K$_2$CO$_3$, acetone, reflux, 19 h, 77%; (b) H$_2$NNH$_2$·H$_2$O, EtOH, 80° C., 3 h 30 min; (c) 2N HCl, CH$_2$Cl$_2$, rt, overnight; (d) H$_2$N(CH$_3$)═CHCN, 1N HCl, reflux, 3 h, 48% over three steps.

When the substituted hydrazines were not commercially available or easily accessible, the multicomponent condensation of hydrazine, crotononitrile and arylaldehyde afforded the desired aminopyrazoles (26-31) (Scheme 5) as reported previously (see, e.g., Misra, R. N., et al., Bioorg Med Chem Lett 2003, 13, 1133-6; see, also, WO2009150614A1). The proposed mechanism by which this reaction works is as following: first, the Michael adduct is formed between reaction of crotononitrile and hydrazine. Treatment of this adduct with a desired arylaldehyde provides the intermediate imine (structure shown) which is not isolated, but is directly converted to the corresponding pyrazole via base-promoted cyclization and isomerization (Scheme 5). Having the desired acylpyruvates and aminopyrazoles in hand, the penultimate intermediates (35-48) were obtained from the reaction between these two building blocks in acetic acid (see, e.g., Volochnyuk, D. M., et al., J Comb Chem 2010, 12, 510-7) (Scheme 1). Hydrolysis of ester using potassium hydroxide in 2-propanol provided the final analogs 1-14 (see, e.g., Volochnyuk, D. M., et al., J Comb Chem 2010, 12, 510-7) (Scheme 1).

Scheme 5. Synthesis of aminopyrazoles 26-31 from aryladehydes[a].

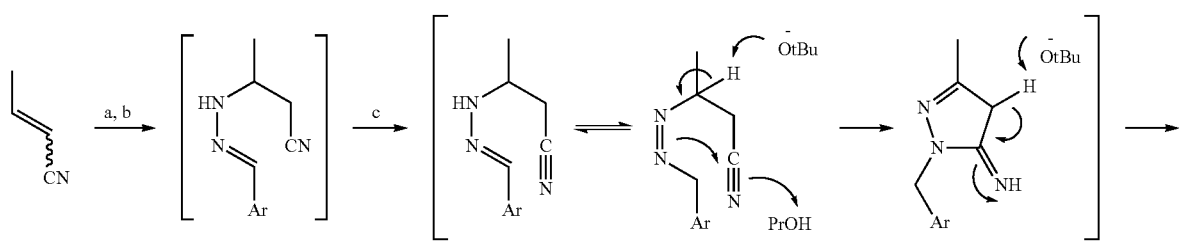

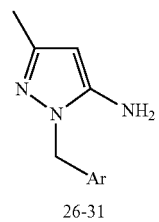

26-31

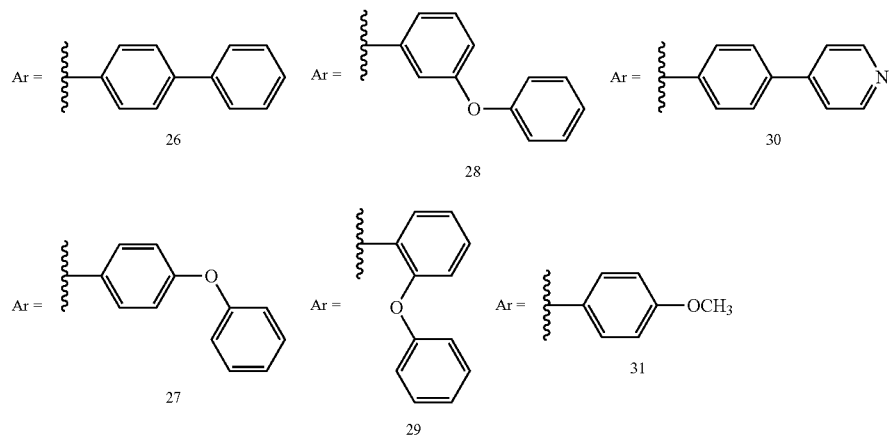

[a]Reagents and conditions: (a) H$_2$NNH$_2$•H$_2$O, THF, 40° C., 2 h; (b) ArCHO, 40° C., 2 h (c) t-BuONa, iPrOH, 100° C., 2 h 30 min or t-BuONa, n-PrOH, 110° C., 2 h 30 min, 20%-42% over three steps.

For analogs 15-19, Scheme 6 was utilized. 3-methyl-1-(4-phenoxybenzyl)-1H-pyrazol-5-amine (28) was condensed with diethyl oxalacetate to provide ring-opened intermediate (structure not shown) which was cyclized to pyridinol 49 by refluxing in glacial acetic acid (see, e.g., Neres, J., et al., J Med Chem 2013, 56, 2385-405). Chlorination of pyridone 49 with POCl$_3$ was not successful as previously reported (see, e.g., Neres, J., et al., J Med Chem 2013, 56, 2385-405). Neither did the use of a stoichiometric amount of Vilsmeier reagent under mild conditions yield the desired product. However, use of a large excess of Vilsmeier reagent under reflux conditions (see, e.g., Sercel, A. D., et al., Synthetic Communications 2007, 37, 4199-4208) overnight cleanly provided 50 in high yield. Intermediate 50 then underwent Pd-catalyzed carbon-carbon coupling reactions (see, e.g., Greig, I. R., et al., J Med Chem 2006, 49, 7487-92; Li, X., et al., J Med Chem 2003, 46, 5663-73; Dai, W., et al., Org Lett 2006, 8, 4665-7) with phenylvinylboronic acid or phenylacetylene to provide 52 and 53 respectively. Intermediate 54 was obtained via hydrogenation (see, e.g., WO2013039988A1) of 52. Direct amination (see, e.g., WO2013039988A1) of 50 with 2-aminomethylfuran or 4-(2-aminoethyl)morpholine under high temperature and long reaction time provided 51 and 55 respectively. Ester intermediates were hydrolyzed as previously described in Scheme 1 to provide acid analogs 15-19.

Scheme 6. Generation of analogs 15-19[a].

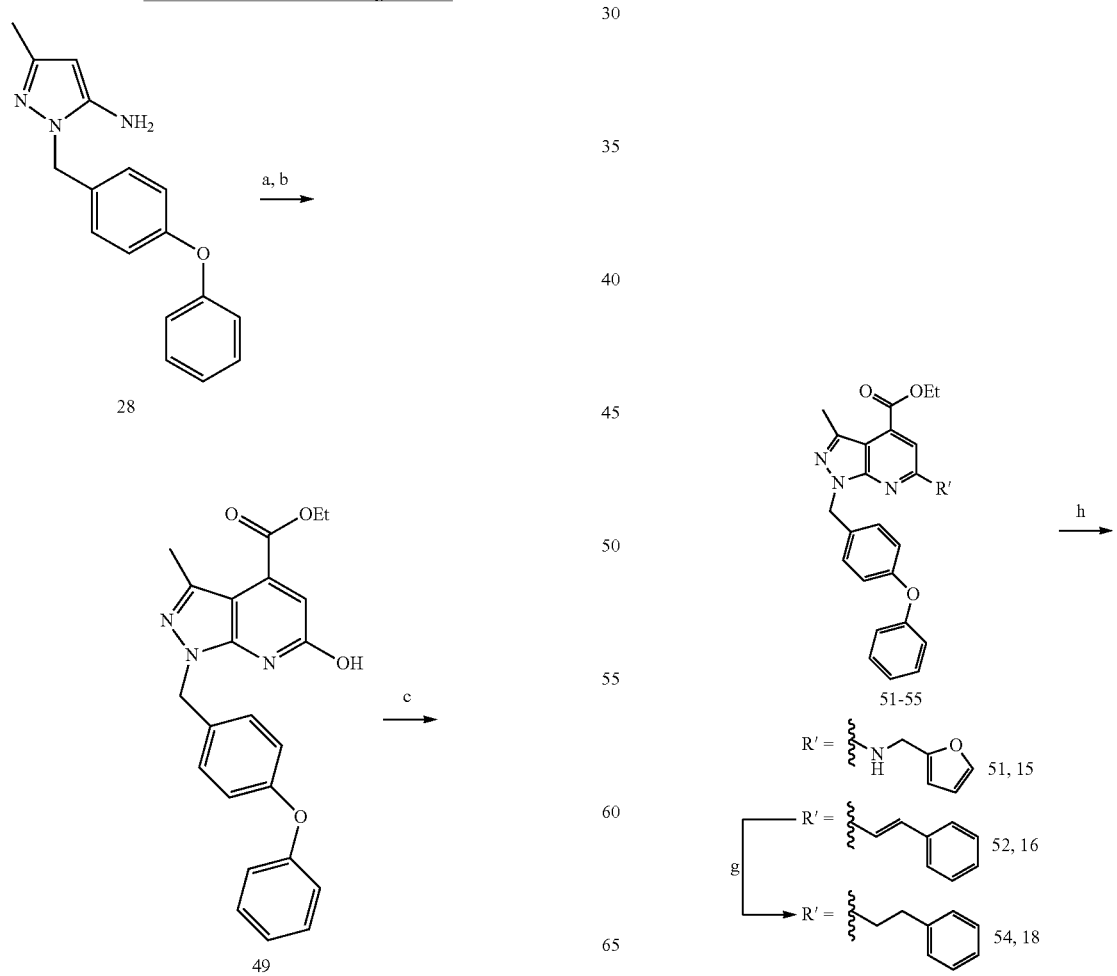

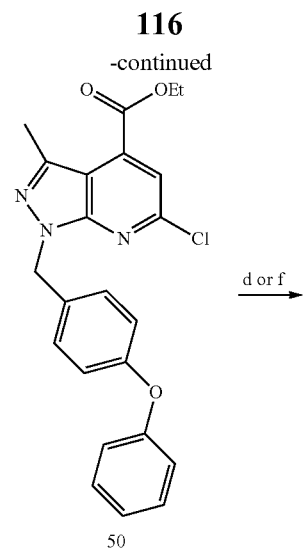

-continued

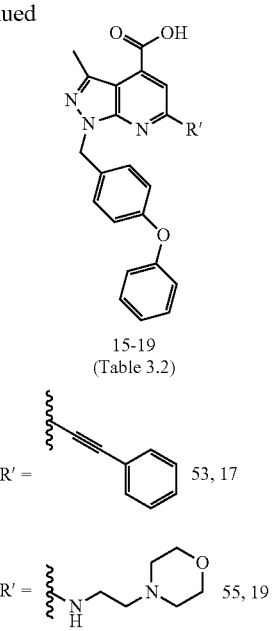

15-19
(Table 3.2)

R' = ⟶≡⟵⌬  53, 17

R' = ⟶N(H)CH2CH2–N(morpholine)  55, 19

*a*Reagents and conditions: (a) EtO$_2$CC(ONa)=CHCO$_2$Et, toluene/glacial AcOH/H$_2$O, 80° C., overnight; (b) glacial AcOH, reflux, 2 h, 67% over two steps; (c) (COCl)$_2$, DMF, 1,2 DCE, 0° C. to rt to reflux, overnight, quantitative; (d) for 52: phenylvinylboronic acid, Pd(PPh$_3$)$_4$, Na$_2$CO$_3$, 1,4 dioxane/H$_2$O, 90° C., overnight, 90% or for 53: phenylacetylene, Pd(PPh$_3$)$_2$Cl$_2$, CuI, Et$_3$N/THF, 60° C., overnight, 31%; (f) for 51: 2-aminomethylfuran, iPrOH, 100° C. to 150° C., 2 days, 30% or for 55: 4-(2-aminoethyl)morpholine, iPrOH/NMP, 150° C., overnight, 26%; (g) Pd/C, H$_2$ (1 atm), EtOH/THF, rt, overnight, 84%; (h) KOH, iPrOH/THF, reflux, 2 h, 39%-94% or for 15: 1N NaOH, THF, reflux, 3 h, 61%.

Example 5

This example describes structure-activity relationships of the compounds.

Figure 3:
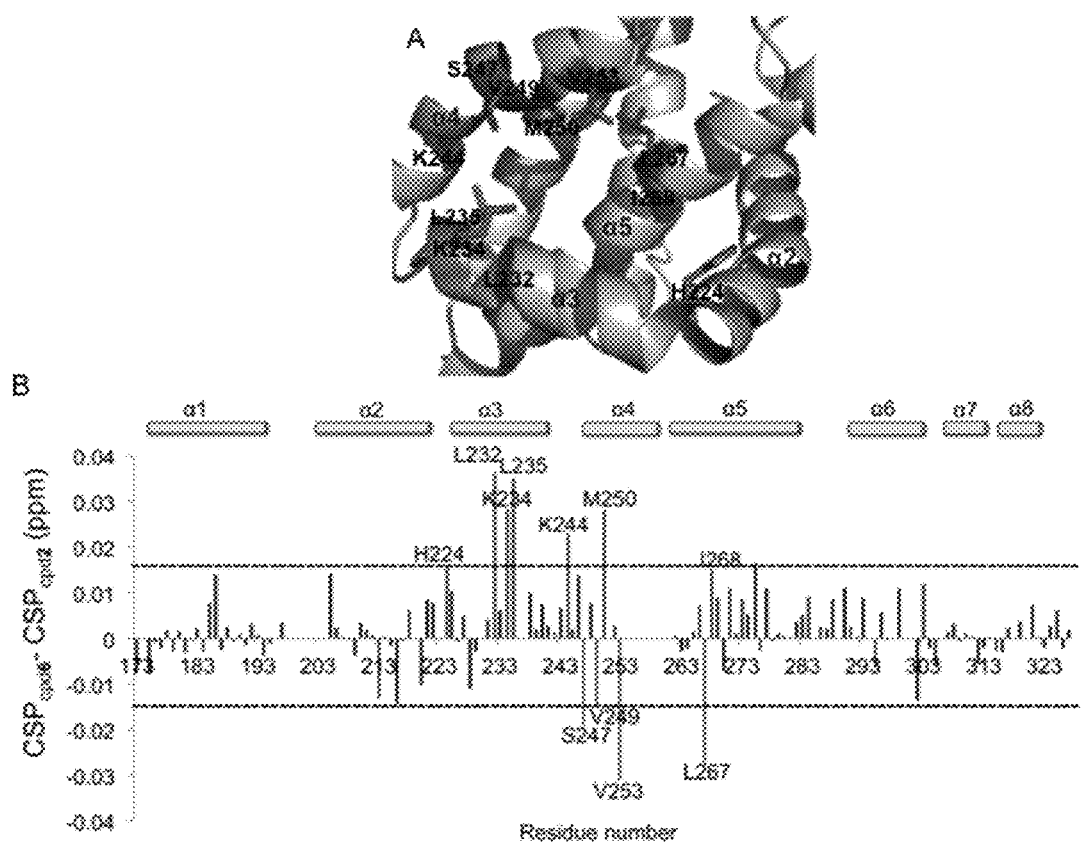
FIG. 3 shows a mapping the binding site of R' substituent. (A) Residues of Mcl-1 (PDB 4HW2) perturbed significantly in presence of 6 ("grey-scaled" medium tone of grey) and 2 ("grey-scaled" darkest tone of grey) are shown and labeled. (B) Chemical shift perturbation (CSP) difference plot as generated by subtraction of CSP of 2 from 6 (Mcl-1:cpd ratio of 1:2). Significant CSP difference of >−0.015 ppm is highlighted (S247, V249, V253, L267) and >0.015 ppm is highlighted (H224, L232, K234, L235, K244, M250, I268).

In an absence of a crystal structure of 1 with Mcl-1, the contributions of R and R' of 1 were studied to gain further insight into their binding sites by systematically removing each group and study the obtained fragments (Table 1) in HSQC NMR. First, analog 2 was synthesized in which a phenyl was substituted for the 3-chlorophenyl which led to 2-fold decrease in potency compared to 1. Subsequently removal of either the phenyl at R or the furyl at R' or both, and their replacements with a methyl to give fragments 3-5 respectively, were studied. Analogs 3 and 5 did not bind up to 200 µM and showed little to no perturbations in HSQC NMR studies at 2-fold excess (final fragment concentration of 150 µM). Analog 4 showed seven-fold decrease in comparison with compound 1, which together with the results for analogs 3 and 5 confirms the importance of both aromatic rings at R and R' and their contributions to the overall potency. Next, the phenyl in 2 was replaced with a benzyl group in 6 which led to a slight increase in potency. More importantly, the NMR studies (FIG. 2) of these two analogs led to an important finding. When the chemical shift changes of 2 were subtracted from those caused by 6 and the residues were mapped onto the structure of Mcl-1 (FIGS. 3A and 3B), it became clear that the residues most affected by the changes between the two structures, mainly clustered on the C-terminal of α-helix 3 and α-helix 4, which are the residues lining the p2 pocket of Mcl-1. This finding indicates that the benzyl group of 6 inserts into the h2 pocket and forms additional hydrophobic interactions with p2 pocket, further validating the molecular docking model in which R is predicted to insert into the p2 pocket of Mcl-1.

TABLE 1

Binding affinities of 1 and its analogs against Mcl-1 protein

| Cpd | R' | R | IC$_{50}$ ± SD [µM] | K$_i$ ± SD [µM] | LE |
|---|---|---|---|---|---|
| 1 | 2-furyl | 3-chlorophenyl | 13.7 ± 2.4 | 2.64 ± 0.46 | 15.8 |
| 2 | 2-furyl | phenyl | 22.1 ± 4.5 | 4.25 ± 0.86 | 16.8 |
| 3 | 2-furyl | CH$_3$ | >200 | >40 | |

TABLE 1-continued

Binding affinities of 1 and its analogs against Mcl-1 protein

| Cpd | R' | R | IC$_{50}$ ± SD [μM] | K$_i$ ± SD [μM] | LE |
|---|---|---|---|---|---|
| 4 | CH$_3$ | phenyl | 75.7 ± 12.6 | 14.58 ± 2.42 | 18.1 |
| 5 | CH$_3$ | CH$_3$ | >200 | >40 | |
| 6 | 2-furyl | benzyl | 18.4 ± 9.9 | 3.54 ± 1.90 | 16.4 |
| 7 | 2-furyl | 4-biphenylmethyl | 7.3 ± 0.8 | 1.40 ± 0.15 | 14.3 |
| 8 | 2-furyl | 4-phenoxybenzyl | 1.52 ± 0.5 | 0.29 ± 0.09 | 15.4 |
| 9 | 2-furyl | 3-phenoxybenzyl | 7.3 ± 0.2 | 1.40 ± 0.04 | 13.8 |
| 10 | 2-furyl | 2-phenoxybenzyl | 10.7 ± 2.4 | 2.06 ± 0.46 | 13.4 |
| 56 | 2-furyl | 4-(4-fluorophenoxy)benzyl | 4.68 ± 2.7 | 0.90 ± 0.46 | 13.6 |

TABLE 1-continued

Binding affinities of 1 and its analogs against Mcl-1 protein

| Cpd | R' | R | IC$_{50}$ ± SD [μM] | K$_i$ ± SD [μM] | LE |
|---|---|---|---|---|---|
| 57 | 2-furyl | 4-(4-chloro-3,5-dimethylphenoxy)benzyl | 0.67 ± 0.08 | 0.13 ± 0.01 | 14.1 |
| 58 | 2-furyl | 4-(naphthalen-1-yloxy)benzyl | 1.28 ± 0.48 | 0.25 ± 0.09 | 13.9 |
| 59 | 2-furyl | 4-phenoxybenzyl | 4.27 ± 1.21 | 0.82 ± 0.23 | 14.8 |
| 14 | CH$_3$ | 4-phenoxybenzyl | 17.26 ± 1.29 | 3.32 ± 0.25 | 14.7 |
| 15 | NH-CH$_2$-(2-furyl) | 4-phenoxybenzyl | 12.4 ± 3.04 | 2.39 ± 0.58 | 12.4 |
| 16 | (E)-styryl | 4-phenoxybenzyl | 1.11 ± 0.22 | 0.21 ± 0.04 | 14.5 |
| 17 | phenylethynyl | 4-phenoxybenzyl | 6.3 ± 0.69 | 1.21 ± 0.13 | 12.9 |
| 18 | 2-phenylethyl | 4-phenoxybenzyl | 2.54 ± 0.78 | 0.49 ± 0.15 | 13.6 |

TABLE 1-continued

Binding affinities of 1 and its analogs against Mcl-1 protein

| Cpd | R' | R | IC$_{50}$ ± SD [μM] | K$_i$ ± SD [μM] | LE |
|---|---|---|---|---|---|
| 55 | 4-F-phenyl | 4-phenoxybenzyl | 10.85 ± 1.57 | 2.09 ± 0.30 | 12.5 |
| 60 | phenyl | 4-phenoxybenzyl | 7.97 ± 2.80 | 1.53 ± 0.54 | 13.4 |
| 61 | 2-thienyl | 4-phenoxybenzyl | 6.76 ± 0.80 | 1.30 ± 0.15 | 13.3 |
| 62 | 4-F-phenyl | 4-(4-F-phenoxy)benzyl | 4.51 ± 1.20 | 0.88 ± 0.24 | 12.8 |

Figure 4:
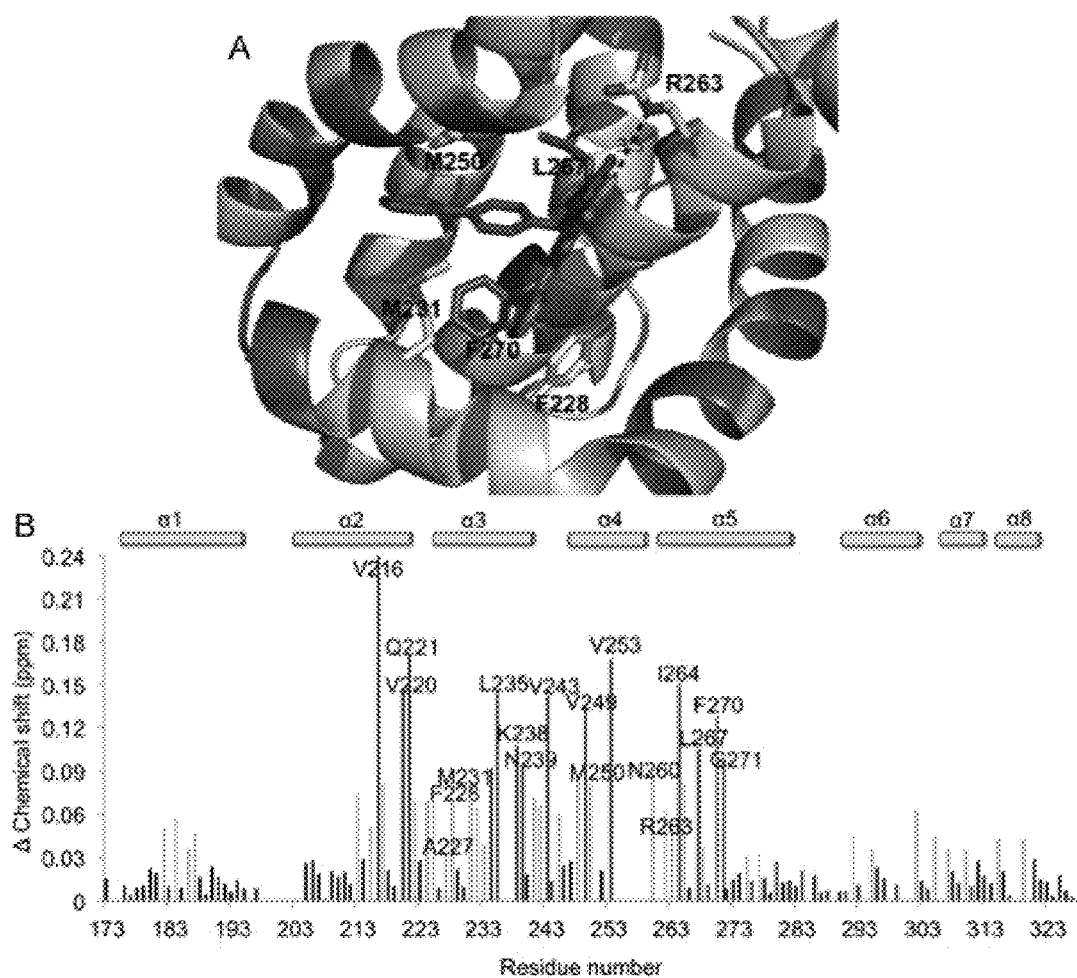
FIG. 4 shows docking and NMR studies of 7. (A) Putative binding modes of 7 to Mcl-1 (4HW2). The surface of Mcl-1 is "grey-scaled" colored according to the chemical shift intensity. Residues of Mcl-1 labeled in black are predicted to interact with 7. (B) Plot of chemical shift changes of Mcl-1 amide upon addition of 7 (Mcl-1:7 ratio of 1:2) as a function of Mcl-1 residue numbers. "Grey-scaled" color legend: Significant shift (>0.09 ppm) is represented with "grey-scaled" purple (V216, Q221, V220, L235, K238, N239, V243, V249, V253, I264, L267, F270, G271), moderate shift (≥0.03 ppm and ≤0.09 ppm) represented with "grey-scaled" pink (A227, F228, M231, N260, R263).

To further optimize the hydrophobic interactions in p2 pocket, para-biphenylmethyl and para-phenoxybenzyl were introduced at R in 7 and 8, which exhibited K$_i$ of 1.4 μM and 0.29 μM, respectively, and an overall 10-fold improvement over 1. The molecular docking of 7 places the para-biphenylmethyl deeper into the p2 pocket (FIG. 4A) which is supported by the NMR studies showing moderate to significant perturbations of F228, M250, and F270 of p2 pocket, clearly demonstrating the importance of the hydrophobic interactions in this sub-pocket (FIG. 4B).

Figure 5:
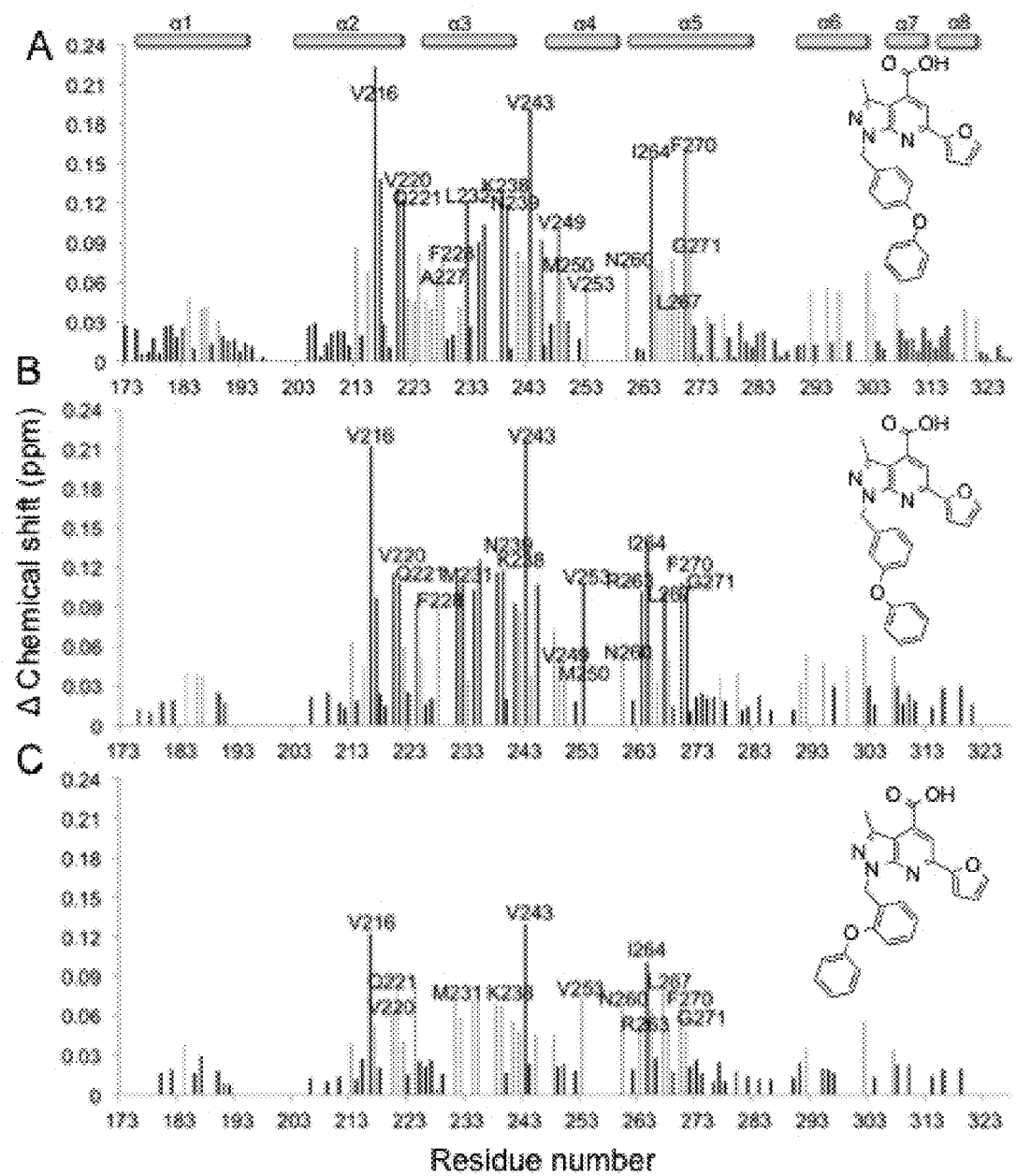
FIG. 5 shows NMR studies of 8, 9, 10. (A) Plots of chemical shift changes of Mcl-1 amide upon addition of 8 (Mcl-1:8 ratio of 1:2) (B) 9 (Mcl-1:9 ratio of 1:2) (C) 10 (Mcl-1:10 ratio of 1:2) as a function of Mcl-1 residue numbers. Legend: Significant shift (>0.09 ppm), moderate shift (≥0.03 ppm and ≤0.09 ppm).

The CSP plot of 8 (FIG. 5A) further confirmed its binding to Mcl-1. To examine how the position of the distal phenyl ring in R substituent will affect the binding, compounds with meta- (9) and ortho-phenoxybenzyl substituents (10) were synthesized. Analog 9 showed a 5-fold decrease in binding compared to 8 while 10 decreased binding by 10 fold indicating that there is a clear preference for the para-phenoxybenzyl in the pocket. The CSP plots derived from HSQC NMR (FIG. 5A-C) of these three isomers supported the binding affinity data with 8 and 9 showing the highest magnitude of perturbations of residues. In addition, CSP demonstrated that the phenoxybenzyl substituent was placed in the p2 pocket through the chemical shift perturbations of V249, M250 and M231. In addition residues A227, F228, F270, 8263 and L267 are perturbed suggesting that carboxylic acid forms a hydrogen bond interaction and the 6-furyl is placed in the p3 pocket. Further modifications on the distal phenyl ring in compound 8 led to the most potent compound 57 with K$_i$ value of 130 nM and overall binding affinity improvement of 20 fold in comparison with lead compound 1. Compounds presented in Table 1 exhibit an average binding efficiency index of 14.31±1.4 showing that the increasing of the molecular weight of the compounds through the optimization process kept the changes of BEI in a range of 10%, demonstrating that the chemical modifications contribute to the binding affinity.

Figure 6:
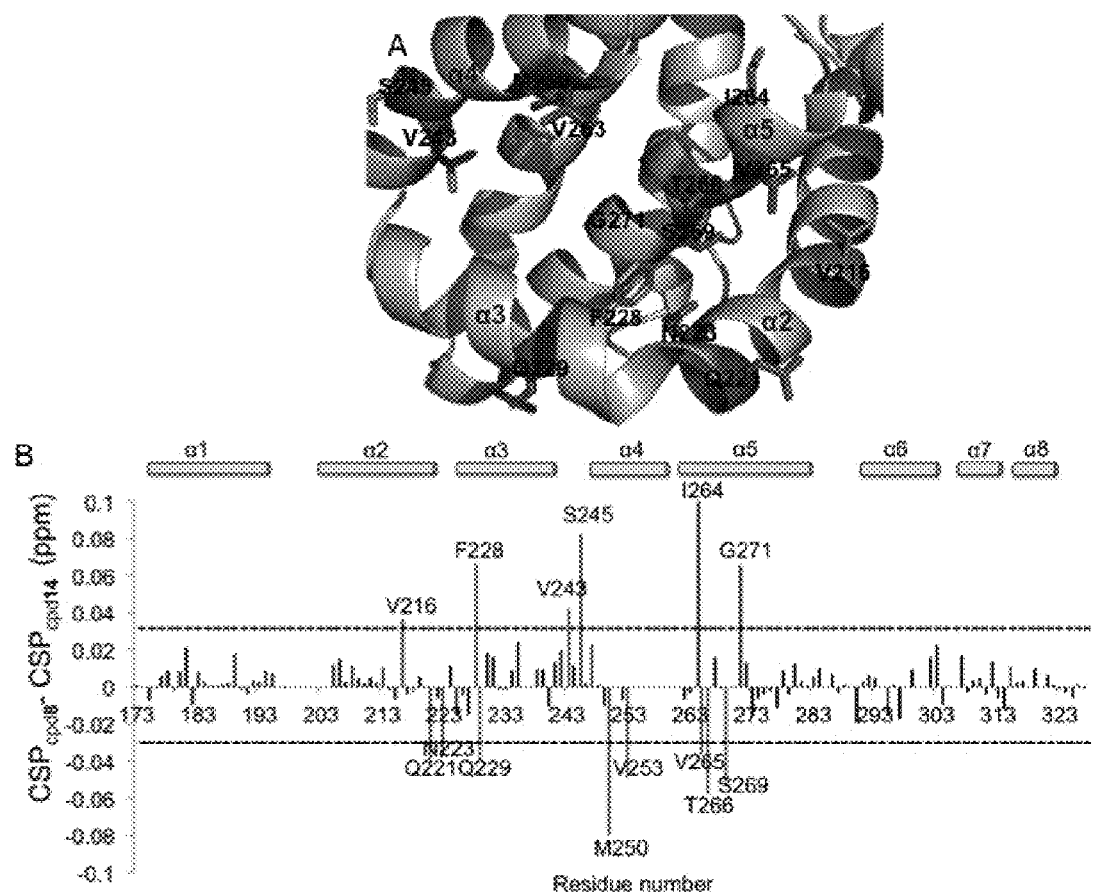
FIG. 6 shows a mapping the binding site of R' substituent. (A) "Grey-scaled" residues of Mcl-1 (PDB 4HW2) perturbed significantly in presence of 8 ("grey-scaled" green) and 14 ("grey-scaled" red) are shown and labeled. (B) Chemical shift perturbation (CSP) difference plot as generated by subtraction of CSP of 14 from 8 (Mcl-1:cpd ratio of 1:2). Significant CSP difference of >−0.03 ppm is highlighted in "grey-scaled" red and >0.03 ppm is highlighted in "grey-scaled" green.

Although studies with analogs 2 and 4 demonstrated that removal of furyl resulted in drop in binding affinity, to further determine the contribution of R' substituent, several additional analogs were synthesized by changing the R' substituent in the potent analog 8. Compound 14, where the furyl was replaced with a methyl, decreased binding by a significant 11 fold compared to 8 further highlighting the importance of the furyl to the overall binding. The CSP difference plot of 14 and 8 (FIG. 6) showed that the residues affected by the furyl are spread along α-helices 2 to 5. The reason for this wide area to be affected can be explained because of, for example, the nature of R' substituent. A furyl at R' of 8 is much larger than a methyl in 14, and its accommodation into the pocket requires conformational change by the protein which results in more perturbations.

Figure 7:
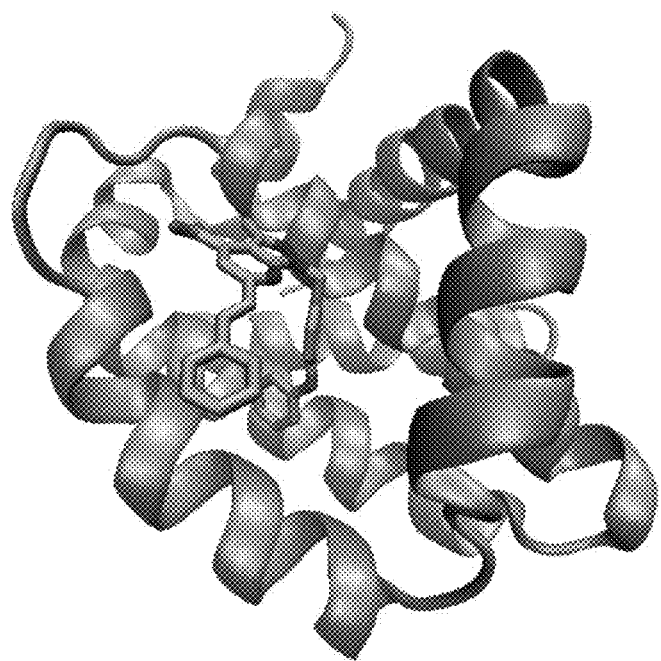
FIG. 7 shows X-ray complex structure of compound 16 and Mcl-1 protein (2.45 Å resolution).

Based on the docking poses of earlier analogs, while the furan was predicted to interact with residues in p3 pocket, its direct attachment to the bicyclic core made its placement in p3 pocket dependent on the R substituent. Therefore, incorporation of linkers to provide more degrees of freedom and a better placement in the p3 pocket were assessed. Attempts at homologation of the furyl group were not successful using our synthetic Scheme 3.1; however, using a different chemistry (Scheme 6), analog 15 with an aminomethyl furan at R' was obtained. This analog exhibited a $K_i$=2.39 μM and an 8-fold decrease in binding compared to 8. The decrease in binding affinity can be attributed to the introduction of a polar amine linker or an unfavorable direction of the furan ring in the p3 pocket. Next, analogs 16-18 with a phenyl in place of furyl and aliphatic linkers with different directional geometries were synthesized. All three analogs 16-18 have improved potencies compared to 15, which confirms that aliphatic linkers are preferred, and compound 16 showed slight improvement in the binding affinity in comparison to 8. Co-crystal structure of 16 bound to Mcl-1 was obtained at 2.45 Å resolution (FIG. 7). Compound 16 inserts its phenoxy group deeply into the hydrophobic pocket formed by L246, S247, M250 S293 and I294, while the adjacent phenyl ring is sandwiched between the side chains of M250 and F270 with F270 interacting via edge on π-π stacking. The methyl bridging with the pyrazole group makes additional van der waals contacts with F270. The guanidinium group on R263 forms bidentate hydrogen bonds with the carboxylic oxygens present on the pyridine ring. The phenyl group of the phenylethenyl does not interact with the BH3 binding site, while the trans ethenyl linker interacts with the side chains of M250 and M231.

Example 6

This example describes selectivity studies of the compounds.

The selectivity profile of the most potent analogs 8, 16, 57 and 58 was determined against two other Bcl-2 anti-apoptotic proteins (Bcl-2 and Bcl-$X_L$) utilizing a competitive FP-based assays, and $K_i$ values were calculated using equations developed previously (see, e.g., Nikolovska-Coleska, Z. et al., Anal Biochem 2004, 332, 261-73) (Table 2).

TABLE 2

Selectivity of selected analogs against Bcl-2 anti-apoptoticproteins.

| Cpd | Mcl-1<br>$K_i$ ± SD (μM) | Bcl-2*<br>$K_i$ ± SD (μM) | Bcl-$X_L$*<br>$K_i$ ± SD (μM) |
|---|---|---|---|
| 8 | 0.29 ± 0.09 | >4 | >5 |
| 16 | 0.21 ± 0.04 | 3.16 ± 1.03 | 3.55 ± 0.30 |
| 57 | 0.13 ± 0.01 | 1.95 ± 0.20 | >5 |
| 58 | 0.25 ± 0.09 | >4 | >5 |

*Compounds were tested up to 20 μM.

Analogs 8, 16, 57 and 58 inhibited Mcl-1 most potently with $K_i$ values from 0.13 μM to 0.29 μM. All compounds bind to Mcl-1 protein with more than 15-fold and 20-fold selectivity over Bcl-2 and Bcl-xL, respectively. The most potent compound, 57, selectively binds to Mcl-1, followed by 15 fold decreased binding affinity to Bcl-2 and not showing binding to Bcl-xL up to 20 μM.

Example 7

This example demonstrates that compound 57 binds and functions as an antagonist of Mcl-1 protein, and selectively kills Mcl-1-dependent cell lines, consistent with its binding affinity profile.

Figure 8:
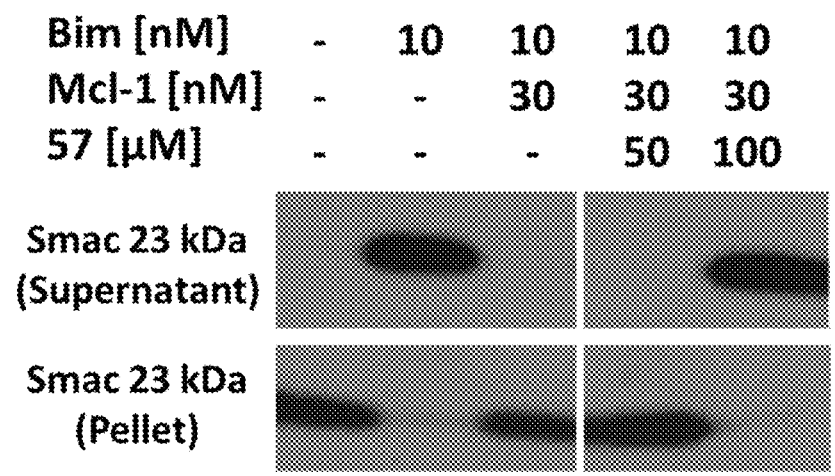
FIG. 8 presents recombinant functional assay demonstrating that compound 57 antagonizes the function of Mcl-1 protein.

To provide direct evidence that these Mcl-1 inhibitors also selectively antagonizes Mcl-1 function, a cell-free functional assay was established using purified mitochondria, recombinant Mcl-1, and the BIM BH3 peptide which binds to Mcl-1 protein with high affinities. At 10 nM the BIM BH3 peptide induces substantial release of Smac protein from mitochondria, and 30 nM of Mcl-1 completely inhibits this release (FIG. 8). 57 was shown to antagonize Mcl-1 and restore BIM-induced release of Smac protein from mitochondria at 100 μM. These data demonstrate that 57, binds and functions as antagonist of Mcl-1 protein.

Figure 9:
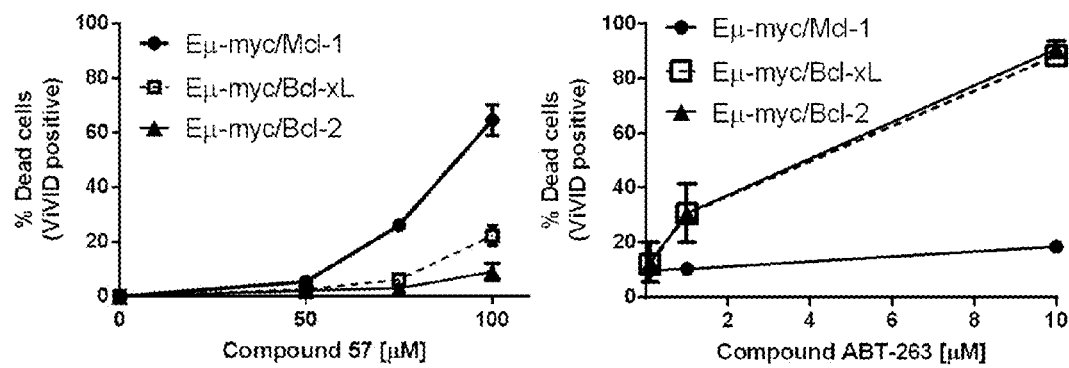
FIG. 9 shows selective killing of Eµ-myc lymphoma cells which survival depends on Mcl-1, but the growth of cells which depend on Bcl-2 and Bcl-xL is not affected by compound 57. In contrast, ABT-263, known Bcl-2/Bcl-xL inhibitor, kills only lymphoma cells that depend of these two proteins, but not the cells which depends on Mcl-1 protein.

The specificity and selectivity of this class Mcl-1 inhibitors was further confirmed by using cell lines developed by retroviral transduction of lymphoma cells isolated from Eμ-myc transgenic mice which survival depends on the expression of individual prosurvival protein (see, e.g., Whitecross K F, Alsop A E, Cluse L A, Wiegmans A, Banks K M, et al. 2009. Blood 113: 1982-91). 57 led to sensitization of Eμ-myc lymphomas overexpressing Mcl-1 but did not show effect on cells overexpressing Bcl-2 and Bcl-xL anti-apoptotic proteins, opposite of ABT-263 (FIG. 9). These data demonstrate that 57 selectively kills Mcl-1-dependent cell lines, consistent with its binding affinity profile.

Example 8

This example presents the experimental materials and methods utilized within Examples 1-4, and representative synthesis procedures.

Chemistry

All anhydrous reactions were run under an atmosphere of dry nitrogen. Reagents were used as supplied without further purification. Reactions were monitored by TLC using pre-coated silica gel 60 F254 plates. Silica gel chromatography was performed with silica gel (220-240 mesh) obtained from Silicycle. Purities of final compounds were assessed by analytical HPLC performed on a Shimadzu system with a Restek Ultra C18 (4.6×150 mm, 5 μm particle size) column or an Agilent 1100 series with an Agilent Zorbax Eclipse Plus-C18 column and a gradient of acetonitrile with 0.1 vol % TFA (10-90%) in water with 0.1 vol % TFA. All NMR spectra were obtained in DMSO-$d_6$ or $CDCl_3$ and results were recorded at 400 MHz on a Varian 400 instrument or at 500 MHz on a Varian 500 instrument. Mass spectrometry analysis was performed using a Waters LCT time-of-flight mass spectrometry instrument utilizing electrospray ionization operating in positive-ion (ESI+) or negative-ion (ESI−) modes where indicated.

A Representative Procedure for Synthesis of Acyl Pyruvates.

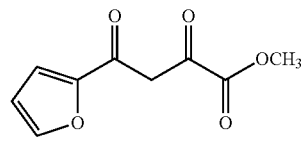 [SMILES: COC(=O)C(=O)CC(=O)c1ccco1]

Methyl 4-(furan-2-yl)-2,4-dioxobutanoate (20)

(see, e.g., Ghosh, A. K., et al., J Med Chem 2005, 48, 6767-71). To a stirred solution of MeOH (150 mL) at room temperature under nitrogen, freshly cut Na (1.81 g, 78.7 mmol) was added in pieces and with care. After all the sodium dissolved, a mixture of 2-acetylfuran (6 mL, 59.8 mmol) and diethyl oxalate (8.14 mL, 59.9 mmol) was added dropwise over a period of 3 min at room temperature. The resulting mixture was continued to stir. Brown precipitates formed after 20 min stir. The mixture was stirred for a total of 1 h. The reaction mixture was cooled to 0° C., and a mixture of concentrated $H_2SO_4$ and ice was added. Some solid precipitated at this point which was filtered off but was not the desired product by 1H NMR. The filterate was extracted with $CH_2Cl_2$ (50 mL×2). The combined organic layers were washed with brine, dried ($Na_2SO_4$), filtered, and concentrated under reduced pressure. The crude was recrystallized from hot iPrOH to give the title compound (4.15 g, 35%) as a dark brown solid. $^1$H NMR (400 MHz, $CDCl_3$) δ 7.67-7.65 (m, 1H), 7.33 (d, J=3.6 Hz, 1H), 6.93 (s, 1H), 6.60 (dd, J=3.5, 1.5 Hz, 1H), 3.91 (s, 3H). $^{13}$C NMR (100 MHz, $CDCl_3$) δ 181.01, 165.39, 162.43, 150.82, 147.73, 118.58, 113.14, 99.17, 53.18.

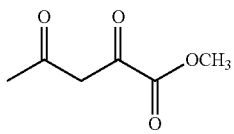

Methyl 2,4-dioxopentanoate (21)

Synthesized using the procedure for 20 except acetone was used as one of the starting material. Crude was subjected to flash column chromatography on silica gel to provide the title compound (1.36 g, 26%) as a white gel. $^1$H NMR (500 MHz, $CDCl_3$) δ 6.38 (s, 1H), 3.90 (s, 3H), 2.26 (s, 3H). $^{13}$C NMR (125 MHz, $CDCl_3$) δ 199.96, 166.58, 162.48, 102.20, 53.10, 27.61.

A Representative Procedure for Synthesis of Aminopyrazoles from Substituted Hydrazines.

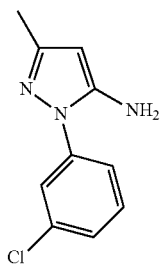

1-(3-Chlorophenyl)-3-methyl-1H-pyrazol-5-amine (22)

(see, e.g., Ganesan, A., et al., Journal of Organic Chemistry 1993, 58, 6155-6157). A solution of 3-aminocrotonitrile (mixture of cis and trans) (1.50 g, 17.5 mmol) and 3-chlorophenylhydrazine hydrochloride (3.0 g, 16.2 mmol) in 25 mL of 1N HCl was heated to reflux for 3 h under nitrogen. The reaction mixture was diluted with $H_2O$ (30 mL) and extracted with EtOAc (20 mL×2). The combined organic layers were washed with brine, dried ($Na_2SO_4$), filtered, and concentrated under reduced pressure. The crude was recrystallized from hot iPrOH to give the title compound (677 mg, 20%) as a beige fluffy solid. $^1$H NMR (500 MHz, $CDCl_3$) δ 7.62 (s, 1H), 7.48 (d, J=8.0 Hz, 1H), 7.37 (t, J=8.0 Hz, 1H), 7.28 (d, J=9.5 Hz, 1H), 5.46 (s, 1H), 2.22 (s, 3H). $^{13}$C NMR (125 MHz, $CDCl_3$) δ 149.95, 145.30, 139.87, 135.05, 130.32, 126.86, 123.67, 121.28, 91.41, 13.89.

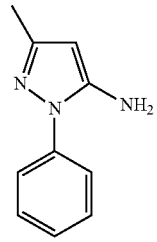

3-Methyl-1-phenyl-1H-pyrazol-5-amine (23)

Synthesized using the procedure for 22 except phenyl hydrazine was used as the hydrazine. Recrystallization of crude from hot EtOH provided the title compound (1.28 g, 37%) as pink crystals. $^1$H NMR (400 MHz, $CDCl_3$) δ 7.54 (s, 1H), 7.51 (s, 1H), 7.44 (t, J=7.5 Hz, 2H), 7.30 (t, J=7.4 Hz, 1H), 5.43 (s, 1H), 3.77 (s, 2H), 2.22 (s, 3H). $^{13}$C NMR (100 MHz, $CDCl_3$) δ 149.37, 145.21, 138.65, 129.38, 126.99, 123.77, 90.68, 13.93.

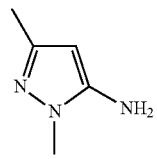

1,3-Dimethyl-1H-pyrazol-5-amine (24)

Synthesized using the procedure for 22 except methyl hydrazine was used as the hydrazine. Recrystallization of crude from hot $CH_2Cl_2$ provided the title compound (908 mg, 45%) as clear crystals. $^1$H NMR (400 MHz, $CDCl_3$) δ 5.30 (s, 1H), 3.55 (s, 3H), 2.11 (s, 3H). $^{13}$C NMR (100 MHz, $CDCl_3$) δ 147.16, 144.96, 90.79, 33.83, 13.78.

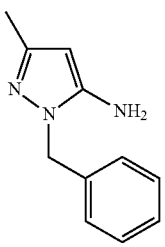

1-Benzyl-3-methyl-1H-pyrazol-5-amine (25)

Synthesized using the procedure for 22 except benzyl hydrazine dihydrochloride was used as the hydrazine. After the reaction mixture was stopped and cooled to room temperature, solid precipitated which was filtered off and dried in vacuum oven to provide the title compound (3.6 g, 98%) as a white solid. $^1$H NMR (400 MHz, DMSO-$d_6$) δ 7.40-7.34 (m, 2H), 7.34-7.27 (m, 3H), 5.57 (s, 1H), 5.35 (s, 2H), 2.18 (s, 3H). $^{13}$C NMR (100 MHz, CDCl$_3$) δ 151.48, 146.65, 135.16, 129.19, 128.61, 128.00, 91.19, 49.13, 11.44.

A Representative Procedure for Synthesis of Aminopyrazoles from Arylaldehydes.

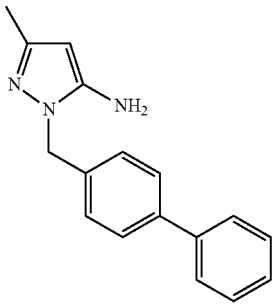 [SMILES: Cc1cc(N)n(Cc2ccc(-c3ccccc3)cc2)n1]

1-([1,1'-Biphenyl]-4-ylmethyl)-3-methyl-1H-pyrazol-5-amine (26)

(see, e.g., WO2009150614A1). To a solution of hydrazine monohydrate (hydrazine 78-82%) (0.51 ml, 10.5 mmol) in THF (2 mL), crotononitrile (mixture of cis and trans) (0.82 ml, 10.1 mmol) was added dropwise. The mixture was stirred at 40° C. for 2 h. The mixture was allowed to cool to room temperature and biphenyl-4-carboxaldehyde (1.82 g, 10.0 mmol) was added. The mixture was stirred at 40° C. for 2 h. The mixture was concentrated under reduced pressure. To the resulting yellow solid was added iPrOH (15 mL) and the suspension was transferred to a pressure vessel. t-BuONa (993 mg, 10.3 mmol) was added and the mixture was stirred at 100° C. for 2 h 30 min. The mixture was allowed to cool to room temperature and diluted with water (50 mL). The mixture was extracted with Et$_2$O (50 mL×2). The combined organic layers were extracted with 1N aq. HCl (2×30 mL). The combined aqueous phases were basified to pH 14 with 50% aq. NaOH and extracted with Et$_2$O (50 mL×2). The combined organic layers were washed with brine, dried (Na$_2$SO$_4$), filtered, and concentrated under reduced pressure to provide the title compound (885 mg, 34% over three steps) as a yellow solid. Crude was used in the next reaction without further purification. $^1$H NMR (500 MHz, DMSO-d$_6$) δ 7.68-7.61 (m, 4H), 7.45 (t, J=7.5 Hz, 2H), 7.39 (d, J=7.9 Hz, 2H), 7.37-7.33 (m, 1H), 5.59 (s, 1H), 5.38 (s, 2H), 2.20 (s, 3H). $^{13}$C NMR (125 MHz, DMSO-d$_6$) δ 151.46, 146.77, 140.52, 139.98, 134.32, 129.40, 128.62, 128.09, 127.51, 127.14, 91.23, 48.92, 11.54.

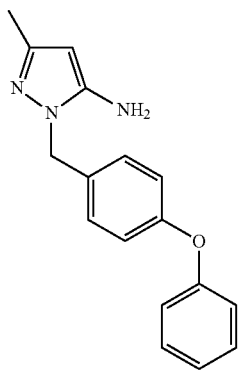 [SMILES: Cc1cc(N)n(Cc2ccc(Oc3ccccc3)cc2)n1]

3-Methyl-1-(4-phenoxybenzyl)-1H-pyrazol-5-amine (27)

Synthesized using the procedure for 26 except 4-phenoxybenzaldehyde was used as the aldehyde. Title compound (994 mg, 35% over three steps) was obtained as a yellow solid. $^1$H NMR (500 MHz, DMSO-d$_6$) δ 7.38 (dd, J=17.2, 8.5 Hz, 4H), 7.17-7.13 (m, 1H), 7.03-6.98 (m, 4H), 5.58 (s, 1H), 5.32 (s, 2H), 2.19 (s, 3H). $^{13}$C NMR (125 MHz, DMSO-d$_6$) δ 157.12, 156.73, 151.33, 146.70, 130.56, 130.06, 130.04, 124.17, 119.24, 119.12, 91.24, 48.61, 11.51.

A Modified Procedure for Synthesis of Aminopyrazoles from Arylaldehydes.

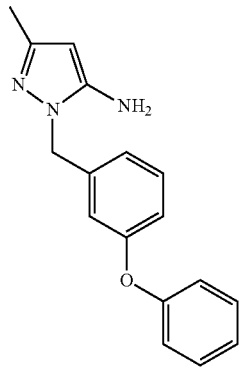 [SMILES: Cc1cc(N)n(Cc2cccc(Oc3ccccc3)c2)n1]

3-Methyl-1-(3-phenoxybenzyl)-1H-pyrazol-5-amine (28)

(see, e.g., Misra, R. N., et al., Bioorg Med Chem Lett 2003, 13, 1133-6). To a solution of hydrazine monohydrate (hydrazine 78-82%) (0.80 ml, 16.5 mmol) in THF (3 mL), crotononitrile (mixture of cis and trans) (1.1 ml, 13.5 mmol) was added dropwise. The mixture was stirred at 40° C. for 2 h. The mixture was allowed to cool to room temperature and 3-phenoxybenzaldehyde (2.14 ml, 12 mmol) was added dropwise. The mixture was stirred at 40° C. for 2 h. The mixture was concentrated under reduced pressure. To the resulting intermediate was added nPrOH (10 mL) and the suspension was transferred to a pressure vessel. t-BuONa (1.41 g, 14.7 mmol) was added and the mixture was stirred at 110° C. for 2 h 30 min. The mixture was allowed to cool to room temperature and diluted with water (50 mL). The mixture was extracted with Et$_2$O (50 mL×2). The combined organic layers were extracted with 1N aq. HCl (2×30 mL). The combined aqueous phases were basified to pH 14 with 50% aq. NaOH and extracted with Et$_2$O (50 mL×2). The combined organic layers were washed with brine, dried (Na$_2$SO$_4$), filtered, and concentrated under reduced pressure to provide the title compound (670 mg, 20% over three steps) as an orange oil. Crude was used in the next reaction without further purification. $^1$H NMR (500 MHz, CDCl$_3$) δ 7.32 (t, J=7.0 Hz, 2H), 7.25 (t, J=7.8 Hz, 1H), 7.10 (t, J=6.9 Hz, 1H), 6.98 (d, J=7.8 Hz, 2H), 6.85 (t, J=7.6 Hz, 2H), 6.80 (s, 1H), 5.37 (d, J=2.6 Hz, 1H), 5.10 (s, 2H), 2.17 (s, 3H). $^{13}$C NMR (125 MHz, CDCl$_3$) δ 157.81, 156.75, 147.74, 145.05, 139.08, 130.19, 129.75, 123.46, 121.22, 119.04, 117.63, 116.99, 91.65, 50.86, 13.92.

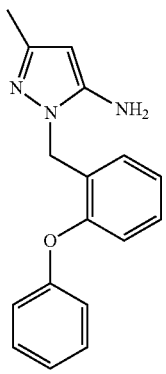 [SMILES: Cc1cc(N)n(Cc2ccccc2Oc2ccccc2)n1]

3-Methyl-1-(2-phenoxybenzyl)-1H-pyrazol-5-amine (29)

Synthesized using the procedure for 28 except 2-phenoxybenzaldehyde was used as the aldehyde. Title compound (485 mg, 34% over three steps) was obtained as an off-white solid. Crude was used in the next reaction without further purification. $^1$H NMR (500 MHz, CDCl$_3$) δ 7.34 (t, J=7.1 Hz, 2H), 7.24-7.17 (m, 2H), 7.12 (t, J=7.1 Hz, 1H), 7.08 (t, J=7.5 Hz, 1H), 6.96 (d, J=7.9 Hz, 2H), 6.84 (d, J=8.1 Hz, 1H), 5.32 (s, 1H), 5.15 (s, 2H), 3.63 (s, 2H), 2.17 (s, 3H). $^{13}$C NMR (126 MHz, CDCl$_3$) δ 156.75, 153.93, 147.82, 145.11, 129.94, 129.69, 129.09, 127.98, 124.16, 123.61, 118.48, 118.38, 90.68, 45.69, 14.00.

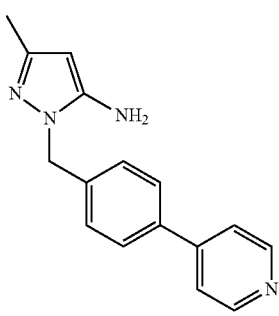 [SMILES: Cc1cc(N)n(Cc2ccc(-c3ccncc3)cc2)n1]

3-Methyl-1-(4-(pyridin-4-yl)benzyl)-1H-pyrazol-5-amine (30)

Synthesized using the procedure for 28 except 4-pyridine-4-benzaldehyde was used as the aldehyde. The title compound (274 mg, 20% over three steps) was obtained as a white solid. Crude was used in the next reaction without further purification. $^1$H NMR (500 MHz, CDCl$_3$) δ 8.63 (d, J=4.5 Hz, 2H), 7.58 (d, J=8.1 Hz, 2H), 7.45 (d, J=4.5 Hz, 2H), 7.26 (d, J=7.3 Hz, 2H), 5.42 (s, 1H), 5.19 (s, 2H), 3.38 (s, 2H), 2.20 (s, 3H). $^{13}$C NMR (125 MHz, CDCl$_3$) δ 150.26, 147.88, 147.72, 144.98, 138.06, 137.49, 127.48, 121.48, 91.83, 50.82, 13.97.

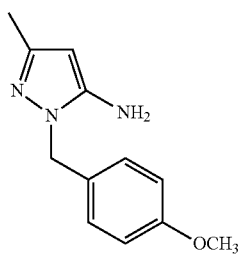 [SMILES: COc1ccc(Cn2nc(C)cc2N)cc1]

1-(4-Methoxybenzyl)-3-methyl-1H-pyrazol-5-amine (31)

Synthesized using the procedure for 26 except p-anisaldehyde was used as the aldehyde. Title compound (910 mg, 42% over three steps) was obtained as a yellow oil which solidified upon standing. Crude was used in the next reaction without further purification. $^1$H NMR (500 MHz, DMSO-d$_6$) δ 7.09 (d, J=8.3 Hz, 2H), 6.84 (d, J=8.3 Hz, 2H), 5.10 (s, 2H), 5.07 (s, 1H), 4.90 (s, 2H), 3.70 (s, 3H), 1.94 (s, 3H). $^{13}$C NMR (125 MHz, DMSO-d$_6$) δ 158.73, 147.58, 146.13, 130.82, 129.05, 114.05, 88.29, 55.49, 49.31, 14.30.

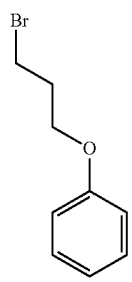

(3-Bromopropoxy)benzene (32)

(see, e.g., Martins, A., et al., J Org Chem 2006, 71, 4937-42). 1-Phenol (1.03 g, 10.9 mmol), 1,3-dibromopropane (16 mL, 158 mmol), and K$_2$CO$_3$ (7.43 g, 53.8 mmol) were combined and suspended in acetone (100 mL). The mixture was stirred under reflux for 19 h, then filtered to remove the base and concentrated under reduced pressure. The crude was placed on high vacuum and provide the title compound (1.81 g, 77%) as a clear oil. Crude was used in the next reaction without further purification. $^1$H NMR (400 MHz, CDCl$_3$) δ 7.29 (t, J=7.6 Hz, 2H), 6.96 (t, J=7.8 Hz, 1H), 6.91 (d, J=7.8 Hz, 2H), 4.10 (t, J=5.8 Hz, 2H), 3.61 (t, J=6.1 Hz, 2H), 2.37-2.28 (m, 2H). $^{13}$C NMR (100 MHz, CDCl$_3$) δ 158.62, 129.48, 120.89, 114.47, 65.12, 32.39, 30.12.

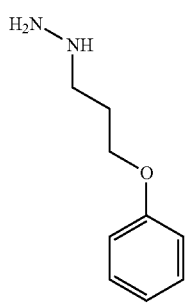 [SMILES: NNCCCOc1ccccc1]

(3-Phenoxypropyl)hydrazine hydrochloride (33)

(see, e.g., WO2003027074A1). 32 (1.80 g, 8.4 mmol) was dissolved in EtOH (9 mL) followed by addition of hydrazine monohydrate (hydrazine 78-82%) (4.5 ml, 93 mmol). The solution was heated at 80° C. for 3 h 30 min. After cooling to room temperature, the reaction mixture was concentrated under reduced pressure and the crude was treated with 2N HCl (7 mL) and dichloromethane (4 mL) while stirring at room temperature overnight. The crude was placed on high vacuum to remove solvent and then used without further purification in the next reaction.

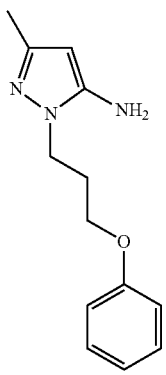 [SMILES: Cc1cc(N)n(CCCOc2ccccc2)n1]

3-Methyl-1-(3-phenoxypropyl)-1H-pyrazol-5-amine (34)

Synthesized using the procedure for 22 except 33 was used as crude and as the hydrazine. After the reaction mixture was stopped and cooled down to room temperature, the reaction mixture was diluted with $H_2O$ and extracted with EtOAC (2×). Combined organic layers were washed with brine, dried ($Na_2SO_4$), filtered, and concentrated under reduced pressure. Crude was subjected to flash column chromatography on silica gel to provide the title compound (663 mg, 48% over two steps) as a yellow oil. $^1$H NMR (400 MHz, CDCl$_3$) δ 7.23 (t, J=7.2 Hz, 2H), 6.92 (t, J=7.0 Hz, 1H), 6.84 (d, J=8.0 Hz, 2H), 5.21 (s, 1H), 4.03 (t, J=6.2 Hz, 2H), 3.84 (t, J=5.6 Hz, 2H), 3.65 (s, 2H), 2.22-2.14 (m, 2H), 2.11 (s, 3H). $^{13}$C NMR (100 MHz, CDCl$_3$) δ 158.19, 147.73, 145.69, 129.59, 121.12, 114.43, 90.07, 63.94, 42.66, 29.16, 13.92.

A Representative Procedure for Synthesis of Esters.

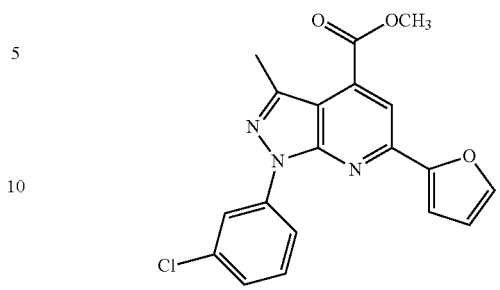

Methyl 1-(3-chlorophenyl)-6-(furan-2-yl)-3-methyl-1H-pyrazolo[3,4-b]pyridine-4-carboxylate (35)

(see, e.g., Volochnyuk, D. M., et al., J Comb Chem 2010, 12, 510-7). A solution of 22 (306 mg, 1.47 mmol) and 20 (295 mg, 1.50 mmol) in glacial AcOH (10 mL) was heated to reflux for 3 h. When the reaction mixture was cooled down to room temperature, yellow precipitates formed which were filtered and washed with $H_2O$. Filtercake was placed in a vacuum oven to give the title compound (470 mg, 87%) as a yellow solid. $^1$H NMR (500 MHz, CDCl$_3$) δ 8.48 (s, 1H), 8.29 (d, J=9.1 Hz, 1H), 8.06 (s, 1H), 7.62 (s, 1H), 7.43 (t, J=8.1 Hz, 1H), 7.28-7.23 (m, 2H), 6.63-6.59 (m, 1H), 4.06 (s, 3H), 2.75 (s, 3H). $^{13}$C NMR (125 MHz, CDCl$_3$) δ 165.53, 152.95, 151.82, 148.42, 144.43, 143.32, 140.31, 134.59, 133.91, 129.93, 125.41, 120.77, 118.52, 113.87, 112.57, 112.24, 110.94, 52.73, 16.21.

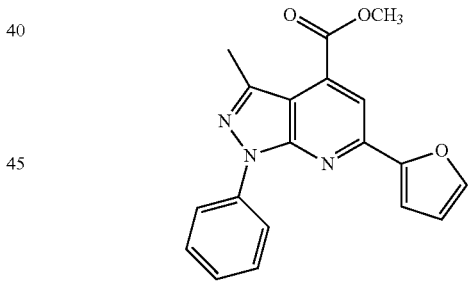

Methyl 6-(furan-2-yl)-3-methyl-1-phenyl-1H-pyrazolo[3,4-b]pyridine-4-carboxylate (36)

Synthesized using the procedure for 35 except 23 was used as the amine. After reaction mixture was stopped and cooled down to room temperature, yellow precipitates formed which were filtered, washed with $H_2O$ and dried in vacuum oven to give the title compound (971 mg, 97%) as a yellow solid. $^1$H NMR (400 MHz, CDCl$_3$) δ 8.29 (d, J=8.6 Hz, 2H), 8.05 (s, 1H), 7.59 (s, 1H), 7.52 (t, J=7.7 Hz, 2H), 7.29 (t, J=7.2 Hz, 1H), 7.23 (s, 1H), 6.58 (s, 1H), 4.04 (s, 3H), 2.76 (s, 3H). $^{13}$C NMR (100 MHz, CDCl$_3$) δ 165.73, 153.12, 151.69, 148.28, 144.27, 142.68, 139.24, 133.75, 128.94, 125.73, 121.17, 113.67, 112.45, 111.91, 110.70, 52.68, 16.19.

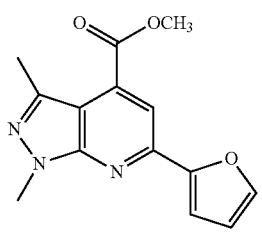 [SMILES: COC(=O)c1cc(-c2ccco2)nc2c1c(C)nn2C]

Methyl 6-(furan-2-yl)-1,3-dimethyl-1H-pyrazolo[3,4-b]pyridine-4-carboxylate (37)

Synthesized using the procedure for 35 except 24 was used as the pyrazole amine. Crude was subjected to flash column chromatography on silica gel to provide the title compound (616 mg, 76%) as a light pink solid. $^1$H NMR (400 MHz, CDCl$_3$) δ 7.93 (s, 1H), 7.59-7.56 (m, 1H), 7.17 (d, J=3.4 Hz, 1H), 6.55 (dd, J=3.4, 1.7 Hz, 1H), 4.07 (s, 3H), 3.99 (s, 3H), 2.65 (s, 3H). $^{13}$C NMR (100 MHz, CDCl$_3$) δ 165.82, 153.11, 152.14, 147.83, 144.15, 140.61, 133.27, 113.10, 112.33, 110.30, 109.86, 52.52, 33.62, 16.00.

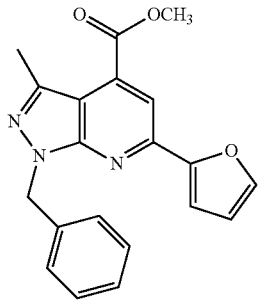 [SMILES: COC(=O)c1cc(-c2ccco2)nc2c1c(C)nn2Cc1ccccc1]

Methyl 1-benzyl-6-(furan-2-yl)-3-methyl-1H-pyrazolo[3,4-b]pyridine-4-carboxylate (38)

Synthesized using the procedure for 35 except 25 was used as the pyrazole amine. Crude was subjected to flash column chromatography on silica gel to provide the title compound (97 mg, 9%) as a light yellow solid. $^1$H NMR (400 MHz, CDCl$_3$) δ 8.06 (s, 1H), 7.67 (s, 1H), 7.33 (d, J=7.2 Hz, 2H), 7.28 (t, J=7.2 Hz, 2H), 7.26-7.21 (m, 1H), 7.08-7.04 (m, 1H), 6.61 (dd, J=3.5, 1.8 Hz, 1H), 5.73 (s, 2H), 4.04 (s, 3H), 2.72 (s, 3H). $^{13}$C NMR (100 MHz, CDCl$_3$) δ 165.99, 152.08, 150.69, 146.13, 144.45, 141.45, 137.02, 133.86, 128.53, 127.97, 127.62, 114.14, 112.40, 112.23, 111.85, 53.00, 50.45, 16.69.

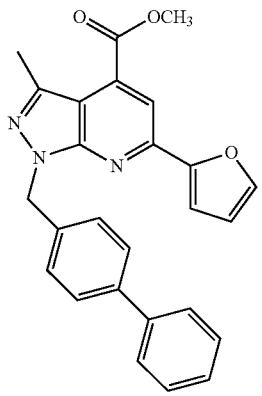 [SMILES: COC(=O)c1cc(-c2ccco2)nc2c1c(C)nn2Cc1ccc(-c2ccccc2)cc1]

Methyl 1-([1,1'-biphenyl]-4-ylmethyl)-6-(furan-2-yl)-3-methyl-1H-pyrazolo[3,4-b]pyridine-4-carboxylate (39)

Synthesized using the procedure for 35 except 26 was used as the pyrazole amine. Crude was subjected to flash column chromatography on silica gel to provide the title compound (87 mg, 7%) as an off-white solid. $^1$H NMR (500 MHz, CDCl$_3$) δ 8.10 (s, 1H), 7.70 (s, 1H), 7.54 (t, J=7.5 Hz, 4H), 7.42 (dd, J=14.2, 7.9 Hz, 4H), 7.32 (t, J=7.4 Hz, 1H), 7.08 (d, J=3.4 Hz, 1H), 6.64 (dd, J=3.4, 1.7 Hz, 1H), 5.79 (s, 2H), 4.07 (s, 3H), 2.76 (s, 3H). $^{13}$C NMR (125 MHz, CDCl$_3$) δ 166.00, 152.12, 150.72, 146.21, 144.47, 141.55, 140.79, 140.60, 136.05, 133.93, 128.71, 128.46, 127.33, 127.24, 127.06, 114.20, 112.42, 112.26, 111.92, 53.01, 50.20, 16.71.

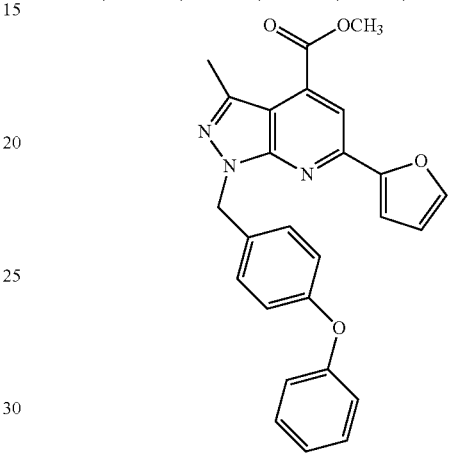

Methyl 6-(furan-2-yl)-3-methyl-1-(4-phenoxybenzyl)-1H-pyrazolo[3,4-b]pyridine-4-carboxylate (40)

Synthesized using the procedure for 35 except 27 was used as the pyrazole amine. Crude was subjected to flash column chromatography on silica gel to provide the title compound (478 mg, 43%) as a yellow oil. $^1$H NMR (500 MHz, CDCl$_3$) δ 8.03 (s, 1H), 7.61 (s, 1H), 7.37 (d, J=8.3 Hz, 2H), 7.30 (t, J=7.7 Hz, 2H), 7.25 (d, J=3.4 Hz, 1H), 7.08 (t, J=7.4 Hz, 1H), 6.97 (d, J=8.4 Hz, 2H), 6.93 (d, J=8.3 Hz, 2H), 6.61-6.58 (m, 1H), 5.66 (s, 2H), 4.04 (s, 3H), 2.70 (s, 3H). $^{13}$C NMR (125 MHz, CDCl$_3$) δ 165.91, 157.01, 156.82, 153.27, 152.10, 148.09, 144.18, 141.35, 133.53, 132.00, 129.70, 129.59, 123.29, 118.95, 118.79, 113.33, 112.41, 110.37, 110.19, 52.59, 49.88, 16.12.

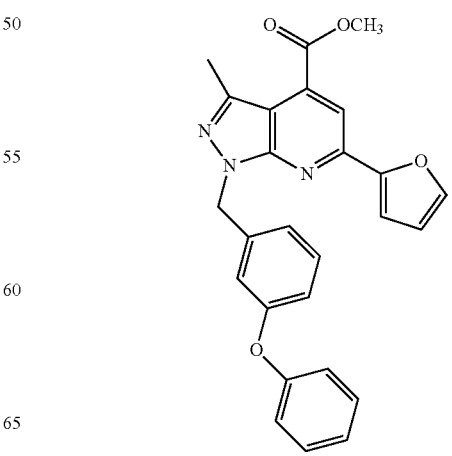

Methyl 6-(furan-2-yl)-3-methyl-1-(3-phenoxybenzyl)-1H-pyrazolo[3,4-b]pyridine-4-carboxylate (41)

Synthesized using the procedure for 35 except 28 was used as the pyrazole amine. Crude was subjected to flash column chromatography on silica gel to provide the title compound (563 mg, 82%) as a yellow viscous oil. $^1$H NMR (400 MHz, CDCl$_3$) δ 8.01 (s, 1H), 7.58 (s, 1H), 7.30-7.20 (m, 3H), 7.18-7.14 (m, 1H), 7.09-7.02 (m, 2H), 7.00 (s, 1H), 6.97-6.92 (m, 2H), 6.89-6.83 (m, 1H), 6.57 (s, 1H), 5.65 (s, 2H), 4.03 (s, 3H), 2.69 (s, 3H). $^{13}$C NMR (100 MHz, CDCl$_3$) δ 165.89, 157.48, 156.78, 153.17, 152.21, 148.11, 147.73, 144.13, 141.47, 139.13, 133.52, 129.84, 129.66, 123.32, 122.47, 119.03, 118.18, 117.69, 113.36, 112.40, 110.42, 52.59, 50.11, 16.11. ESI MS: m/z 440.1 (M+H)$^+$.

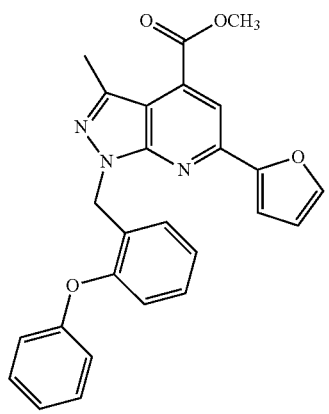 [SMILES: COC(=O)c1cc(-c2ccco2)nc2c1c(C)nn2Cc1ccccc1Oc1ccccc1]

Methyl 6-(furan-2-yl)-3-methyl-1-(2-phenoxybenzyl)-1H-pyrazolo[3,4-b]pyridine-4-carboxylate (42)

Synthesized using the procedure for 35 except 29 was used as the pyrazole amine. Crude was subjected to flash column chromatography on silica gel to provide the title compound (551 mg, 81%) as a yellow oil which formed a foam upon standing. $^1$H NMR (500 MHz, CDCl$_3$) δ 7.98 (s, 1H), 7.57 (s, 1H), 7.27-7.18 (m, 3H), 7.13-7.10 (m, 1H), 7.09-7.05 (m, 1H), 7.05-6.99 (m, 2H), 6.90 (t, J=7.1 Hz, 3H), 6.56-6.53 (m, 1H), 5.80 (s, 2H), 4.03 (s, 3H), 2.66 (s, 3H). $^{13}$C NMR (125 MHz, CDCl$_3$) δ 165.95, 157.40, 154.05, 153.25, 152.40, 147.97, 144.01, 141.35, 133.34, 129.48, 129.39, 128.98, 128.84, 123.88, 122.70, 119.32, 117.90, 113.19, 112.32, 110.35, 109.99, 52.53, 45.19, 16.09.

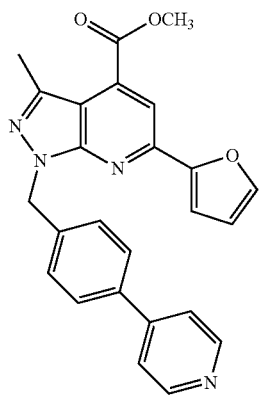 [SMILES: COC(=O)c1cc(-c2ccco2)nc2c1c(C)nn2Cc1ccc(-c2ccncc2)cc1]

Methyl 6-(furan-2-yl)-3-methyl-1-(4-(pyridin-4-yl)benzyl)-1H-pyrazolo[3,4-b]pyridine-4-carboxylate (43)

Synthesized using the procedure for 35 except 30 was used as the pyrazole amine. Crude was subjected to flash column chromatography on silica gel to provide the title compound (261 mg, 62%) as an off-white solid. $^1$H NMR (500 MHz, CDCl$_3$) δ 8.64-8.58 (m, 2H), 8.03 (s, 1H), 7.60 (s, 1H), 7.55 (d, J=7.8 Hz, 2H), 7.46 (d, J=7.8 Hz, 2H), 7.45-7.40 (m, 2H), 7.27-7.22 (m, 1H), 6.58 (s, 1H), 5.73 (s, 2H), 4.03 (s, 3H), 2.69 (s, 3H). $^{13}$C NMR (125 MHz, CDCl$_3$) δ 165.84, 153.21, 152.25, 150.19, 148.18, 147.87, 144.21, 141.62, 138.19, 137.46, 133.62, 128.70, 127.21, 121.49, 113.42, 112.40, 110.42, 110.21, 52.59, 50.00, 16.10.

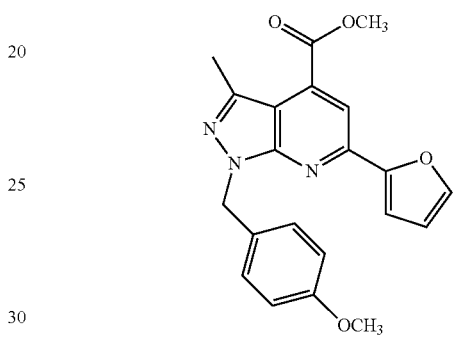

Methyl 6-(furan-2-yl)-1-(4-methoxybenzyl)-3-methyl-1H-pyrazolo[3,4-b]pyridine-4-carboxylate (44)

Synthesized using the procedure for 35 except 31 was used as the pyrazole amine. Crude was subjected to flash column chromatography on silica gel to provide the title compound (458 mg, 40%) as a light yellow solid. $^1$H NMR (400 MHz, CDCl$_3$) δ 8.00 (s, 1H), 7.59 (s, 1H), 7.33 (d, J=7.1 Hz, 2H), 7.27-7.20 (m, 1H), 6.81 (d, J=7.1 Hz, 2H), 6.62-6.55 (m, 1H), 5.61 (s, 2H), 4.01 (s, 3H), 3.74 (s, 3H), 2.67 (s, 3H). $^{13}$C NMR (100 MHz, CDCl$_3$) δ 165.94, 159.07, 153.31, 152.01, 147.98, 144.10, 141.16, 133.43, 129.45, 129.37, 113.89, 113.22, 112.38, 110.26, 110.17, 55.21, 52.56, 49.93, 16.11.

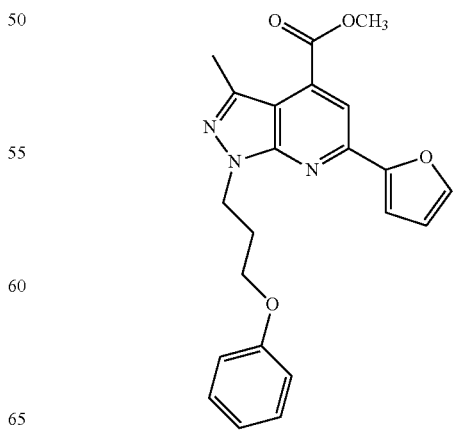

Methyl 6-(furan-2-yl)-3-methyl-1-(3-phenoxypropyl)-1H-pyrazolo[3,4-b]pyridine-4-carboxylate (45)

Synthesized using the procedure for 35 except 32 was used as the pyrazole amine. Crude was subjected to flash column chromatography on silica gel to provide the title compound (388 mg, 35%) as an off-white solid. $^1$H NMR (500 MHz, CDCl$_3$) δ 7.99 (s, 1H), 7.58 (s, 1H), 7.27-7.21 (m, 2H), 7.10 (s, 1H), 6.91 (t, J=6.9 Hz, 1H), 6.87 (d, J=8.7 Hz, 2H), 6.55 (dd, J=3.3, 1.7 Hz, 1H), 4.72 (t, J=6.8 Hz, 2H), 4.04 (s, 3H), 4.03-4.01 (m, 2H), 2.70 (s, 3H), 2.45 (p, J=6.4 Hz, 2H). $^{13}$C NMR (125 MHz, CDCl$_3$) δ 165.96, 158.82, 153.18, 152.21, 147.93, 144.06, 140.90, 133.39, 129.34, 120.62, 114.52, 113.21, 112.36, 110.29, 110.02, 65.08, 52.57, 43.83, 29.58, 16.06.

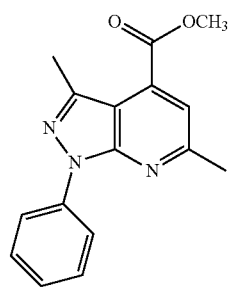 [SMILES: COC(=O)c1cc(C)nc2c1c(C)nn2-c1ccccc1]

Methyl 3,6-dimethyl-1-phenyl-1H-pyrazolo[3,4-b]pyridine-4-carboxylate (46)

Synthesized using the procedure for 35 except 21 and 23 were used as the starting materials. Crude was subjected to flash column chromatography on silica gel to provide the title compound (309 mg, 36%) as a light yellow solid. $^1$H NMR (400 MHz, CDCl$_3$) δ 8.23 (d, J=7.6 Hz, 2H), 7.53-7.46 (m, 3H), 7.31-7.24 (m, 1H), 4.01 (s, 3H), 2.74 (s, 3H), 2.72 (s, 3H). $^{13}$C NMR (100 MHz, CDCl$_3$) δ 166.04, 158.80, 151.85, 142.31, 139.23, 132.97, 128.94, 125.77, 121.38, 118.13, 111.10, 52.56, 24.91, 16.15.

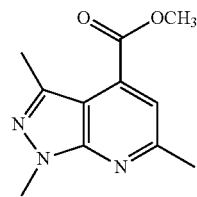 [SMILES: COC(=O)c1cc(C)nc2c1c(C)nn2C]

Methyl 1,3,6-trimethyl-1H-pyrazolo[3,4-b]pyridine-4-carboxylate (47)

Synthesized using the procedure for 35 except 21 and 24 were used as the starting materials. Crude was subjected to flash column chromatography on silica gel to provide the title compound (266 mg, 40%) as a white solid. $^1$H NMR (400 MHz, CDCl$_3$) δ 7.41 (s, 1H), 4.06 (s, 3H), 3.99 (s, 3H), 2.68 (s, 3H), 2.65 (s, 3H). $^{13}$C NMR (100 MHz, CDCl$_3$) δ 166.20, 158.21, 152.29, 140.27, 132.69, 117.38, 109.19, 52.44, 33.61, 24.70, 15.96.

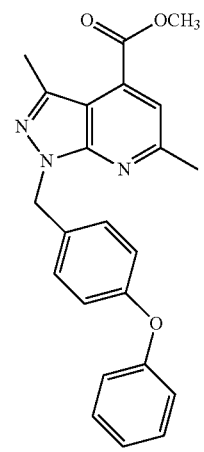

Methyl 3,6-dimethyl-1-(4-phenoxybenzyl)-1H-pyrazolo[3,4-b]pyridine-4-carboxylate (48)

Synthesized using the procedure for 35 except 20 and 27 were used as starting materials. Crude was subjected to flash column chromatography on silica gel to provide the title compound (67 mg, 12%) as a yellow oil. $^1$H NMR (500 MHz, CDCl$_3$) δ 7.45 (s, 1H), 7.33-7.28 (m, 4H), 7.08 (t, J=7.4 Hz, 1H), 6.98 (d, J=7.7 Hz, 2H), 6.92 (d, J=7.3 Hz, 2H), 5.63 (s, 2H), 4.01 (s, 3H), 2.71 (s, 3H), 2.68 (s, 3H). $^{13}$C NMR (125 MHz, CDCl$_3$) δ 166.21, 158.43, 157.06, 156.71, 152.26, 140.98, 132.78, 132.14, 129.68, 129.35, 123.25, 118.91, 118.79, 117.65, 109.33, 52.45, 49.62, 24.77, 16.08.

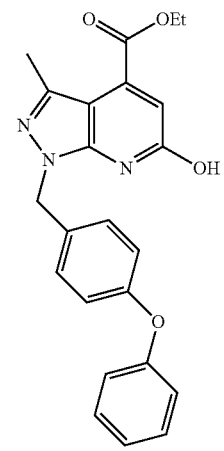 [SMILES: CCOC(=O)c1cc(O)nc2c1c(C)nn2Cc1ccc(Oc2ccccc2)cc1]

Ethyl 6-hydroxy-3-methyl-1-(4-phenoxybenzyl)-1H-pyrazolo[3,4-b]pyridine-4-carboxylate (49)

(see, e.g., Neres, J., et al., J Med Chem 2013, 56, 2385-405). A solution of diethyl oxaloacetate sodium salt (516 mg, 2.46 mmol) and 28 (646 mg, 2.31 mmol) in a mixture of toluene:H$_2$O: glacial AcOH (5 mL/5 mL/0.5 mL) was heated at 80° C. overnight. The mixture was diluted with H$_2$O (20 mL) and extracted with EtOAc (20 mL×2). Combined organic layers were washed with brine, dried (Na$_2$SO$_4$), filtered and concentrated under reduced pressure to provide the desired crude. Crude was used in the next reaction without further purification.

A suspension of diethyl 2-(5-amino-3-methyl-1-(4-phenoxybenzyl)-1H-pyrazol-4-yl)-2-hydroxysuccinate (crude from above) (2.31 mmol) from x in glacial AcOH (14 mL) was refluxed for 2 h. The mixture was concentrated under reduced pressure as much as possible. Then MeOH was added and the product crystallized as a white solid which was filtered, washed with cold MeOH and dried in a vacuum oven to provide the title compound (628 mg, 67% over two steps) as a tan solid. $^1$H NMR (500 MHz, CDCl$_3$) δ 7.40 (d, J=8.3 Hz, 2H), 7.31 (t, J=7.3 Hz, 2H), 7.09 (t, J=7.4 Hz, 1H), 6.97 (d, J=8.0 Hz, 2H), 6.92 (d, J=8.4 Hz, 2H), 6.78 (s, 1H), 5.50 (s, 2H), 4.44 (q, J=7.1 Hz, 2H), 2.53 (s, 3H), 1.43 (t, J=7.1 Hz, 3H). $^{13}$C NMR (125 MHz, CDCl$_3$) δ 164.83, 164.75, 157.17, 156.81, 143.45, 143.12, 139.06, 130.59, 129.72, 129.51, 123.43, 119.11, 118.70, 113.27, 103.16, 62.13, 50.60, 15.44, 14.16. ESI MS: m/z 404.1 (M+H)$^+$.

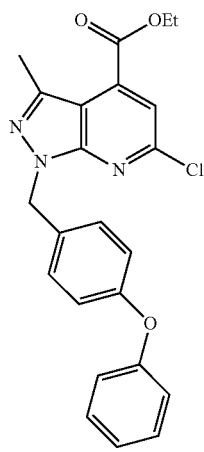 [SMILES: CCOC(=O)c1cc(Cl)nc2c1c(C)nn2Cc1ccc(Oc2ccccc2)cc1]

Ethyl 6-chloro-3-methyl-1-(4-phenoxybenzyl)-1H-pyrazolo[3,4-b]pyridine-4-carboxylate (50)

(see, e.g., Sercel, A. D., et al., Synthetic Communications 2007, 37, 4199-4208). Fresh Vilsmeier's reagent was prepared as follows: to a stirring solution of 1.2 DCE (4 mL) was added DMF (0.2 mL, 2.6 mmol). The resulting solution was cooled down to 0° C. and (COCl)$_2$ (0.22 mL, 2.6 mmol) was added dropwise. The viscous suspension was stirred at room temperature for 10 min, and then 49 (104 mg, 0.26 mmol) was added to the mixture. The suspension was heated to reflux overnight. The mixture was diluted with H$_2$O (10 mL) and extracted with EtOAc (15 mL×2). The organic layers were washed with brine, dried (Na$_2$SO$_4$) and concentrated under reduced pressure to provide the title compound (120 mg, quantitative yield) as a yellow oil. Crude was used in the next reaction without further purification. $^1$H NMR (500 MHz, CDCl$_3$) δ 7.56 (s, 1H), 7.31 (t, J=8.2 Hz, 4H), 7.08 (t, J=7.4 Hz, 1H), 6.97 (d, J=7.7 Hz, 2H), 6.93 (d, J=8.5 Hz, 2H), 5.59 (s, 2H), 4.48 (q, J=7.1 Hz, 2H), 2.69 (s, 3H), 1.46 (t, J=7.1 Hz, 3H). $^{13}$C NMR (125 MHz, CDCl$_3$) δ 164.34, 157.00, 156.91, 151.20, 150.30, 141.77, 135.67, 131.25, 129.71, 129.54, 123.37, 119.00, 118.78, 117.69, 110.41, 62.31, 50.03, 16.16, 14.20.

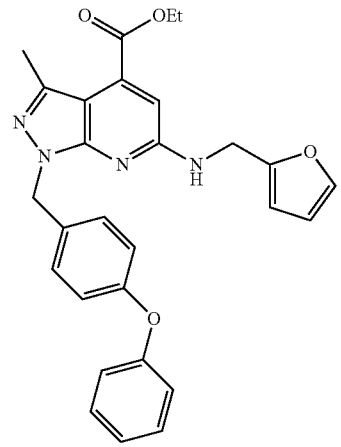

Ethyl 6-((furan-2-ylmethyl)amino)-3-methyl-1-(4-phenoxybenzyl)-1H-pyrazolo[3,4-b]pyridine-4-carboxylate (51)

(see, e.g., WO2013039988A1). A pressure vessel was charged with 50 (119 mg, 0.28 mmol), 2-aminomethylfuran (0.12 mL, 1.36 mmol) and iPrOH (4 mL). The vessel was sealed and the reaction mixture was heated at 100° C. overnight. An additional 1 mL (11.3 mmol) of amine was added and the mixture was heated at 150° C. overnight. The reaction mixture was diluted with H$_2$O (10 mL) and extracted with EtOAc (15 mL×2). Combined organic layers were washed with brine, dried (Na$_2$SO$_4$) and concentrated under reduced pressure. Crude was subjected to flash column chromatography on silica gel to provide the title compound (40 mg, 30%) as an orange oil. $^1$H NMR (400 MHz, CDCl$_3$) δ 7.36-7.24 (m, 5H), 7.07 (t, J=7.3 Hz, 1H), 6.97 (d, J=8.2 Hz, 2H), 6.91 (d, J=8.2 Hz, 2H), 6.80 (s, 1H), 6.30 (s, 1H), 6.22 (s, 1H), 5.47 (s, 2H), 5.14 (t, J=5.4 Hz, 1H), 4.68 (d, J=5.5 Hz, 2H), 4.43 (q, J=7.1 Hz, 2H), 2.58 (s, 3H), 1.42 (t, J=7.1 Hz, 3H). $^{13}$C NMR (100 MHz, CDCl$_3$) δ 165.83, 157.16, 156.86, 156.51, 152.16, 152.06, 141.97, 141.27, 134.71, 132.57, 129.67, 129.44, 123.17, 118.82, 110.40, 107.27, 106.91, 104.45, 61.66, 49.53, 38.75, 16.15, 14.23. ESI MS: m/z 483.1 (M+H)$^+$.

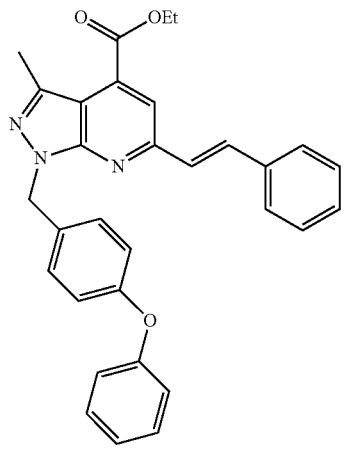 [SMILES: CCOC(=O)c1cc(/C=C/c2ccccc2)nc2c1c(C)nn2Cc1ccc(Oc2ccccc2)cc1]

(E)-Ethyl 3-methyl-1-(4-phenoxybenzyl)-6-styryl-1H-pyrazolo[3,4-b]pyridine-4-carboxylate (52)

(see, e.g., Greig, I. R., et al., J Med Chem 2006, 49, 7487-92; Li, X., et al., J Med Chem 2003, 46, 5663-73). To a mixture of 50 (205 mg, 0.49 mmol), Pd(PPh$_3$)$_4$ (27 mg, 0.02 mmol) and (E)-2-phenylvinylboronic acid (112 mg, 0.74 mmol) in 1,4-dioxane: H$_2$O (3 mL/2 mL) was added Na$_2$CO$_3$ (153 mg, 1.45 mmol), followed by stirring at 90° C. overnight. To the reaction mixture was added H$_2$O (10 mL) and the aqueous layer was extracted with EtOAc (10 mL×2). The combined organic layer was washed with brine, dried (Na$_2$SO$_4$), filtered and concentrated under reduced pressure. Crude was subjected to flash column chromatography on silica gel to provide the title compound (216 mg, 90%) as a light yellow oil which solidified upon standing. $^1$H NMR (500 MHz, CDCl$_3$) δ 7.80 (d, J=16.1 Hz, 1H), 7.74 (s, 1H), 7.63 (d, J=7.6 Hz, 2H), 7.41 (t, J=7.6 Hz, 2H), 7.39-7.33 (m, 3H), 7.30 (t, J=7.7 Hz, 3H), 7.07 (t, J=7.4 Hz, 1H), 6.98 (d, J=8.6 Hz, 2H), 6.95 (d, J=8.3 Hz, 2H), 5.69 (s, 2H), 4.51 (q, J=7.1 Hz, 2H), 2.71 (s, 3H), 1.49 (t, J=7.0 Hz, 3H). $^{13}$C NMR (125 MHz, CDCl$_3$) δ 165.76, 157.04, 156.79, 154.93, 152.39, 141.19, 136.28, 134.74, 133.60, 132.13, 129.69, 129.50, 128.81, 127.69, 127.33, 123.28, 118.94, 118.82, 116.48, 110.28, 61.93, 49.80, 16.30, 14.30.

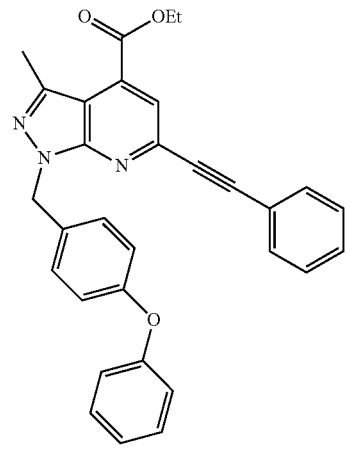

Ethyl 3-methyl-1-(4-phenoxybenzyl)-6-(phenylethynyl)-1H-pyrazolo[3,4-b]pyridine-4-carboxylate (53)

(see, e.g., Dai, W., et al., Org Lett 2006, 8, 4665-7). A mixture of 50 (95 mg, 0.22 mmol), Pd(PPh$_3$)$_2$Cl$_2$ (16 mg, 0.02 mmol), and CuI (8.6 mg, 0.04 mmol) in Et$_3$N (0.5 mL) and dry THF (1 mL) was added dropwise to a solution of phenylacetylene (40 µL, 0.36 mmol) in Et$_3$N (0.5 mL) under nitrogen at room temperature. Reaction mixture was heated to 60° C. and stirred overnight then diluted with EtOAc (10 mL) and washed with saturated aqueous NH$_4$Cl (15 mL×2) and brine (15 mL). The organic layer was dried (Na$_2$SO$_4$), filtered, concentrated under reduced pressure. The crude was purified by flash column chromatography on silica gel to give the title compound (33 mg, 31%) as an orange oil. $^1$H NMR (500 MHz, CDCl$_3$) δ 7.81 (s, 1H), 7.68-7.63 (m, 2H), 7.42-7.37 (m, 3H), 7.35-7.29 (m, 4H), 7.08 (t, J=7.6 Hz, 1H), 6.97 (d, J=8.4 Hz, 2H), 6.93 (d, J=8.4 Hz, 2H), 5.68 (s, 2H), 4.50 (q, J=7.1 Hz, 2H), 2.72 (s, 3H), 1.47 (t, J=7.1 Hz, 3H). $^{13}$C NMR (125 MHz, CDCl$_3$) δ 165.08, 157.02, 156.83, 152.00, 141.84, 141.44, 133.56, 132.20, 131.77, 129.69, 129.47, 129.36, 128.45, 123.28, 121.86, 121.06, 118.94, 118.81, 110.56, 90.88, 88.87, 62.09, 49.81, 16.24, 14.26.

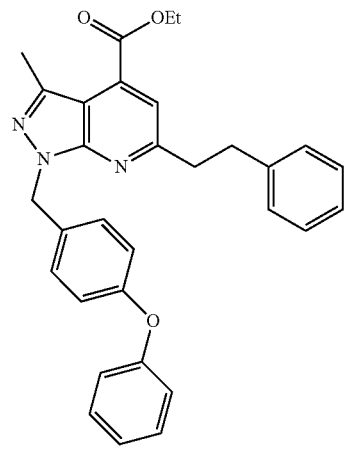

Ethyl 3-methyl-6-phenethyl-1-(4-phenoxybenzyl)-1H-pyrazolo[3,4-b]pyridine-4-carboxylate (54)

(see, e.g., WO2013039988A1). To a suspension of 10% Pd/C (70 mg) in EtOH (5 mL) was added 52 (186 mg, 0.38 mmol) dissolved in THF (1.5 mL). The suspension was stirred under an atmosphere of hydrogen (ca. 1 atm, balloon) overnight. The suspension was filtered through a pad of celite and the filtrate was concentrated under reduced pressure to provide the title compound (159 mg, 84%) as a light brown oil. Crude was used in the next reaction without further purification. $^1$H NMR (500 MHz, CDCl$_3$) δ 7.44 (s, 1H), 7.36-7.31 (m, 3H), 7.31-7.26 (m, 3H), 7.26-7.22 (m, 2H), 7.19 (t, J=7.0 Hz, 1H), 7.09 (t, J=7.4 Hz, 1H), 7.00 (d, J=7.9 Hz, 2H), 6.95 (d, J=8.5 Hz, 2H), 5.67 (s, 2H), 4.49 (q, J=7.1 Hz, 2H), 3.35-3.27 (m, 2H), 3.24-3.17 (m, 2H), 2.73 (s, 3H), 1.47 (t, J=7.1 Hz, 3H). $^{13}$C NMR (125 MHz, CDCl$_3$) δ 165.85, 161.09, 157.08, 156.78, 152.23, 141.30, 140.97, 133.36, 132.21, 129.72, 129.55, 128.49, 128.41, 126.04, 123.30, 118.95, 118.80, 117.33, 109.68, 61.83, 49.83, 39.82, 35.23, 16.31, 14.30. ESI MS: m/z 516.9 (M+H)$^+$.

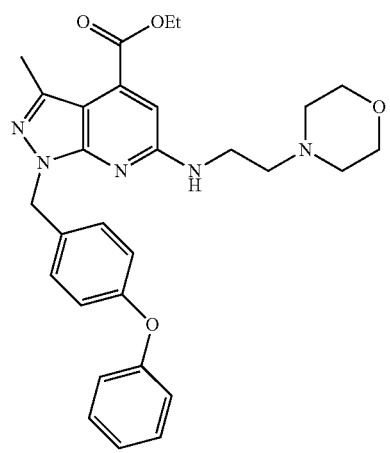 [SMILES: CCOC(=O)c1cc(NCCN2CCOCC2)nc2c1c(C)nn2Cc1ccc(Oc2ccccc2)cc1]

Ethyl 3-methyl-6-((2-morpholinoethyl)amino)-1-(4-phenoxybenzyl)-1H-pyrazolo[3,4-b]pyridine-4-carboxylate (55)

(see, e.g., WO2013039988A1). A pressure vessel was charged with 50 (121 mg, 0.29 mmol), 4-(2-aminoethyl)morpholine (1.0 mL, 7.6 mmol) and iPrOH (3 mL) and NMP (1 mL). The vessel was sealed and the reaction mixture was heated at 150° C. overnight. The reaction mixture was diluted with EtOAc (20 mL) and washed with H$_2$O (10 mL×3) to remove NMP. Combined organic layers were washed with brine, dried (Na$_2$SO$_4$), filtered, and concentrated under reduced pressure. Crude was subjected to flash column chromatography on silica gel to provide the title compound (40 mg, 26%) as a yellow oil. $^1$H NMR (500 MHz, CDCl$_3$) δ 7.29 (q, J=7.1, 6.6 Hz, 4H), 7.07 (t, J=7.1 Hz, 1H), 6.96 (d, J=8.6 Hz, 2H), 6.91 (d, J=8.3 Hz, 2H), 6.78 (s, 1H), 5.46 (s, 2H), 4.43 (q, J=7.1 Hz, 2H), 3.76-3.70 (m, 4H), 3.55 (q, J=5.0 Hz, 2H), 2.63 (t, J=5.7 Hz, 2H), 2.58 (s, 3H), 2.49 (s, 4H), 1.42 (t, J=7.1 Hz, 3H). $^{13}$C NMR (126 MHz, CDCl$_3$) δ 166.00, 157.47, 157.15, 156.51, 152.39, 141.23, 134.44, 132.67, 129.66, 129.31, 123.18, 118.83, 118.77, 107.03, 103.90, 66.92, 61.62, 57.03, 53.40, 49.37, 37.75, 16.16, 14.26.

A Representative Procedure for Synthesis of Carboxylic Acids.

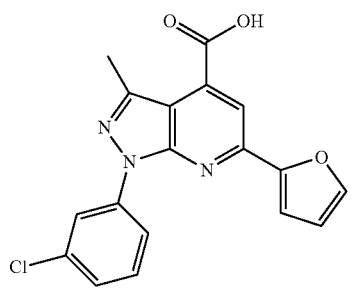 [SMILES: Cc1nn(-c2cccc(Cl)c2)c2nc(-c3ccco3)cc(C(=O)O)c12]

1-(3-Chlorophenyl)-6-(furan-2-yl)-3-methyl-1H-pyrazolo[3,4-b]pyridine-4-carboxylic acid (1)

(see, e.g., Volochnyuk, D. M., et al., J Comb Chem 2010, 12, 510-7). A solution of ester 35 (108 mg, 0.29 mmol) and KOH (29 mg, 0.52 mmol) in iPrOH (6 mL) was refluxed for 1 h 30 min. Reaction mixture was diluted with H$_2$O (10 mL) and washed with EtOAc (10 mL×2). Aqueous layer was acidified with 1N HCl and extracted with EtOAc (10 mL×2). Combined organic extracts were washed with brine, dried (Na$_2$SO$_4$), filtered, and concentrated under reduced pressure to give 1 (88 mg, 86%) as a bright yellow solid. 99% pure by HPLC. $^1$H NMR (400 MHz, DMSO-d$_6$) δ 8.35 (s, 1H), 8.29 (d, J=8.5 Hz, 1H), 7.96 (s, 1H), 7.92 (s, 1H), 7.55 (t, J=8.1 Hz, 1H), 7.37-7.31 (m, 2H), 6.76-6.71 (m, 1H), 2.62 (s, 3H). $^{13}$C NMR (100 MHz, DMSO-d$_6$) δ 166.48, 152.40, 151.70, 148.29, 146.21, 143.65, 140.42, 136.54, 133.86, 131.32, 125.57, 119.83, 118.66, 113.69, 113.32, 112.21, 112.10, 16.20. ESI MS: m/z 354.0 (M+H)$^+$.

6-(Furan-2-yl)-3-methyl-1-phenyl-1H-pyrazolo[3,4-b]pyridine-4-carboxylic acid (2)

Synthesized using the procedure for 1 except ester 36 was used as the starting material. The title compound (288 mg, 90%) was obtained as a white solid. 100% pure by HPLC. $^1$H NMR (400 MHz, DMSO-d$_6$) δ 8.26 (d, J=7.7 Hz, 2H), 7.95 (s, 2H), 7.55 (t, J=7.5 Hz, 2H), 7.39 (s, 1H), 7.32 (t, J=7.4 Hz, 1H), 6.73 (s, 1H), 2.65 (s, 3H). $^{13}$C NMR (100 MHz, DMSO-d$_6$) δ 166.68, 152.54, 151.60, 148.24, 146.07, 142.86, 139.27, 136.37, 129.60, 126.17, 120.94, 113.46, 113.27, 112.07, 111.82, 16.17. ESI MS: m/z 320.1 (M+H)$^+$.

6-(Furan-2-yl)-1,3-dimethyl-1H-pyrazolo[3,4-b]pyridine-4-carboxylic acid (3)

Synthesized using the procedure for 1 except ester 37 was used as the starting material. After the work up and acidifying the aqueous layer with 1N HCl, solid precipitated which was filtered off and dried on high vacuum to provide the title compound (203 mg, 79%) as a beige solid. 100% pure by HPLC. $^1$H NMR (400 MHz, DMSO-d$_6$) δ 13.91 (s, 1H), 7.91 (s, 1H), 7.85 (s, 1H), 7.33 (d, J=2.9 Hz, 1H), 6.72-6.67 (m, 1H), 3.98 (s, 3H), 2.55 (s, 3H). $^{13}$C NMR (100 MHz, DMSO-d$_6$) δ 166.91, 152.73, 152.00, 147.61, 145.67, 140.08, 135.59, 113.13, 112.56, 111.40, 109.74, 33.82, 15.92. ESI MS: m/z 258.0 (M+H)$^+$.

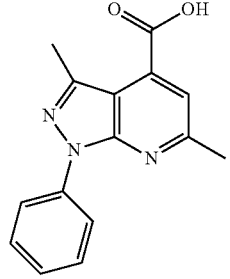 [SMILES: Cc1cc(C(=O)O)c2c(C)nn(-c3ccccc3)c2n1]

3,6-Dimethyl-1-phenyl-1H-pyrazolo[3,4-b]pyridine-4-carboxylic acid (4)

Synthesized using the procedure for 1 except ester 46 was used as the starting material. After the work up and acidifying the aqueous layer with 1N HCl, solid precipitated which was filtered off and dried on high vacuum to provide the title compound (165 mg, 81%) as a light yellow solid. 100% pure by HPLC. $^1$H NMR (400 MHz, DMSO-$d_6$) δ 13.90 (s, 1H), 8.19 (d, J=7.7 Hz, 2H), 7.56-7.48 (m, 3H), 7.29 (t, J=7.3 Hz, 1H), 2.65 (s, 3H), 2.63 (s, 3H). $^{13}$C NMR (100 MHz, DMSO-$d_6$) δ 167.04, 159.52, 151.67, 142.43, 139.35, 135.32, 129.49, 126.12, 121.13, 118.29, 111.04, 24.92, 16.12. ESI MS: m/z 268.1 (M+H)$^+$.

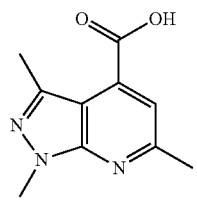

1,3,6-Trimethyl-1H-pyrazolo[3,4-b]pyridine-4-carboxylic acid (12)

Synthesized using the procedure for 1 except ester 47 was used as the starting material. The title compound (157 mg, 84%) was obtained as a white solid. 95% pure by HPLC. $^1$H NMR (400 MHz, DMSO-$d_6$) δ 7.37 (s, 1H), 3.92 (s, 3H), 2.60 (s, 3H), 2.53 (s, 3H). $^{13}$C NMR (100 MHz, CDCl$_3$) δ 167.25, 158.47, 152.04, 139.56, 134.57, 117.22, 108.94, 33.73, 24.66, 15.89. ESI MS: m/z 206.1 (M+H)$^+$.

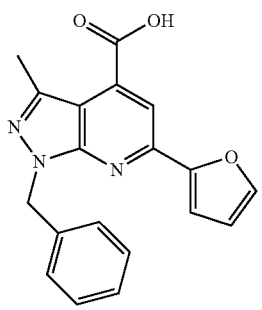 [SMILES: Cc1nn(Cc2ccccc2)c2nc(-c3ccco3)cc(C(=O)O)c12]

1-Benzyl-6-(furan-2-yl)-3-methyl-1H-pyrazolo[3,4-b]pyridine-4-carboxylic acid (6)

Synthesized using the procedure for 1 except ester 38 was used as the starting material. The title compound (67 mg, quantitative yield) was obtained as a light yellow solid. 100% pure by HPLC. $^1$H NMR (500 MHz, DMSO-$d_6$) δ 8.08-8.03 (m, 1H), 8.03-7.98 (m, 1H), 7.43 (s, 1H), 7.33-7.27 (m, 2H), 7.27-7.20 (m, 3H), 6.78 (s, 1H), 5.67 (s, 2H), 2.65 (s, 3H). $^{13}$C NMR (125 MHz, DMSO-$d_6$) δ 166.49, 151.92, 150.08, 147.52, 146.28, 140.99, 137.81, 133.82, 128.98, 127.93, 113.74, 113.56, 113.34, 110.95, 50.03, 16.86. ESI MS: m/z 334.2 (M+H)$^+$.

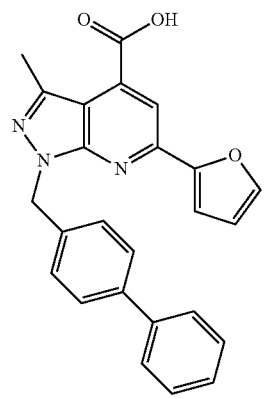 [SMILES: Cc1nn(Cc2ccc(-c3ccccc3)cc2)c2nc(-c3ccco3)cc(C(=O)O)c12]

1-([1,1'-Biphenyl]-4-ylmethyl)-6-(furan-2-yl)-3-methyl-1H-pyrazolo[3,4-b]pyridine-4-carboxylic acid (7)

Synthesized using the procedure for 1 except ester 39 was used as the starting material. The title compound (58 mg, 87%) was obtained as a light yellow solid. 100% pure by HPLC. $^1$H NMR (500 MHz, DMSO-$d_6$) δ 13.47 (s, 1H), 8.04 (d, J=16.4 Hz, 1H), 7.59 (d, J=7.4 Hz, 5H), 7.45-7.39 (m, 3H), 7.33 (d, J=7.6 Hz, 3H), 6.78 (s, 1H), 5.72 (s, 2H), 2.67 (s, 3H). $^{13}$C NMR (125 MHz, DMSO-$d_6$) δ 166.48, 151.95, 150.09, 147.53, 146.30, 141.05, 140.19, 139.91, 136.98, 133.86, 129.34, 128.57, 127.89, 127.35, 127.07, 113.77, 113.60, 113.35, 111.00, 49.75, 16.89. ESI MS: m/z 410.2 (M+H)$^+$.

6-(Furan-2-yl)-3-methyl-1-(4-phenoxybenzyl)-1H-pyrazolo[3,4-b]pyridine-4-carboxylic acid (8)

Synthesized using the procedure for 1 except ester 40 was used as the starting material. The title compound (63 mg, 43%) was obtained as an orange solid. 99% pure by HPLC. $^1$H NMR (500 MHz, DMSO-$d_6$) δ 7.94 (s, 1H), 7.91 (s, 1H), 7.40 (d, J=3.4 Hz, 1H), 7.34 (t, J=7.8 Hz, 2H), 7.31 (d, J=8.4 Hz, 2H), 7.10 (t, J=7.2 Hz, 1H), 6.95 (t, J=8.1 Hz, 4H), 6.74-6.71 (m, 1H), 5.61 (s, 2H), 2.59 (s, 3H). $^{13}$C NMR (125 MHz, DMSO-$d_6$) δ 166.87, 156.95, 156.51, 152.71, 151.97, 147.92, 145.83, 140.95, 135.93, 132.85, 130.46, 129.94, 123.92, 119.10, 119.04, 113.21, 112.86, 111.69, 109.96, 49.50, 16.04. ESI MS: m/z 426.0 (M+H)$^+$.

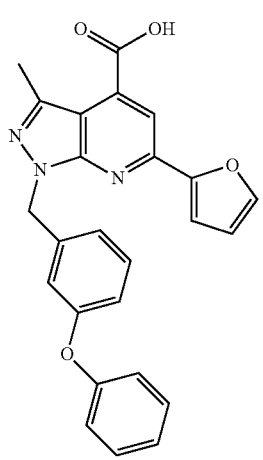 [SMILES: Cc1nn(Cc2cccc(Oc3ccccc3)c2)c2nc(-c3ccco3)cc(C(=O)O)c12]

6-(Furan-2-yl)-3-methyl-1-(3-phenoxybenzyl)-1H-pyrazolo[3,4-b]pyridine-4-carboxylic acid (9)

Synthesized using the procedure for 1 except ester 41 was used as the starting material. The title compound (84 mg, 86%) was obtained as a light orange solid. 99% pure by HPLC. $^1$H NMR (500 MHz, DMSO-d$_6$) δ 7.91 (s, 1H), 7.89 (s, 1H), 7.33-7.26 (m, 4H), 7.09 (t, J=7.4 Hz, 1H), 6.97 (d, J=7.6 Hz, 1H), 6.93 (d, J=8.3 Hz, 2H), 6.88 (s, 1H), 6.85 (d, J=9.8 Hz, 1H), 6.72-6.69 (m, 1H), 5.60 (s, 2H), 2.56 (s, 3H). $^{13}$C NMR (125 MHz, DMSO-d$_6$) δ 166.83, 157.39, 156.47, 152.64, 152.08, 147.91, 145.80, 141.07, 140.01, 135.92, 130.63, 130.41, 124.11, 122.72, 119.34, 117.73, 117.65, 113.17, 112.89, 111.65, 109.95, 49.77, 16.01. ESI MS: m/z 426.2 (M+H)$^+$.

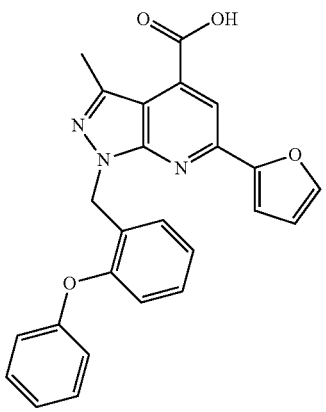 [SMILES: Cc1nn(Cc2ccccc2Oc2ccccc2)c2nc(-c3ccco3)cc(C(=O)O)c12]

6-(Furan-2-yl)-3-methyl-1-(2-phenoxybenzyl)-1H-pyrazolo[3,4-b]pyridine-4-carboxylic acid (10)

Synthesized using the procedure for 1 except ester 42 was used as the starting material. The title compound (86 mg, quantitative yield) was obtained as a yellow oil which solidified upon standing. 100% pure by HPLC. $^1$H NMR (500 MHz, DMSO-d$_6$) δ 13.88 (s, 1H), 7.90 (s, 1H), 7.84 (s, 1H), 7.31-7.20 (m, 4H), 7.11-7.06 (m, 2H), 7.01 (t, J=7.4 Hz, 1H), 6.89 (d, J=8.0 Hz, 1H), 6.80 (d, J=7.7 Hz, 2H), 6.70-6.66 (m, 1H), 5.65 (s, 2H), 2.53 (s, 3H). $^{13}$C NMR (125 MHz, DMSO-d$_6$) δ 166.84, 157.37, 153.97, 152.72, 152.16, 147.73, 145.69, 140.97, 135.69, 130.19, 130.12, 129.76, 129.16, 124.60, 123.28, 119.94, 117.86, 113.11, 112.76, 111.43, 109.86, 45.04, 16.02. ESI MS: m/z 426.1 (M+H)$^+$.

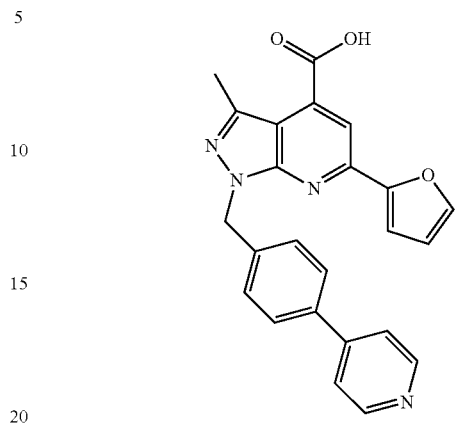

6-(Furan-2-yl)-3-methyl-1-(4-(pyridin-4-yl)benzyl)-1H-pyrazolo[3,4-b]pyridine-4-carboxylic acid (11)

Synthesized using the procedure for 1 except ester 43 was used as the starting material. The title compound (31 mg, 32%) was obtained as an off-white solid. $^1$H NMR (400 MHz, DMSO-d$_6$) δ 8.68 (d, J=5.8 Hz, 2H), 7.94 (s, 1H), 7.92 (s, 1H), 7.85-7.80 (m, 3H), 7.79 (s, 1H), 7.42 (s, 1H), 7.40 (s, 2H), 6.74-6.70 (m, 1H), 5.71 (s, 2H), 2.59 (s, 3H). $^{13}$C NMR (100 MHz, DMSO-d$_6$) δ 166.85, 152.65, 152.12, 149.44, 148.39, 147.99, 145.89, 141.18, 139.74, 136.00, 128.91, 127.90, 122.31, 113.22, 112.97, 111.79, 109.99, 49.69, 16.06. ESI MS: m/z 411.1 (M+H)$^+$.

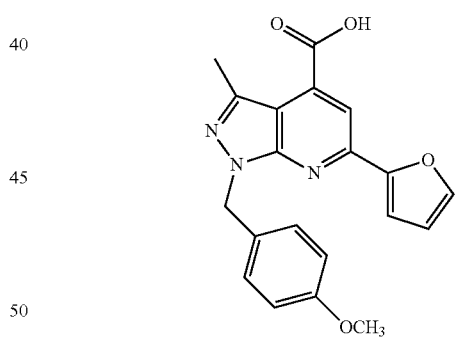

6-(Furan-2-yl)-1-(4-methoxybenzyl)-3-methyl-1H-pyrazolo[3,4-b]pyridine-4-carboxylic acid (12)

Synthesized using the procedure for 1 except ester 44 was used as the starting material. The title compound (158 mg, 99%) was obtained as an off-white solid. 100% pure by HPLC. $^1$H NMR (500 MHz, DMSO-d$_6$) δ 13.92 (s, 1H), 7.94 (s, 1H), 7.88 (s, 1H), 7.39 (s, 1H), 7.24 (d, J=6.9 Hz, 2H), 6.85 (d, J=6.8 Hz, 2H), 6.72 (s, 1H), 5.54 (s, 2H), 3.68 (s, 3H), 2.57 (s, 3H). $^{13}$C NMR (125 MHz, DMSO-d$_6$) δ 166.90, 159.13, 152.77, 151.87, 147.81, 145.78, 140.74, 135.94, 129.79, 129.59, 114.35, 113.19, 112.74, 111.58, 109.96, 55.49, 49.63, 16.01. ESI MS: m/z 364.2 (M+H)$^+$.

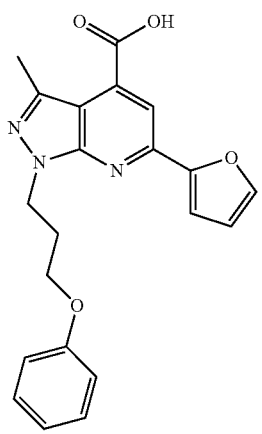 [SMILES: Cc1nn(CCCOc2ccccc2)c2nc(-c3ccco3)cc(C(=O)O)c12]

6-(Furan-2-yl)-3-methyl-1-(3-phenoxypropyl)-1H-pyrazolo[3,4-b]pyridine-4-carboxylic acid (13)

Synthesized using the procedure for 1 except ester 45 was used as the starting material. The title compound (122 mg, 81%) was obtained as a yellow solid. 99% pure by HPLC. $^1$H NMR (400 MHz, DMSO-$d_6$) δ 13.91 (s, 1H), 7.90 (s, 1H), 7.84 (s, 1H), 7.25-7.16 (m, 3H), 6.90-6.81 (m, 3H), 6.70-6.63 (m, 1H), 4.58 (t, J=6.4 Hz, 2H), 3.97 (t, J=5.2 Hz, 2H), 2.57 (s, 3H), 2.35-2.24 (m, 2H). $^{13}$C NMR (101 DMSO-$d_6$) δ 166.93, 158.83, 152.70, 152.02, 147.61, 145.64, 140.43, 135.68, 129.81, 120.92, 114.83, 113.10, 112.66, 111.37, 109.87, 65.17, 43.71, 29.32, 16.04. ESI MS: m/z 378.2 (M+H)$^+$.

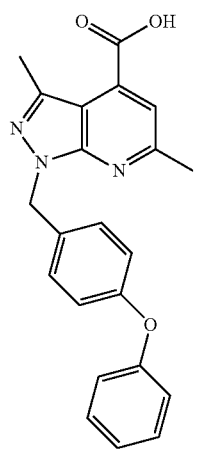 [SMILES: Cc1cc(C(=O)O)c2c(C)nn(Cc3ccc(Oc4ccccc4)cc3)c2n1]

3,6-Dimethyl-1-(4-phenoxybenzyl)-1H-pyrazolo[3,4-b]pyridine-4-carboxylic acid (14)

Synthesized using the procedure for 1 except ester 48 was used as the starting material. The title compound (11 mg, 20%) was obtained as an off-white solid. 97% pure by HPLC. $^1$H NMR (400 MHz, DMSO-$d_6$) δ 7.42 (s, 1H), 7.34 (t, J=7.6 Hz, 2H), 7.22 (d, J=8.1 Hz, 2H), 7.10 (t, J=6.8 Hz, 1H), 6.98-6.88 (m, 4H), 5.55 (s, 2H), 2.63 (s, 3H), 2.55 (s, 3H). $^{13}$C NMR (100 MHz, DMSO-$d_6$) δ 167.28, 158.92, 156.97, 156.39, 152.02, 140.48, 133.05, 130.46, 129.66, 123.90, 119.09, 119.00, 117.53, 109.99, 109.14, 49.25, 24.80, 15.98. ESI MS: m/z 374.0 (M+H)$^+$.

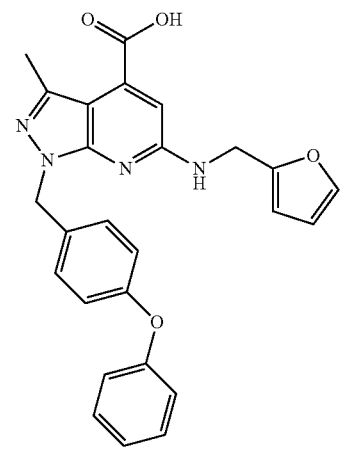 [SMILES: Cc1nn(Cc2ccc(Oc3ccccc3)cc2)c2nc(NCc3ccco3)cc(C(=O)O)c12]

6-((Furan-2-ylmethyl)amino)-3-methyl-1-(4-phenoxybenzyl)-1H-pyrazolo[3,4-b]pyridine-4-carboxylic acid (15)

(see, e.g., Neres, J., et al., J Med Chem 2013, 56, 2385-405). A solution of ester 51 (40 mg, 0.08 mmol) and 1N NaOH (3.5 mL, 3.5 mmol) in THF (1.5 mL) was refluxed for 3 h. Reaction mixture was diluted with water (10 mL) and washed with EtOAc (10 mL×2). Aqueous layer was acidified with 1N HCl and extracted with EtOAc (10 mL×2). Combined organic extracts were washed with brine, dried (Na$_2$SO$_4$) and filtered. The solvent was removed under reduced pressure to give the title compound (22 mg, 61%) as an orange solid. 99% pure by HPLC. $^1$H NMR (500 MHz, DMSO-$d_6$) δ 7.79 (t, J=5.1 Hz, 1H), 7.54 (s, 1H), 7.34 (t, J=7.6 Hz, 2H), 7.27 (d, J=8.1 Hz, 2H), 7.10 (t, J=6.8 Hz, 1H), 6.95 (d, J=7.9 Hz, 2H), 6.90 (d, J=8.3 Hz, 2H), 6.86 (s, 1H), 6.33 (s, 1H), 6.25 (s, 1H), 5.35 (s, 2H), 4.57 (d, J=5.2 Hz, 2H), 2.41 (s, 3H). $^{13}$C NMR (125 MHz, DMSO-$d_6$) δ 167.35, 157.85, 157.05, 156.29, 153.26, 152.02, 142.37, 140.38, 135.41, 133.48, 130.46, 130.44, 130.08, 123.85, 118.98, 118.97, 110.81, 107.38, 103.37, 49.09, 37.87, 15.96. ESI MS: m/z 455.0 (M+H)$^+$.

A Modified Procedure for Synthesis of Carboxylic Acids.

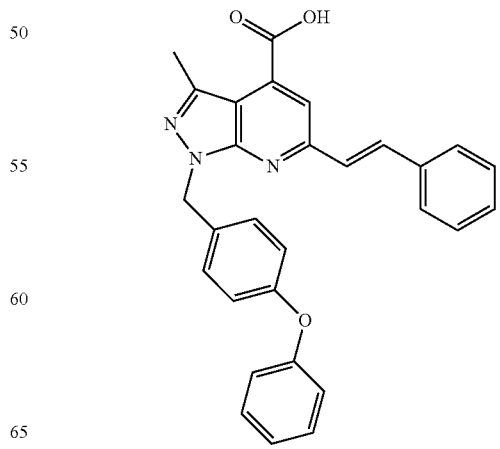

(E)-3-methyl-1-(4-phenoxybenzyl)-6-styryl-1H-pyrazolo[3,4-b]pyridine-4-carboxylic acid (16)

A solution of ester 52 (56 mg, 0.11 mmol) and KOH (19 mg, 0.34 mmol) in iPrOH:THF (2 mL/1 mL) was refluxed at 87° C. for 2 h. Reaction mixture was diluted with water (10 mL) and washed with EtOAc (10 mL×2). Aqueous layer was acidified with 1N HCl and extracted with EtOAc (10 mL×2). Combined organic extracts were washed with brine, dried (Na$_2$SO$_4$) and filtered. The solvent was removed under reduced pressure to give the title compound (45 mg, 94%) as a yellow solid. 88% pure by HPLC. $^1$H NMR (500 MHz, DMSO-d$_6$) δ 13.86 (s, 1H), 7.87 (d, J=16.2 Hz, 1H), 7.81 (s, 1H), 7.74 (d, J=7.8 Hz, 2H), 7.52 (d, J=16.2 Hz, 1H), 7.42 (t, J=7.5 Hz, 2H), 7.37-7.29 (m, 5H), 7.09 (t, J=7.4 Hz, 1H), 6.98-6.92 (m, 4H), 5.64 (s, 2H), 2.58 (s, 3H). $^{13}$C NMR (125 MHz, DMSO-d$_6$) δ 167.16, 156.97, 156.47, 155.22, 152.20, 140.74, 136.47, 135.39, 134.92, 133.00, 130.46, 129.90, 129.30, 128.04, 127.87, 123.90, 119.11, 119.02, 116.60, 110.13, 49.41, 16.02. ESI MS: m/z 462.0 (M+H)$^+$.

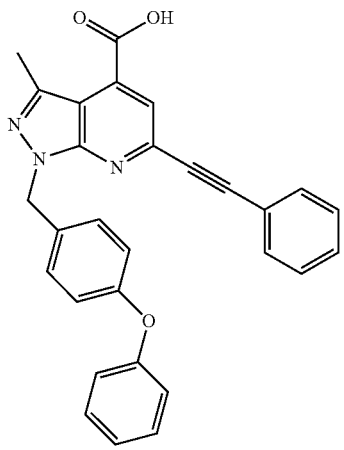

3-Methyl-1-(4-phenoxybenzyl)-6-(phenylethynyl)-1H-pyrazolo[3,4-b]pyridine-4-carboxylic acid (17)

Synthesized using the procedure for 16 except ester 53 was used as the starting material. The title compound (13 mg, 39%) was obtained as a light brown solid. 98% pure by HPLC. $^1$H NMR (500 MHz, DMSO-d$_6$) δ 7.75 (s, 1H), 7.69 (d, J=7.1 Hz, 2H), 7.51-7.45 (m, 3H), 7.35 (t, J=7.6 Hz, 2H), 7.24 (d, J=8.3 Hz, 2H), 7.10 (t, J=6.9 Hz, 1H), 6.96 (t, J=8.4 Hz, 4H), 5.63 (s, 2H), 2.61 (s, 3H). $^{13}$C NMR (125 MHz, DMSO-d$_6$) δ 166.45, 156.94, 156.51, 151.85, 141.39, 141.14, 132.72, 132.43, 130.46, 130.35, 129.62, 129.37, 123.93, 121.34, 120.69, 119.13, 119.05, 110.56, 90.88, 89.26, 49.53, 15.97. ESI MS: m/z 460.0 (M+H)$^+$.

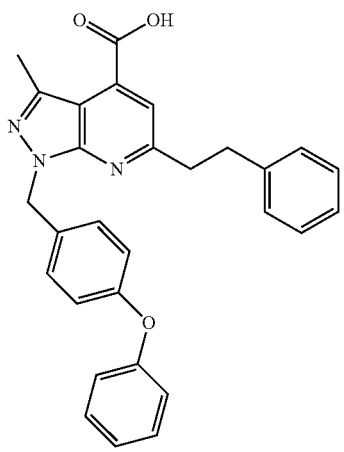

3-Methyl-6-phenethyl-1-(4-phenoxybenzyl)-1H-pyrazolo[3,4-b]pyridine-4-carboxylic acid (18)

Synthesized using the procedure for 16 except ester 54 was used as the starting material. The title compound (67 mg, 91%) was obtained as a white solid. 96% pure by HPLC. $^1$H NMR (500 MHz, DMSO-d$_6$) δ 13.75 (s, 1H), 7.44 (s, 1H), 7.34 (t, J=7.5 Hz, 2H), 7.24 (d, J=8.0 Hz, 2H), 7.22-7.17 (m, 4H), 7.11 (t, J=6.8 Hz, 2H), 6.95 (d, J=8.2 Hz, 2H), 6.91 (d, J=8.0 Hz, 2H), 5.57 (s, 2H), 3.24 (t, J=7.6 Hz, 2H), 3.09 (t, J=7.5 Hz, 2H), 2.55 (s, 3H). $^{13}$C NMR (125 MHz, DMSO-d$_6$) δ 167.24, 161.61, 156.94, 156.49, 151.91, 141.54, 140.43, 134.92, 132.98, 130.46, 129.89, 128.85, 128.64, 126.26, 123.95, 119.08, 119.00, 117.34, 109.43, 49.45, 34.84, 15.99. ESI MS: m/z 464.1 (M+H)$^+$.

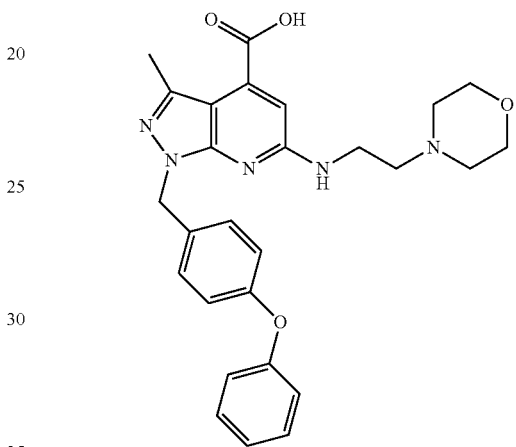

3-Methyl-6-((2-morpholinoethyl)amino)-1-(4-phenoxybenzyl)-1H-pyrazolo[3,4-b]pyridine-4-carboxylic acid (19)

Synthesized using the procedure for 1 except ester 55 was used as the starting material. The title compound (35 mg, 89%) was obtained as a white solid. 100% pure by HPLC. $^1$H NMR (400 MHz, DMSO-d$_6$) δ 13.50 (s, 1H), 11.03 (s, 1H), 7.79-7.71 (m, 1H), 7.39-7.32 (m, 2H), 7.32-7.26 (m, 2H), 7.14-7.07 (m, 1H), 6.99-6.90 (m, 3H), 6.81 (s, 1H), 5.40 (s, 2H), 4.05-3.97 (m, 2H), 3.84-3.73 (m, 3H), 3.40-3.26 (m, 3H), 2.42 (s, 3H), 1.97 (s, 2H), 1.19-1.12 (m, 2H). $^{13}$C NMR (100 MHz, DMSO-d$_6$) δ 167.26, 157.73, 157.04, 156.29, 151.98, 140.48, 135.53, 133.48, 130.47, 129.99, 123.88, 119.05, 118.97, 107.78, 103.53, 63.55, 60.20, 55.24, 51.64, 49.09, 21.22, 16.00, 14.54. ESI MS: m/z 488.0 (M+H)$^+$.

Protein Purification

His-tagged proteins containing Mcl-1 (residues 171-327), Bcl-2 (residues 1-202 with inserted Bcl-X$_L$ sequence from residues 35 to 50), Bcl-X$_L$ (residues 1-209 lacking its C-terminal transmembrane domain with a deletion of the flexible loop region 45-85) were expressed from the pHis-TEV vector (a modified pET vector) in *E. coli* BL21 (DE3) cells. Cells were grown at 37° C. in 2×YT containing antibiotics to an $OD_{600}$ density of 0.6. Protein expression was induced by 0.4 mM IPTG at 37° C. for 4 hours. Cells were lysed in 50 mM Tris pH 8.0 buffer containing 500 mM NaCl, 0.1% bME and 40 µl of Leupectin/Aprotin. All proteins were purified from the soluble fraction using Ni-NTA resin (QIAGEN), following the manufacturer's instructions. Mcl-1 was further purified on a Source Q15 column (Amersham Biosciences) in 25 mM Tris pH 8.0 buffer, with NaCl gradient. Bcl-2 and Bcl-$X_L$ were purified on a Superdex75 column (Amersham Biosciences) in 25 mM Tris pH 8.0 buffers containing 150 mM NaCl and 2 mM DTT and at −80° C. in presence of 25% Glycerol.

Determination of the $K_d$ Values of Fluorescent Probes to Anti-Apoptotic Proteins Fluorescein tagged BID BH3 (Bcl-2 Homology 3) peptide was used as a fluorescent probe in the FP-based binding assays. Two fluorescent labeled BID BH3 peptide probes were used: i) fluorescein tagged BID peptide (Flu-BID), labeled with fluorescein on the N-terminus of the BH3 peptide (79-99); ii) the second tracer was purchased from Abgent (Catalog # SP2121a), named as FAM-BID, where the BH3 peptide (80-99) is labeled with 5-FAM. Their $K_d$ values were determined to all members of the Bcl-2 family proteins with a fixed concentration of the tracer (2 nM of Flu-BID and FAM-BID) and different concentrations of the tested proteins, in a final volume of 125 µl in the assay buffer (20 mM phosphate pH 7.4, 50 mM NaCl, 1 mM EDTA. 0.05% Pluronic F68 and 4% DMSO). Plates were mixed and incubated at room temperature for 2 hours and the polarization values in millipolarization units (mP) were measured at an excitation wavelength of 485 nm and an emission wavelength of 530 nm. Equilibrium dissociation constants ($K_d$) were calculated by fitting the sigmoidal dose-dependent FP increases as a function of protein concentrations using Graphpad Prism 6.0 software. Based upon analysis of the dynamic ranges for the signals and their $K_d$ values, Flu-BID was selected as the tracer in the Mcl-1 competitive binding assay, while FAM-BID was selected as the tracer for the Bcl-2 and Bcl-xL proteins. The $K_d$ value of Flu-BID to Mcl-1 was 2.3±0.3 nM, and the $K_d$ values of FAM-BID against Bcl-2 was 14.2±1.0 nM and to Bcl-xL was 24.1±7.6 nM respectively, in our saturation experiments.

Fluorescence Polarization-Based Binding Assays

Sensitive and quantitative FP-based binding assays were developed and optimized to determine the binding affinities of small-molecule inhibitors to the recombinant Mcl-1, A1/Bfl-1, Bcl-w, Bcl-2, and Bcl-xL proteins. The concentrations of the proteins used in the competitive binding experiments were 10 nM for Mcl-1, 80 nM for Bcl-xL, and 60 nM for Bcl-2. The fluorescent probes, Flu-BID or FAM-BID were fixed at 2 nM for all assays, which binds with Kd values of 2.3 nM, 14.2 nM and 24.1 nM against Mcl-1, Bcl-2 and Bcl-xL respectively. 5 µL of the tested compound in DMSO and 120 µL of protein/probe complex in the assay buffer (20 mM phosphate pH 7.4, 50 mM NaCl, 1 mM EDTA. 0.05% Pluronic F68)s) were added to 96 well black assay plates, incubated at room temperature for 3 h and the polarization values (mP) were measured at an excitation wavelength at 485 nm and an emission wavelength at 530 nm using the plate reader Synergy H1 Hybrid, BioTek. $IC_{50}$ values were determined by nonlinear regression fitting of the competition curves (GraphPad Prism 6.0 Software). The $K_i$ values were calculated as described previously (see, e.g., Nikolovska-Coleska, Z., et al., Anal Biochem 2004, 332, 261-73).

Molecular Modeling

Crystal structure of Mcl-1 in complex with mNoxa BH3 peptide (PDB entry 2NLA) and in silico Schrödinger's IFD were used to model the binding poses of our designed compounds with Mcl-1. IFD is allowing incorporation of the protein and ligand flexibility in the docking protocol, which is consisted of the following steps: (i) constrained minimization of the protein with an RMSD cutoff of 0.18 Å; (ii) initial Glide docking of the ligand using a softened potential (Van der Waals radii scaling); (iii) one round of Prime side-chain prediction for each protein/ligand complex, on residues within defined distance of any ligand pose; (iv) prime minimization of the same set of residues and the ligand for each protein/ligand complex pose; (v) Glide re-docking of each protein/ligand complex structure within a specified energy of the lowest energy structure; (vi) estimation of the binding energy (IFDScore) for each output pose. All docking calculations were run in the extra precision (XP) mode of Glide. The center of the grid box of the Mcl-1 was defined by the Val 249 (in h1), Phe 270 (in h2), Val 220 (in h3/h4) and Val 216 (in h4). The size of the grid box was set to 15 Å. Default values were used for all other parameters. Schrödinger's MC/SD dynamic simulation performs constant temperature calculations that take advantage of the strengths of Monte Carlo methods for quickly introducing large changes in a few degree of freedom, and stochastic dynamics for its effective local sampling of collective motions. The MC/SD dynamic simulation time in our study was set to 100 ps by allowing movement of the docked ligand and the residues which is less than 6 Å to the ligand. The force field used was set to OPLS_2001. Default values were used for all other parameters.

NMR Studies $^{15}$N-labeled or $^{15}$N, $^{13}$C-labeled Mcl-1 proteins for NMR studies were prepared and purified using the same protocol as for unlabeled protein with the exception that the bacteria were grown on M9 minimal media supported with 3 g/L of $^{13}$C-glucose and/or 1 g/L of $(^{15}NH_4)_2SO_4$. $^{15}$N, $^{13}$C-labeled Mcl-1 was used for backbone reassignment and 80% of residues were reassigned based on the work by Liu et al[26]. Protein samples were prepared in a 20 mM sodium phosphate, 150 mM NaCl and 1 mM DTT solution at pH 7 in 7% $D_2O$. The binding mode of the compounds has been characterized by recording $^1H$,$^{15}$N-HSQC experiments with a 138 µL solution of uniformly $^{15}$N-labeled Mcl-1 (75 µM) in the absence and presence of added compounds with the indicated molar ratio concentrations. All Spectra were acquired at 30° C. on a Bruker 600 MHz NMR spectrometer equipped with a cryogenic probe, processed using Bruker TopSpin and rNMR[25], and were analyzed with Sparky[27]. Plots of chemical shift changes were calculated as $((\Delta^1H \text{ ppm})^2+(0.2(\Delta^{15}N \text{ ppm}))^2)^{0.5}$ of Mcl-1 amide upon addition of compound. The absence of a bar in a chemical shift plot indicates no chemical shift difference, or the presence of a proline or residue that is overlapped or not assigned.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound having Formula I:

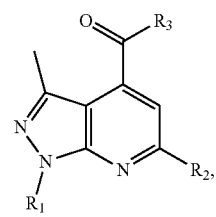

including pharmaceutically acceptable salts, solvates, and/or prodrugs thereof;

wherein R1 is selected from the group consisting of from

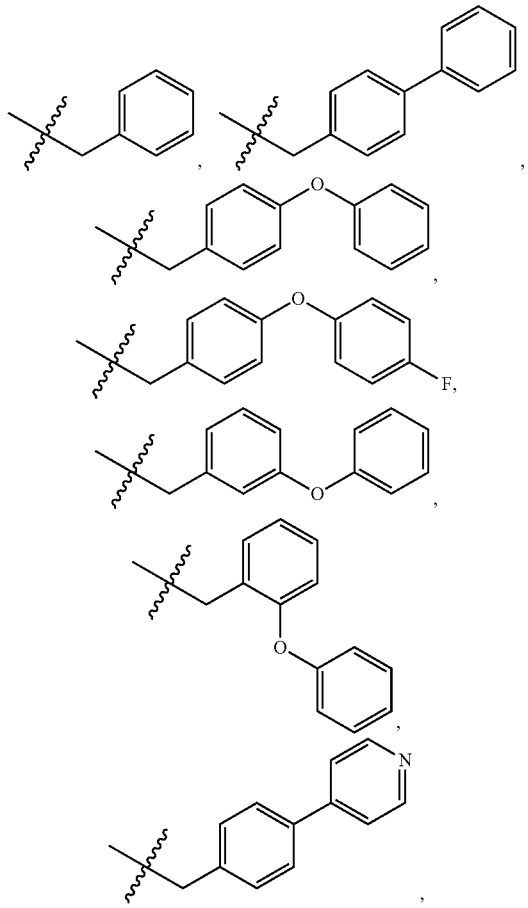

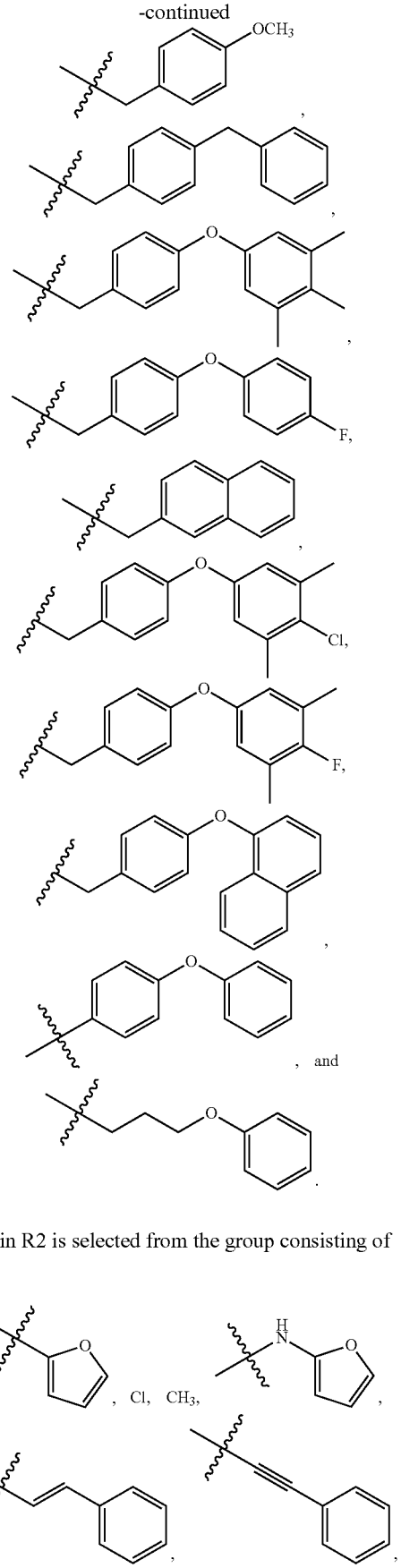

wherein R2 is selected from the group consisting of

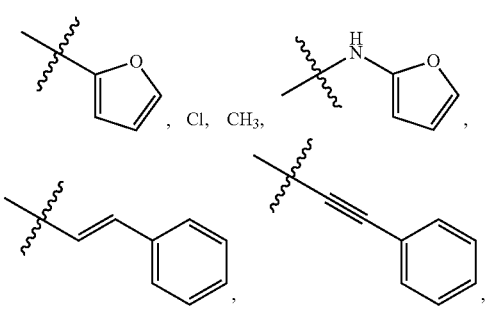, Cl, CH$_3$,

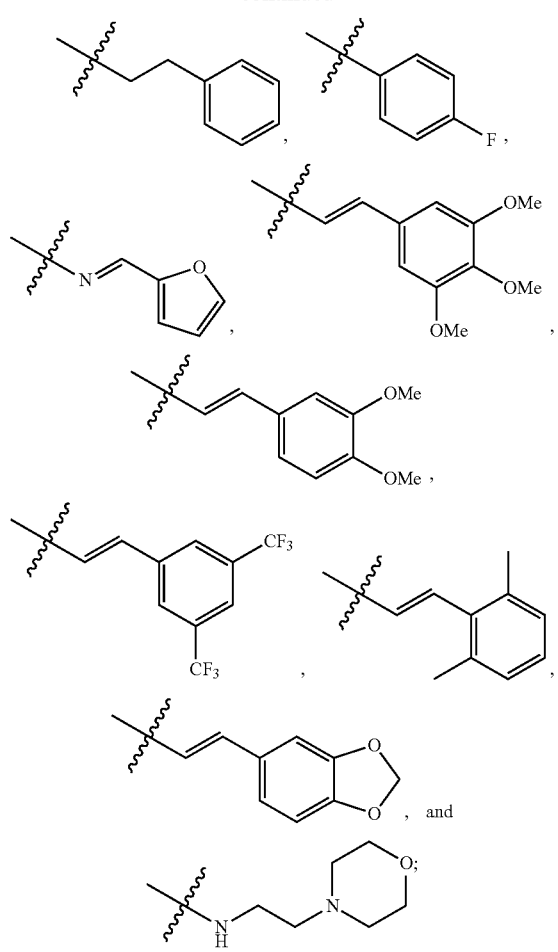
and
wherein R3 is selected from the group consisting of hydrogen, OH, OCH₃ OCH₂CH₃ COOH, COOCH₃ COOCH₂CH₃,
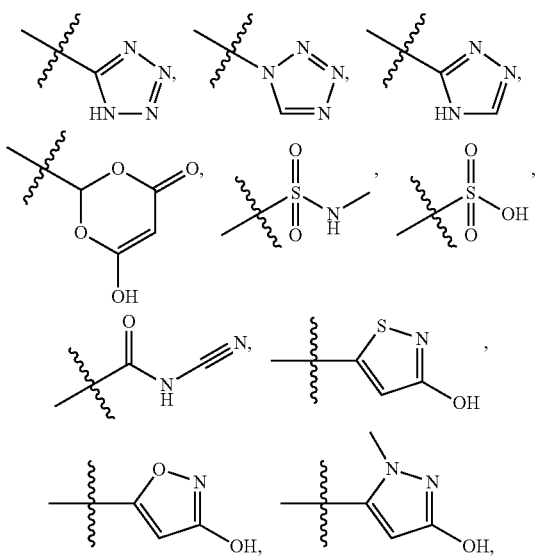
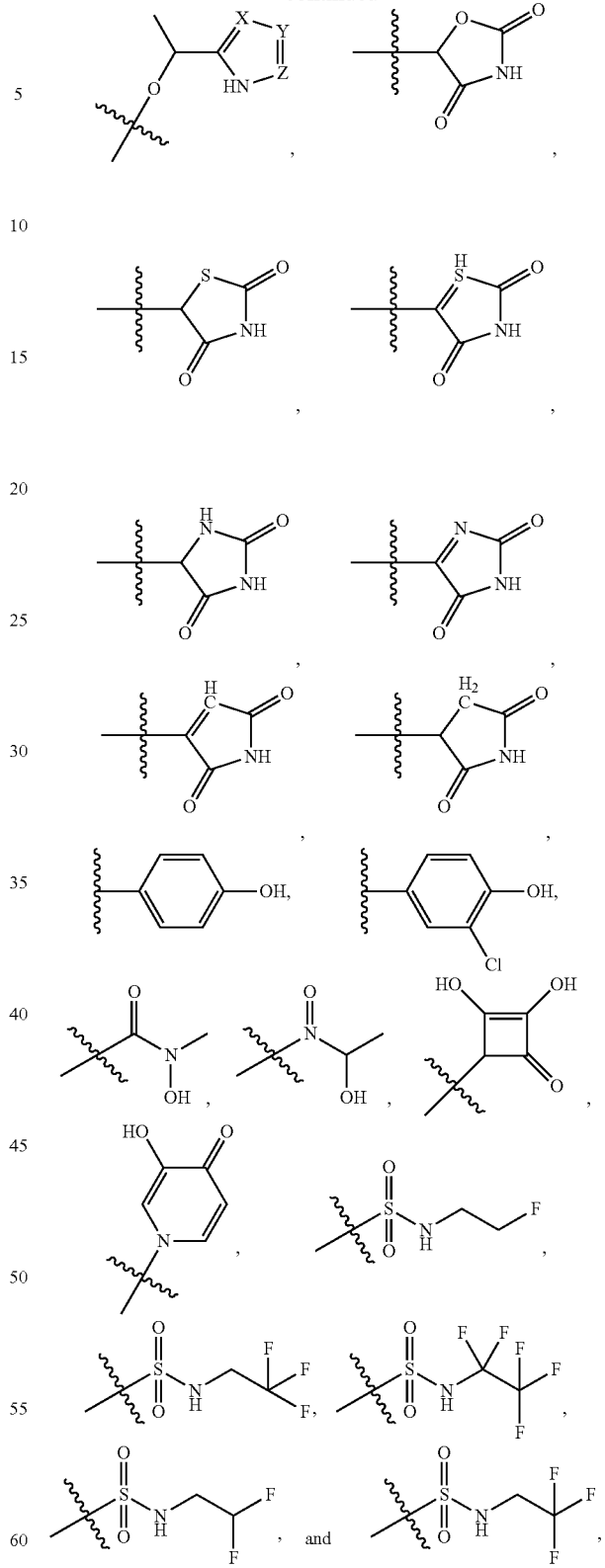
wherein X, Y, Z are independently N, C or CO.
2. The compound of claim 1, wherein the compound is able to bind the BH3 binding pocket of an Mcl-1 protein.
3. The compound of claim 1, wherein said compound is selected from the group consisting of

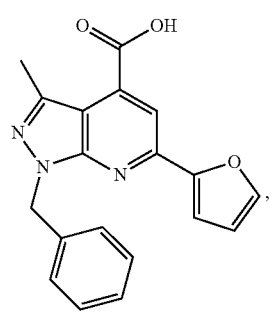
(compound 6)
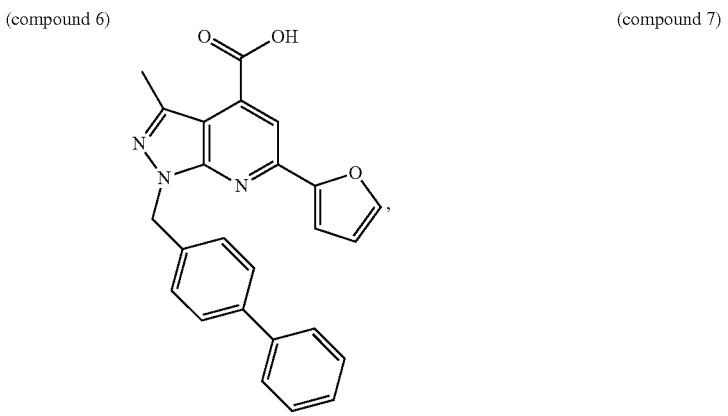
(compound 7)
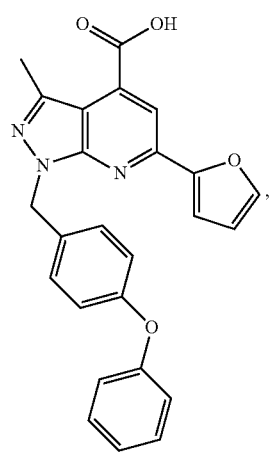
(compound 8)
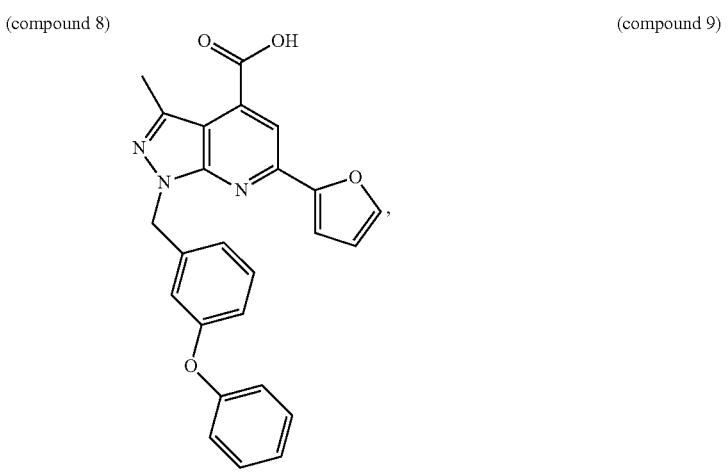
(compound 9)
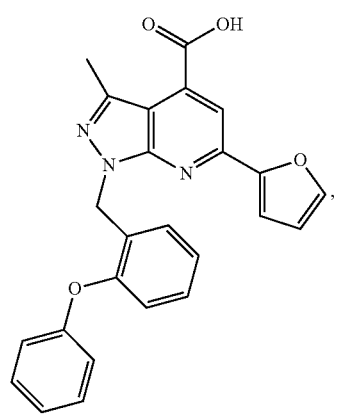
(compound 10)
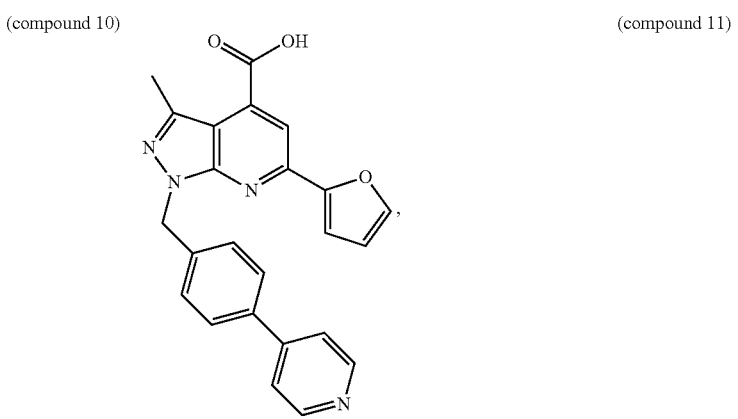
(compound 11)

-continued
(compound 12)
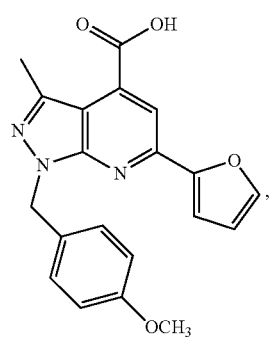
(compound 13)
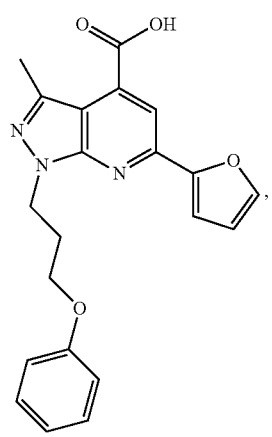
(compound 14)
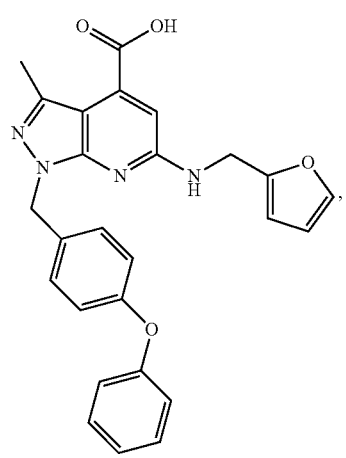
(compound 15)
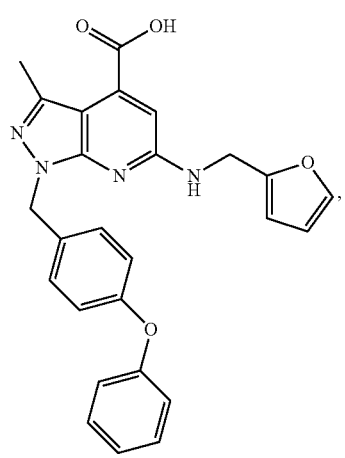
(compound 16)
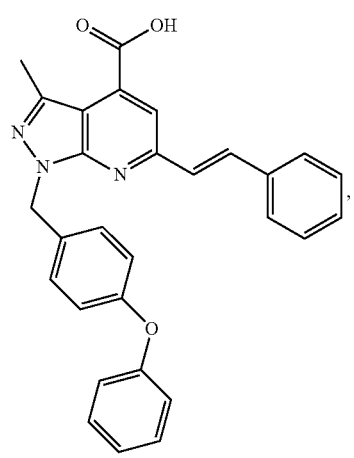
(compound 17)
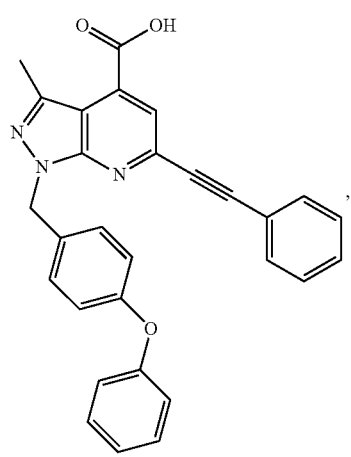

-continued
(compound 18) 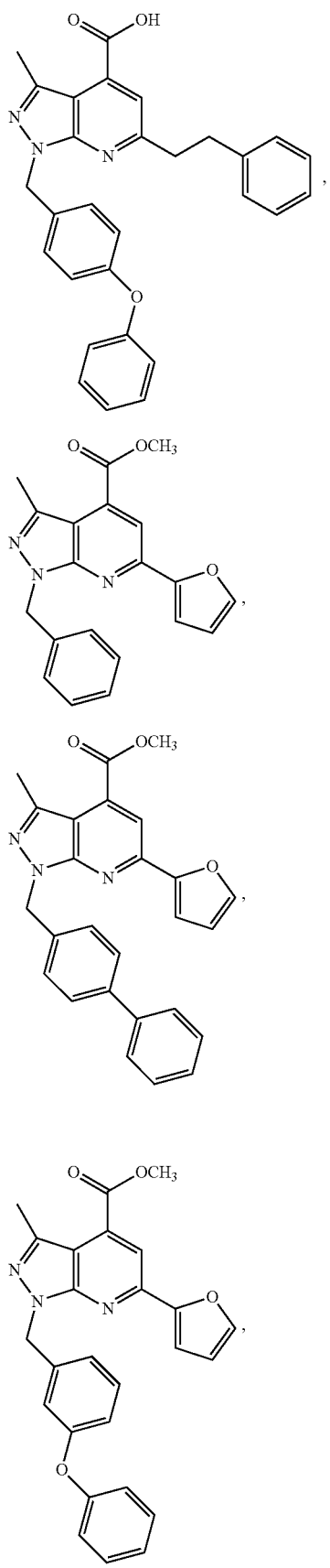
(compound 19) 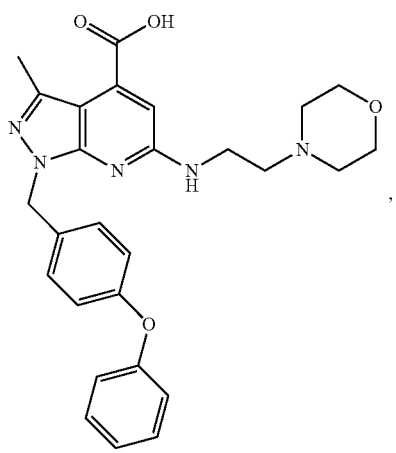
(compound 38)
(compound 39) 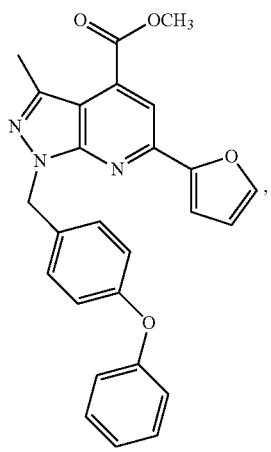
(compound 40)
(compound 41) 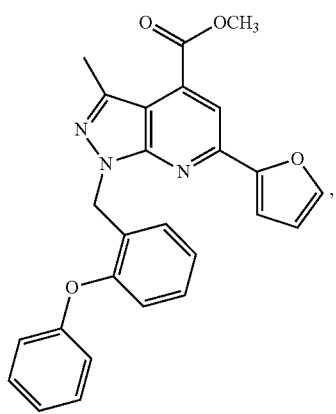
(compound 42)

-continued
(compound 43)
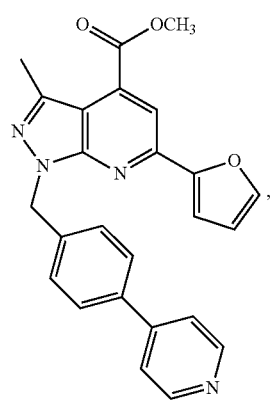
(compound 44)
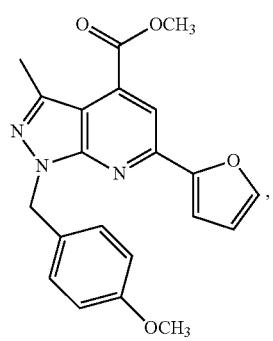
(compound 45)
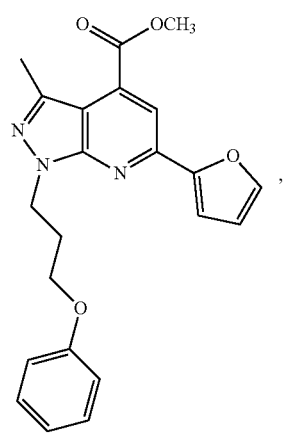
(compound 48)
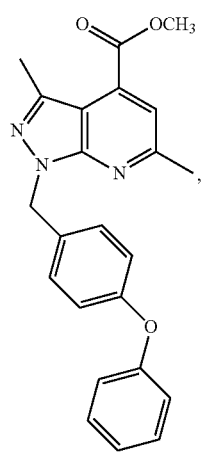
(compound 49)
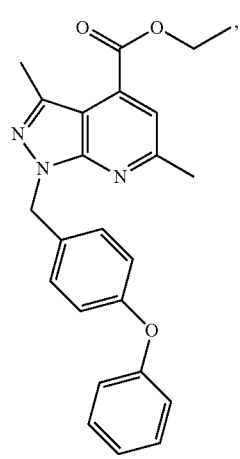
(compound 50)
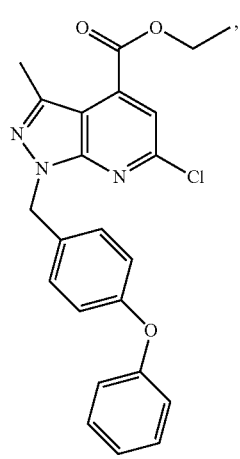

-continued
(compound 51)
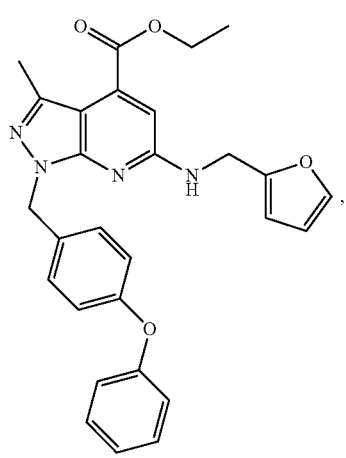
(compound 52)
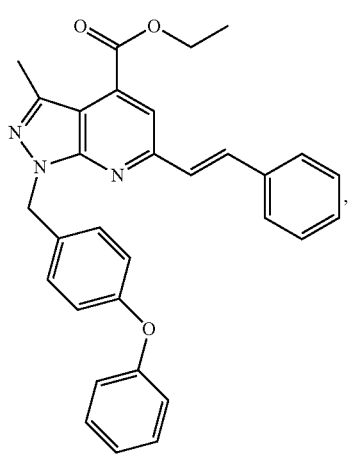
(compound 53)
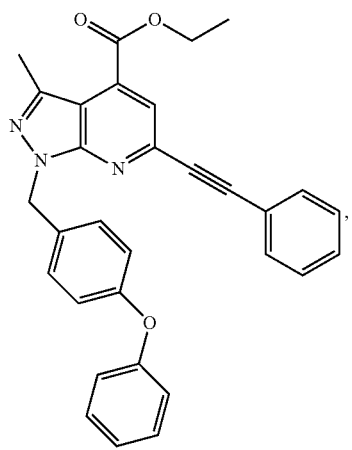
(compound 54)
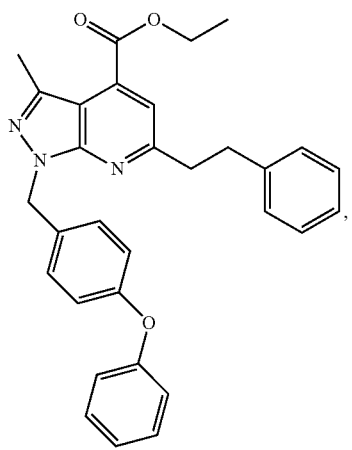
(compound 55)
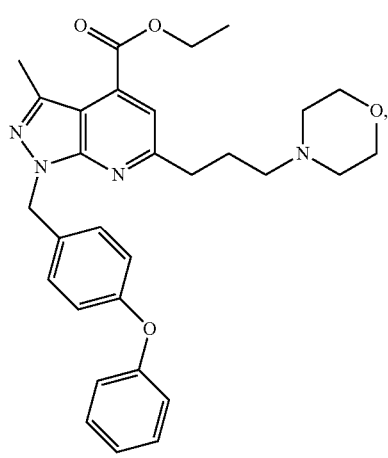

-continued
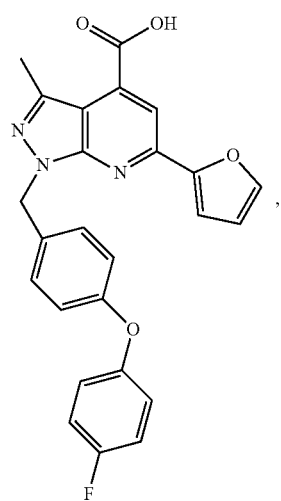
(compound 56)
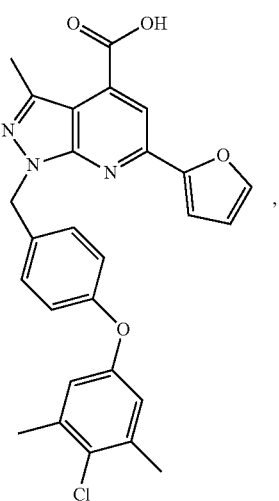
(compound 57)
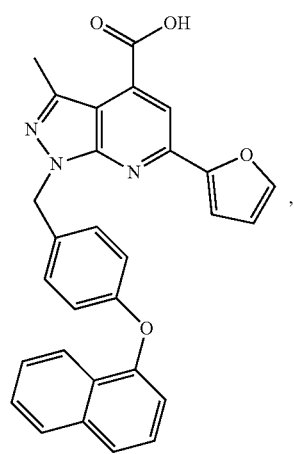
(compound 58)
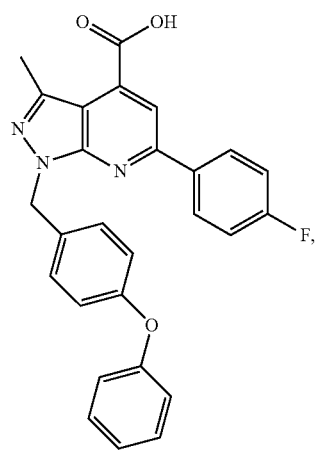
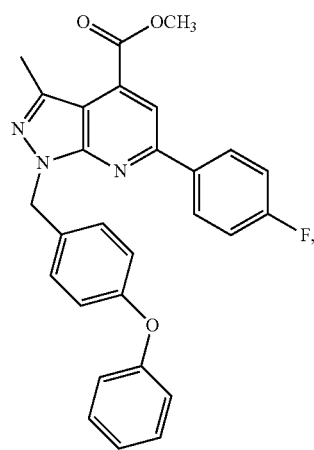
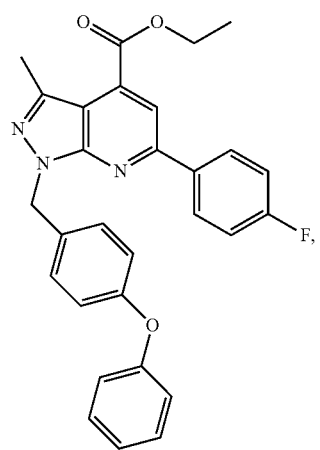

173
-continued
174
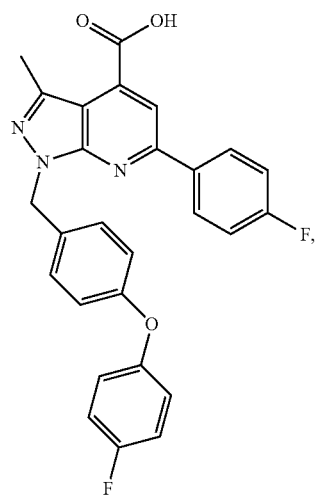 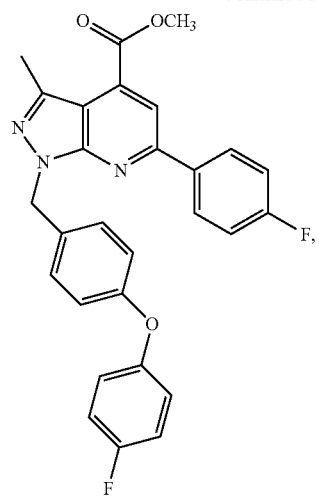 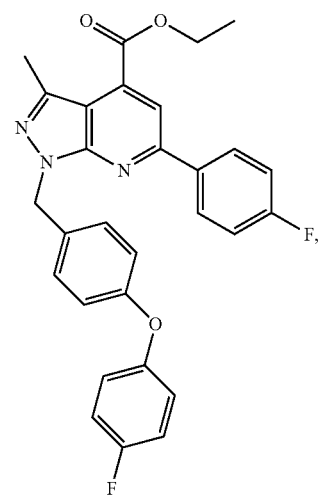
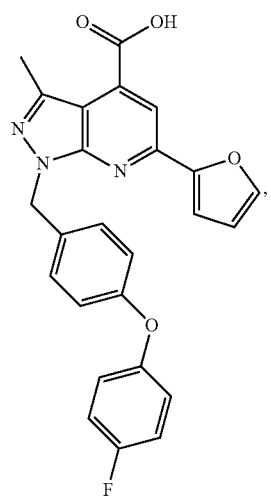 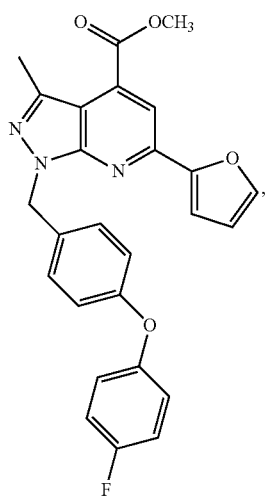 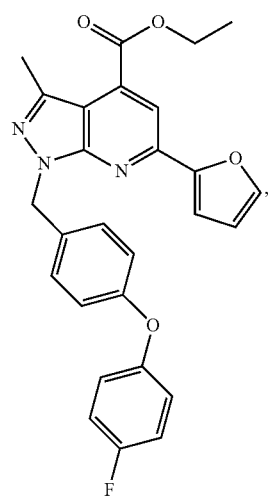 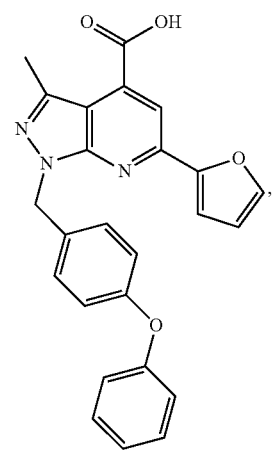
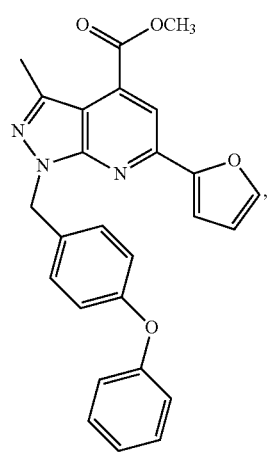 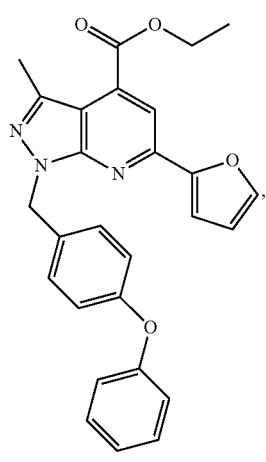 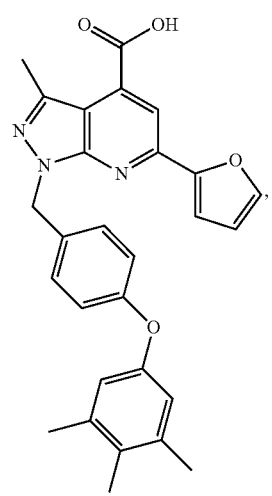 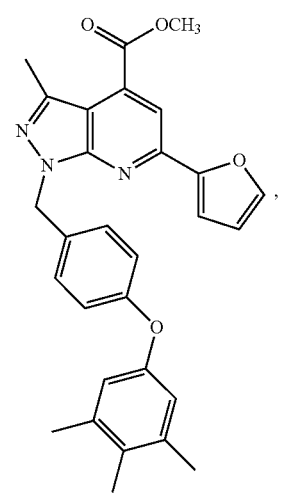

175
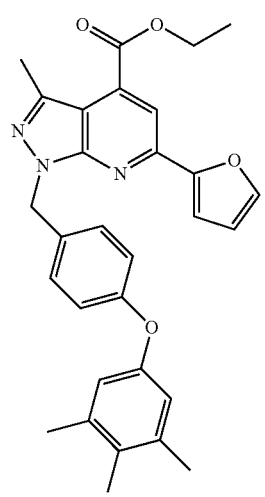 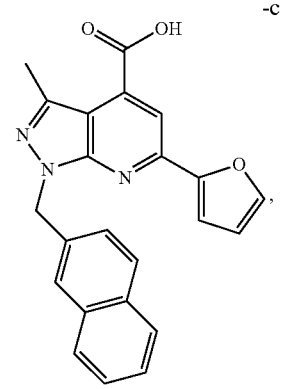 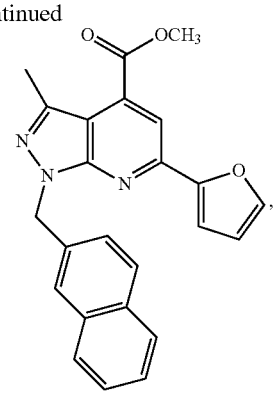
176
-continued
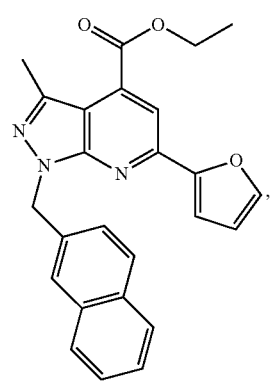
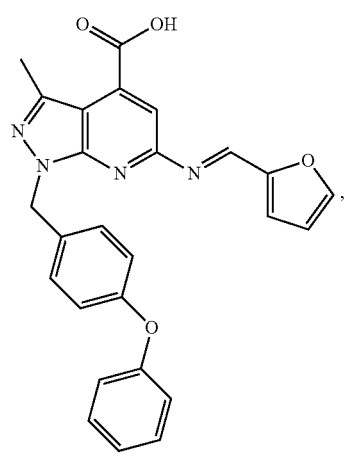 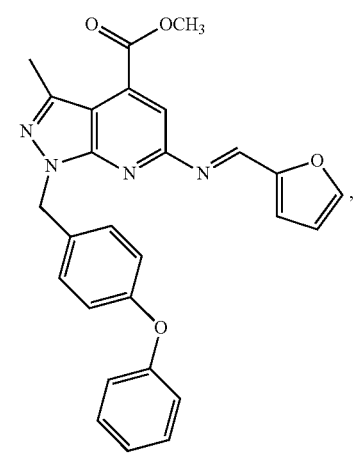 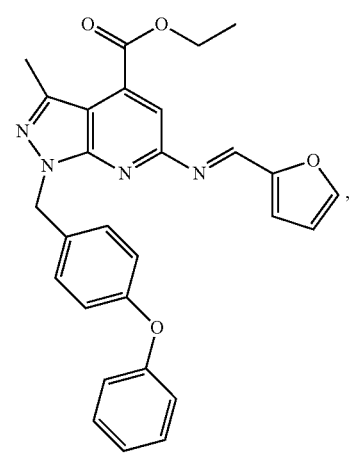
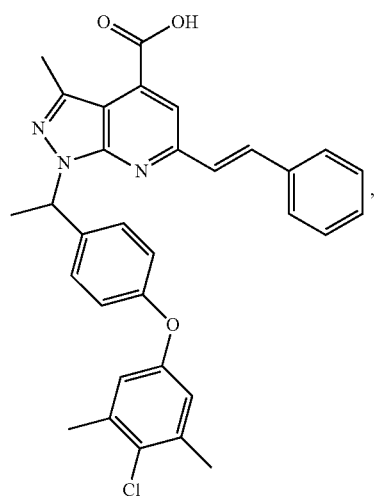 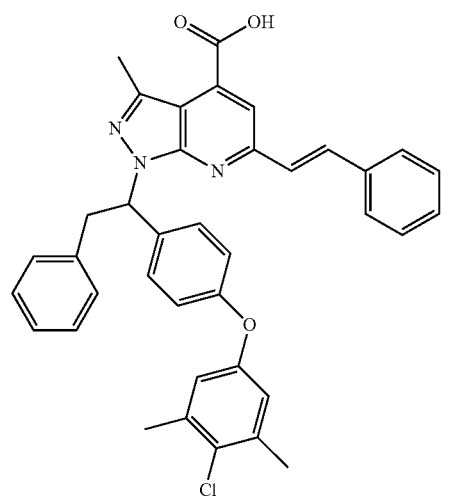

177
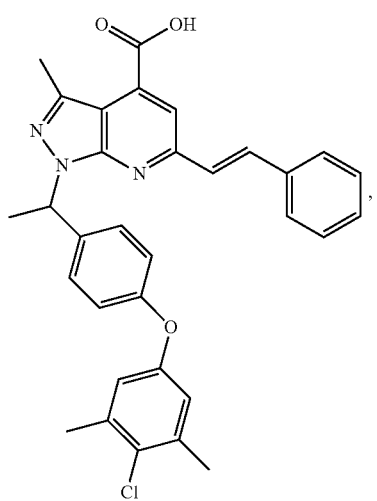
178
-continued
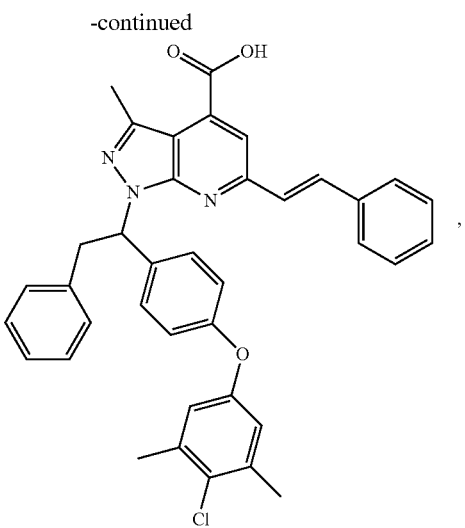
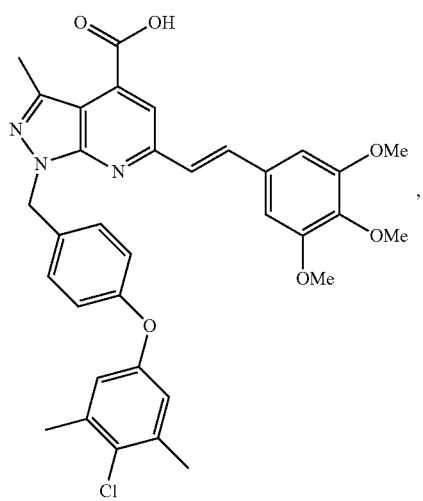
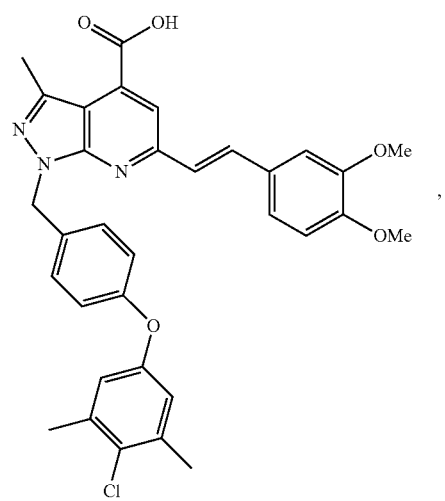
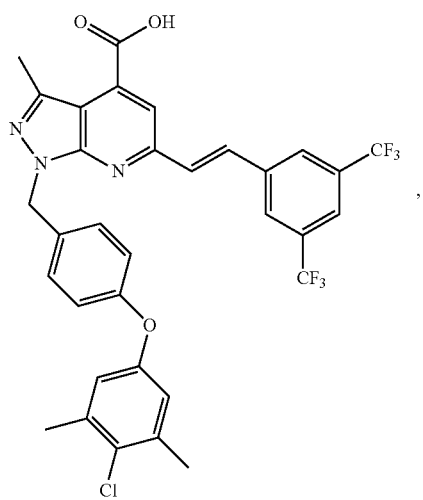
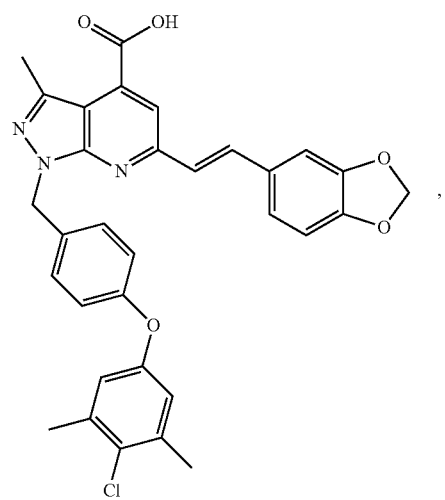

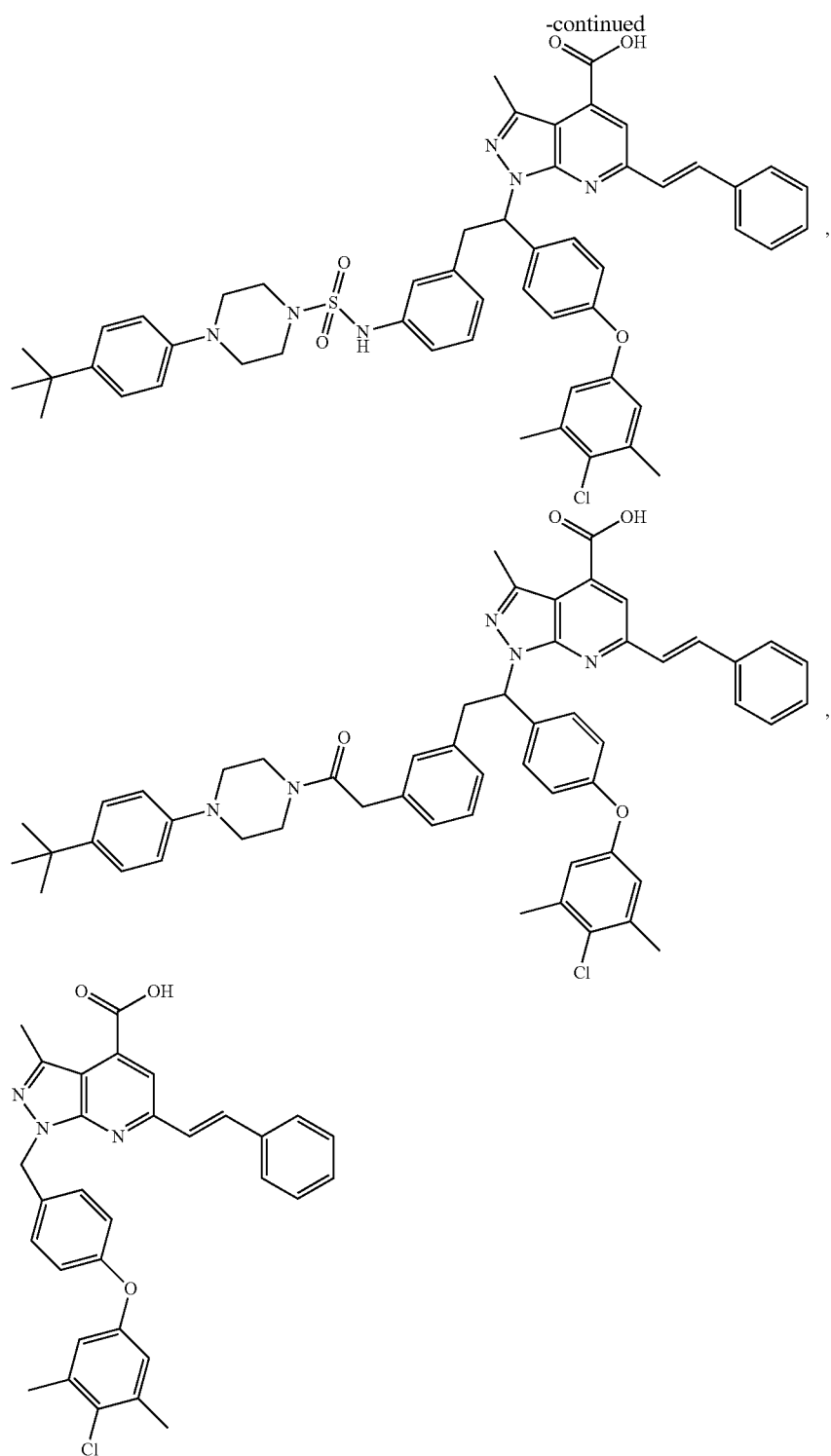
pharmaceutically acceptable carrier.
4. A pharmaceutical composition comprising a compound of claim 1.